US011512129B2

(12) United States Patent
Fu et al.

(10) Patent No.: US 11,512,129 B2
(45) Date of Patent: Nov. 29, 2022

(54) TIGIT ANTIBODY, ANTIGEN-BINDING FRAGMENT THEREOF, AND MEDICAL USE THEREOF

(71) Applicants: JIANGSU HENGRUI MEDICINE CO., LTD., Jiangsu (CN); SHANGHAI HENGRUI PHARMACEUTICAL CO., LTD., Shanghai (CN)

(72) Inventors: Yayuan Fu, Shanghai (CN); Zhuoxiao Cao, Shanghai (CN); Qiyue Hu, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 127 days.

(21) Appl. No.: 16/651,764

(22) PCT Filed: Sep. 28, 2018

(86) PCT No.: PCT/CN2018/108246
§ 371 (c)(1),
(2) Date: Mar. 27, 2020

(87) PCT Pub. No.: WO2019/062832
PCT Pub. Date: Apr. 4, 2019

(65) Prior Publication Data
US 2020/0255516 A1 Aug. 13, 2020

(30) Foreign Application Priority Data
Sep. 29, 2017 (CN) .......................... 201710908565.3

(51) Int. Cl.
*A61K 39/395* (2006.01)
*C07K 16/28* (2006.01)
*G01N 33/68* (2006.01)

(52) U.S. Cl.
CPC ..... *C07K 16/2803* (2013.01); *G01N 33/6854* (2013.01); *C07K 2317/24* (2013.01); *C07K 2317/565* (2013.01); *C07K 2317/567* (2013.01); *C07K 2317/76* (2013.01); *C07K 2317/77* (2013.01); *C07K 2317/92* (2013.01); *C07K 2317/94* (2013.01); *G01N 2333/70503* (2013.01)

(58) Field of Classification Search
CPC ..... G01N 33/6854; G01N 2333/70503; C07K 2317/24; C07K 2317/565; C07K 2317/76; A61K 39/001111; A61K 39/395
USPC .................................................... 424/133.1
See application file for complete search history.

(56) References Cited

U.S. PATENT DOCUMENTS

| | | |
|---|---|---|
| 9,499,596 B2 | 11/2016 | Clark et al. |
| 10,124,061 B2 | 11/2018 | White et al. |
| 10,507,244 B2 | 12/2019 | Hicklin et al. |
| 10,544,219 B2 | 1/2020 | Gurney et al. |
| 10,946,095 B2 | 3/2021 | Mandelboim et al. |
| 2016/0176963 A1 | 6/2016 | Maurer et al. |
| 2021/0395366 A1* | 12/2021 | Li .......................... A61P 35/00 |

FOREIGN PATENT DOCUMENTS

| | | |
|---|---|---|
| CN | 103073644 A | 5/2013 |
| CN | 107148430 A | 9/2017 |
| CN | 107207594 A | 9/2017 |
| WO | 2016028656 A1 | 2/2016 |
| WO | 2016191643 A2 | 12/2016 |
| WO | 2017037707 A1 | 3/2017 |
| WO | 2017059095 A1 | 4/2017 |
| WO | 2017152088 A1 | 9/2017 |

OTHER PUBLICATIONS

George et al. (Circulation. 1998; 97: 900-906).*
Rudikoff et al (Proc Natl Acad Sci USA 1982 vol. 79 p. 1979).*
MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Huang et al. (Appl Microbiol Biotechnol (2010) 87:401—410).*
Chen et al. (J. Mol. Bio. (1999) 293, 865-881).*
Wu et al. (J. Mol. Biol. (1999) 294, 151-162).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3)793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Partial Supplementary European Search Report for European Application No. 18863534.6, issued by the European Patent Office, dated Aug. 25, 2021, 19 pages.
International Search Report dated Dec. 29, 2018 in International Application No. PCT/CN2018/108246.

(Continued)

*Primary Examiner* — Lynn A Bristol
(74) *Attorney, Agent, or Firm* — Ice Miller LLP

(57) ABSTRACT

A TIGIT antibody, an antigen-binding fragment thereof, and a medical use thereof. The present invention relates to a murine antibody, a chimeric antibody, and a humanized antibody comprising a CDR region of the TIGIT antibody, and a pharmaceutical composition comprising the TIGIT antibody and the antigen-binding fragment thereof, and a use thereof as a medicament. In particular, the present invention also relates to a use of a humanized TIGIT antibody for preparing a medicament for the treatment of TIGIT-associated diseases or conditions.

19 Claims, 5 Drawing Sheets

Specification includes a Sequence Listing.

(56) References Cited

OTHER PUBLICATIONS

Stanietsky, N. et al., "The Interaction of TIGIT With PVR and PVRL2 Inhibits Human NK Cell Cytotoxicity," Proceedings of the National Academy of Sciences, vol. 106, No. 42, Oct. 20, 2009.
Lozano, E. et al., "The TIGIT/CD226 Axis Regulates Human T Cell Function," The Journal of Immunology, vol. 188, No. 8, Mar. 16, 2012.
Mianieri, Nicholas A. et al. "TIGIT: A Key Inhibitor of the Cancer Immunity Cycle," Trends in Immunology, vol. 38, No. 1 (Jan. 2017), pp. 20-28.
Johnston, Robert J. et al. "The Immunoreceptor TIGIT Regulates Antitumor and Antiviral CD8+ T Cell Effector Function," Cancer Cell, vol. 26 (Dec. 8, 2014) pp. 923-937.
Pauken, Kristen E. et al. "TIGIT and CD226: Tipping the Balance between Costimulatory and Coinhibitory Molecules to Augment the Cancer Immunotherapy Toolkit," Cancer Cell, vol. 26 (Dec. 8, 2014), pp. 785-787.
Stanietsky, Noa et al. "The interaction of TIGIT with PVR and PVRL2 inhibits human NK cell cytotoxicity," Proceedings of the National Academy of Sciences (PNAS), vol. 106, No. 42 (Oct. 20, 2009), pp. 17858-17863.
Millipore Sigma, Tris hydrochloride (10812846001 Roche), accessed May 26, 2022.

\* cited by examiner

SEQUENCE LISTING

```
<160> NUMBER OF SEQ ID NOS: 81

<210> SEQ ID NO 1
<211> LENGTH: 372
<212> TYPE: PRT
<213> ORGANISM: Artificial sequence
<220> FEATURE:
<223> OTHER INFORMATION: Fusion protein consisting of TIGIT
      extracellular domain and mouse IgG2aFc fragment: TIGIT-mFc

<400> SEQUENCE: 1

Met Glu Phe Gly Leu Ser Trp Leu Phe Leu Val Ala Ile Leu Lys Gly
1               5                   10                  15

Val Gln Cys Met Met Thr Gly Thr Ile Glu Thr Thr Gly Asn Ile Ser
            20                  25                  30

Ala Glu Lys Gly Gly Ser Ile Ile Leu Gln Cys His Leu Ser Ser Thr
        35                  40                  45

Thr Ala Gln Val Thr Gln Val Asn Trp Glu Gln Gln Asp Gln Leu Leu
    50                  55                  60

Ala Ile Cys Asn Ala Asp Leu Gly Trp His Ile Ser Pro Ser Phe Lys
65                  70                  75                  80

Asp Arg Val Ala Pro Gly Pro Gly Leu Gly Leu Thr Leu Gln Ser Leu
                85                  90                  95

Thr Val Asn Asp Thr Gly Glu Tyr Phe Cys Ile Tyr His Thr Tyr Pro
            100                 105                 110

Asp Gly Thr Tyr Thr Gly Arg Ile Phe Leu Glu Val Leu Glu Ser Ser
        115                 120                 125

Val Ala Glu His Gly Ala Arg Phe Gln Ile Pro Glu Pro Arg Gly Pro
    130                 135                 140

Thr Ile Lys Pro Cys Pro Pro Cys Lys Cys Pro Ala Pro Asn Leu Leu
145                 150                 155                 160

Gly Gly Pro Ser Val Phe Ile Phe Pro Pro Lys Ile Lys Asp Val Leu
                165                 170                 175

Met Ile Ser Leu Ser Pro Ile Val Thr Cys Val Val Asp Val Ser
            180                 185                 190

Glu Asp Asp Pro Asp Val Gln Ile Ser Trp Phe Val Asn Asn Val Glu
        195                 200                 205

Val His Thr Ala Gln Thr Gln Thr His Arg Glu Asp Tyr Asn Ser Thr
    210                 215                 220

Leu Arg Val Val Ser Ala Leu Pro Ile Gln His Gln Asp Trp Met Ser
225                 230                 235                 240

Gly Lys Glu Phe Lys Cys Lys Val Asn Asn Lys Asp Leu Pro Ala Pro
                245                 250                 255

Ile Glu Arg Thr Ile Ser Lys Pro Lys Gly Ser Val Arg Ala Pro Gln
            260                 265                 270

Val Tyr Val Leu Pro Pro Glu Glu Glu Met Thr Lys Lys Gln Val
        275                 280                 285

Thr Leu Thr Cys Met Val Thr Asp Phe Met Pro Glu Asp Ile Tyr Val
```

```
            290                 295                 300
Glu Trp Thr Asn Asn Gly Lys Thr Glu Leu Asn Tyr Lys Asn Thr Glu
305                 310                 315                 320

Pro Val Leu Asp Ser Asp Gly Ser Tyr Phe Met Tyr Ser Lys Leu Arg
                325                 330                 335

Val Glu Lys Lys Asn Trp Val Glu Arg Asn Ser Tyr Ser Cys Ser Val
            340                 345                 350

Val His Glu Gly Leu His Asn His His Thr Thr Lys Ser Phe Ser Arg
        355                 360                 365

Thr Pro Gly Lys
    370

<210> SEQ ID NO 2
<211> LENGTH: 371
<212> TYPE: PRT
<213> ORGANISM: Artificial sequence
<220> FEATURE:
<223> OTHER INFORMATION: Fusion protein consisting of TIGIT
      extracellular domain and human IgG1 Fc fragment: TIGIT-Fc

<400> SEQUENCE: 2

Met Glu Phe Gly Leu Ser Trp Leu Phe Leu Val Ala Ile Leu Lys Gly
1               5                   10                  15

Val Gln Cys Met Met Thr Gly Thr Ile Glu Thr Thr Gly Asn Ile Ser
            20                  25                  30

Ala Glu Lys Gly Gly Ser Ile Ile Leu Gln Cys His Leu Ser Ser Thr
        35                  40                  45

Thr Ala Gln Val Thr Gln Val Asn Trp Glu Gln Gln Asp Gln Leu Leu
    50                  55                  60

Ala Ile Cys Asn Ala Asp Leu Gly Trp His Ile Ser Pro Ser Phe Lys
65                  70                  75                  80

Asp Arg Val Ala Pro Gly Pro Gly Leu Gly Leu Thr Leu Gln Ser Leu
                85                  90                  95

Thr Val Asn Asp Thr Gly Glu Tyr Phe Cys Ile Tyr His Thr Tyr Pro
            100                 105                 110

Asp Gly Thr Tyr Thr Gly Arg Ile Phe Leu Glu Val Leu Glu Ser Ser
        115                 120                 125

Val Ala Glu His Gly Ala Arg Phe Gln Ile Pro Glu Pro Lys Ser Ser
    130                 135                 140

Asp Lys Thr His Thr Cys Pro Pro Cys Pro Ala Pro Glu Leu Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
                245                 250                 255

Glu Lys Thr Ile Ser Lys Ala Lys Gly Gln Pro Arg Glu Pro Gln Val
            260                 265                 270
```

```
Tyr Thr Leu Pro Pro Ser Arg Asp Glu Leu Thr Lys Asn Gln Val Ser
            275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
            340                 345                 350

His Glu Ala Leu His Asn His Tyr Thr Gln Lys Ser Leu Ser Leu Ser
        355                 360                 365

Pro Gly Lys
    370

<210> SEQ ID NO 3
<211> LENGTH: 244
<212> TYPE: PRT
<213> ORGANISM: Artificial sequence
<220> FEATURE:
<223> OTHER INFORMATION: Full-length TIGIT

<400> SEQUENCE: 3

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly
```

<210> SEQ ID NO 4
<211> LENGTH: 373
<212> TYPE: PRT
<213> ORGANISM: Artificial sequence
<220> FEATURE:
<223> OTHER INFORMATION: Fusion protein consisting of cynoTIGIT
      extracellular domain and mouse IgG2aFc fragment: cynoTIGIT-mFc

<400> SEQUENCE: 4

```
Met Glu Phe Gly Leu Ser Trp Leu Phe Leu Val Ala Ile Leu Lys Gly
1               5                   10                  15

Val Gln Cys Met Met Thr Gly Thr Ile Glu Thr Thr Gly Asn Ile Ser
            20                  25                  30

Ala Lys Lys Gly Gly Ser Val Ile Leu Gln Cys His Leu Ser Ser Thr
        35                  40                  45

Met Ala Gln Val Thr Gln Val Asn Trp Glu Gln His Asp His Ser Leu
    50                  55                  60

Leu Ala Ile Arg Asn Ala Glu Leu Gly Trp His Ile Tyr Pro Ala Phe
65                  70                  75                  80

Lys Asp Arg Val Ala Pro Gly Pro Gly Leu Gly Leu Thr Leu Gln Ser
                85                  90                  95

Leu Thr Met Asn Asp Thr Gly Glu Tyr Phe Cys Thr Tyr His Thr Tyr
            100                 105                 110

Pro Asp Gly Thr Tyr Arg Gly Arg Ile Phe Leu Glu Val Leu Glu Ser
        115                 120                 125

Ser Val Ala Glu His Ser Ala Arg Phe Gln Ile Pro Glu Pro Arg Gly
    130                 135                 140

Pro Thr Ile Lys Pro Cys Pro Pro Cys Lys Cys Pro Ala Pro Asn Leu
145                 150                 155                 160

Leu Gly Gly Pro Ser Val Phe Ile Phe Pro Pro Lys Ile Lys Asp Val
                165                 170                 175

Leu Met Ile Ser Leu Ser Pro Ile Val Thr Cys Val Val Val Asp Val
            180                 185                 190

Ser Glu Asp Asp Pro Asp Val Gln Ile Ser Trp Phe Val Asn Asn Val
        195                 200                 205

Glu Val His Thr Ala Gln Thr Gln Thr His Arg Glu Asp Tyr Asn Ser
    210                 215                 220

Thr Leu Arg Val Val Ser Ala Leu Pro Ile Gln His Gln Asp Trp Met
225                 230                 235                 240

Ser Gly Lys Glu Phe Lys Cys Lys Val Asn Asn Lys Asp Leu Pro Ala
                245                 250                 255

Pro Ile Glu Arg Thr Ile Ser Lys Pro Lys Gly Ser Val Arg Ala Pro
            260                 265                 270

Gln Val Tyr Val Leu Pro Pro Pro Glu Glu Glu Met Thr Lys Lys Gln
        275                 280                 285

Val Thr Leu Thr Cys Met Val Thr Asp Phe Met Pro Glu Asp Ile Tyr
    290                 295                 300

Val Glu Trp Thr Asn Asn Gly Lys Thr Glu Leu Asn Tyr Lys Asn Thr
305                 310                 315                 320

Glu Pro Val Leu Asp Ser Asp Gly Ser Tyr Phe Met Tyr Ser Lys Leu
                325                 330                 335

Arg Val Glu Lys Lys Asn Trp Val Glu Arg Asn Ser Tyr Ser Cys Ser
            340                 345                 350

Val Val His Glu Gly Leu His Asn His His Thr Thr Lys Ser Phe Ser
        355                 360                 365
```

```
Arg Thr Pro Gly Lys
    370

<210> SEQ ID NO 5
<211> LENGTH: 119
<212> TYPE: PRT
<213> ORGANISM: murine

<400> SEQUENCE: 5

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Asp Tyr
            20                  25                  30

His Met Tyr Trp Val Arg Gln Thr Pro Glu Lys Arg Leu Glu Trp Val
        35                  40                  45

Ala Tyr Ile Ser Lys Gly Gly Ile Ser Thr Tyr Tyr Pro Asp Thr Val
    50                  55                  60

Lys Gly Arg Phe Thr Ile Ser Arg Asp Asn Ala Lys His Thr Leu Tyr
65                  70                  75                  80

Leu Gln Met Ser Arg Leu Lys Ser Glu Asp Thr Ala Met Tyr Tyr Cys
                85                  90                  95

Ala Arg Gln Ser Ser Tyr Asp Phe Ala Met Asp Tyr Trp Gly Arg Gly
            100                 105                 110

Thr Ser Val Thr Val Ser Ser
        115

<210> SEQ ID NO 6
<211> LENGTH: 107
<212> TYPE: PRT
<213> ORGANISM: murine

<400> SEQUENCE: 6

Asp Ile Val Met Thr Gln Ser His Lys Phe Met Ser Thr Ser Val Gly
1               5                   10                  15

Val Arg Val Ser Ile Thr Cys Lys Ala Ser Gln Asp Val Gly Thr Ser
            20                  25                  30

Val Ala Trp Tyr Gln Gln Lys Pro Gly Gln Ser Pro Lys Leu Leu Ile
        35                  40                  45

Tyr Trp Ala Ser Ala Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 7
<211> LENGTH: 119
<212> TYPE: PRT
<213> ORGANISM: murine

<400> SEQUENCE: 7

Gln Val Gln Leu Gln Gln Pro Gly Ala Glu Leu Val Lys Pro Gly Ser
1               5                   10                  15

Ser Val Lys Leu Ser Cys Lys Ala Ser Gly Tyr Thr Phe Thr Asn Tyr
            20                  25                  30

Trp Met His Trp Val Lys Gln Gly Pro Gly Arg Gly Leu Glu Trp Ile
```

```
            35                  40                  45
Gly Arg Ile Asp Pro Asp Ser Thr Gly Ser Lys Tyr Asn Glu Lys Phe
 50                  55                  60

Lys Thr Lys Ala Ser Leu Thr Val Asp Thr Val Ser Gly Thr Ala Tyr
 65                  70                  75                  80

Met Gln Leu Ser Ser Leu Thr Ser Glu Asp Ser Ala Val Tyr Phe Cys
                 85                  90                  95

Ala Arg Glu Gly Ala Tyr Gly Tyr Tyr Phe Asp Tyr Trp Gly Gln Gly
                100                 105                 110

Thr Thr Leu Thr Val Ser Ser
                115

<210> SEQ ID NO 8
<211> LENGTH: 107
<212> TYPE: PRT
<213> ORGANISM: murine

<400> SEQUENCE: 8

Asp Ile Gln Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
                 20                  25                  30

Leu Ala Trp Tyr Gln Gln Lys Gln Gly Lys Ser Pro Gln Leu Leu Val
             35                  40                  45

Tyr Asn Ala Arg Thr Leu Ala Glu Ser Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln Tyr His Ser Gly Ser Pro Leu
                 85                  90                  95

Pro Phe Gly Ala Gly Thr Lys Leu Ala Leu Lys
                100                 105

<210> SEQ ID NO 9
<211> LENGTH: 120
<212> TYPE: PRT
<213> ORGANISM: murine

<400> SEQUENCE: 9

Glu Val Gln Leu Gln Gln Ser Gly Pro Val Leu Val Lys Pro Gly Pro
 1               5                  10                  15

Ser Val Lys Ile Ser Cys Lys Ala Ser Gly Phe Thr Phe Thr Asp Tyr
                 20                  25                  30

Tyr Met His Trp Val Lys Gln Ser Leu Gly Lys Ser Leu Glu Trp Ile
             35                  40                  45

Gly Leu Val Tyr Pro Tyr Asn Asp Asn Thr Gly Tyr Asn Arg Lys Phe
 50                  55                  60

Lys Gly Lys Ala Thr Leu Thr Val Asp Thr Ser Ser Thr Ala Tyr
 65                  70                  75                  80

Ile Glu Leu Asn Ser Leu Thr Ser Glu Asp Ser Ala Val Tyr Tyr Cys
                 85                  90                  95

Ala Arg Gly Gly Pro Ser Asn Trp Asn Tyr Phe Asp Tyr Trp Gly Gln
                100                 105                 110

Gly Thr Thr Leu Thr Val Ser Ser
                115                 120
```

```
<210> SEQ ID NO 10
<211> LENGTH: 107
<212> TYPE: PRT
<213> ORGANISM: murine

<400> SEQUENCE: 10

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Val Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Thr Leu Tyr Pro Leu
                85                  90                  95

Thr Phe Gly Ala Gly Thr Lys Leu Glu Leu Lys
            100                 105

<210> SEQ ID NO 11
<211> LENGTH: 119
<212> TYPE: PRT
<213> ORGANISM: murine

<400> SEQUENCE: 11

Gln Val Gln Leu Gln Gln Pro Gly Ala Glu Leu Val Lys Phe Gly Ala
1               5                   10                  15

Ser Val Lys Leu Ser Cys Lys Ala Ser Gly Tyr Thr Phe Thr Asn Tyr
            20                  25                  30

Tyr Met His Trp Val Lys Gln Arg Pro Gly Arg Gly Leu Glu Trp Ile
        35                  40                  45

Gly Arg Ile Asp Pro Thr Ser Gly Ala Thr Lys Tyr Asn Asp Asn Phe
50                  55                  60

Lys Gly Lys Ala Thr Leu Thr Val Asp Lys Pro Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Gly Gly Phe Gly Tyr Tyr Phe Asp Tyr Trp Gly Gln Gly
            100                 105                 110

Thr Thr Leu Thr Val Ser Ser
        115

<210> SEQ ID NO 12
<211> LENGTH: 107
<212> TYPE: PRT
<213> ORGANISM: murine

<400> SEQUENCE: 12

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Phe Thr Tyr
            20                  25                  30

Leu Ala Trp Tyr Gln Gln Lys Gln Gly Lys Ser Pro Gln Leu Leu Val
        35                  40                  45

Tyr Asn Ala Lys Thr Phe Ala Glu Gly Val Pro Ser Arg Phe Ser Gly
50                  55                  60
```

```
Ser Gly Ser Gly Thr Gln Phe Ser Leu Lys Ile Ser Ser Leu Gln Pro
 65                  70                  75                  80

Glu Asp Phe Gly Ile Tyr Tyr Cys Gln His Tyr Gly Ile Pro Leu
                 85                  90                  95

Pro Phe Gly Ala Gly Thr Lys Leu Glu Leu Lys
            100                 105
```

<210> SEQ ID NO 13
<211> LENGTH: 122
<212> TYPE: PRT
<213> ORGANISM: murine

<400> SEQUENCE: 13

```
Gln Val Gln Leu Gln Gln Ser Gly Thr Glu Leu Val Arg Pro Gly Thr
 1               5                  10                  15

Ser Val Lys Met Ser Cys Lys Ala Ser Gly Tyr Thr Phe Thr Asn Tyr
                20                  25                  30

Trp Ile Gly Trp Ala Lys Gln Arg Pro Gly His Gly Leu Glu Trp Ile
            35                  40                  45

Gly Asp Ile Tyr Pro Gly Gly Ala Tyr Thr Asn Tyr Asn Glu Lys Phe
 50                  55                  60

Lys Asp Lys Ala Thr Leu Thr Ala Asp Lys Ser Ser Thr Ala Tyr
 65                  70                  75                  80

Met Gln Phe Ser Ser Leu Thr Ser Glu Asp Ser Ala Ile Tyr Tyr Cys
                85                  90                  95

Thr Arg Gly Asp Tyr Tyr Asp Ser Ser Gly Arg Ala Met Asp Tyr Trp
            100                 105                 110

Gly Gln Gly Thr Ser Val Thr Val Ser Ser
            115                 120
```

<210> SEQ ID NO 14
<211> LENGTH: 113
<212> TYPE: PRT
<213> ORGANISM: murine

<400> SEQUENCE: 14

```
Asp Ile Val Met Ser Gln Ser Pro Ser Ser Leu Ala Val Ser Val Gly
 1               5                  10                  15

Glu Lys Val Ser Met Ser Cys Lys Ser Ser Gln Ser Leu Leu Tyr Ser
                20                  25                  30

Arg Asn Gln Met Asn Tyr Leu Ala Trp Tyr Gln Gln Lys Pro Gly Gln
            35                  40                  45

Ser Pro Lys Leu Leu Ile Tyr Trp Thr Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys
```

<210> SEQ ID NO 15
<211> LENGTH: 5
<212> TYPE: PRT
<213> ORGANISM: Artificial sequence
<220> FEATURE:

```
<223> OTHER INFORMATION: 1707-HCDR1

<400> SEQUENCE: 15

Asp Tyr His Met Tyr
1               5

<210> SEQ ID NO 16
<211> LENGTH: 17
<212> TYPE: PRT
<213> ORGANISM: Artificial sequence
<220> FEATURE:
<223> OTHER INFORMATION: 1707 HCDR2

<400> SEQUENCE: 16

Tyr Ile Ser Lys Gly Gly Ile Ser Thr Tyr Tyr Pro Asp Thr Val Lys
1               5                   10                  15

Gly

<210> SEQ ID NO 17
<211> LENGTH: 10
<212> TYPE: PRT
<213> ORGANISM: Artificial sequence
<220> FEATURE:
<223> OTHER INFORMATION: 1707 HCDR3

<400> SEQUENCE: 17

Gln Ser Ser Tyr Asp Phe Ala Met Asp Tyr
1               5                   10

<210> SEQ ID NO 18
<211> LENGTH: 11
<212> TYPE: PRT
<213> ORGANISM: Artificial sequence
<220> FEATURE:
<223> OTHER INFORMATION: 1707 LCDR1

<400> SEQUENCE: 18

Lys Ala Ser Gln Asp Val Gly Thr Ser Val Ala
1               5                   10

<210> SEQ ID NO 19
<211> LENGTH: 7
<212> TYPE: PRT
<213> ORGANISM: Artificial sequence
<220> FEATURE:
<223> OTHER INFORMATION: 1707 LCDR2

<400> SEQUENCE: 19

Trp Ala Ser Ala Arg His Thr
1               5

<210> SEQ ID NO 20
<211> LENGTH: 9
<212> TYPE: PRT
<213> ORGANISM: Artificial sequence
<220> FEATURE:
<223> OTHER INFORMATION: 1707 LCDR3

<400> SEQUENCE: 20

Gln Gln Tyr Ser Ser Tyr Pro Leu Thr
1               5

<210> SEQ ID NO 21
<211> LENGTH: 5
<212> TYPE: PRT
<213> ORGANISM: Artificial sequence
```

```
<220> FEATURE:
<223> OTHER INFORMATION: 1708 HCDR1

<400> SEQUENCE: 21

Asn Tyr Trp Met His
1               5

<210> SEQ ID NO 22
<211> LENGTH: 17
<212> TYPE: PRT
<213> ORGANISM: Artificial sequence
<220> FEATURE:
<223> OTHER INFORMATION: 1708 HCDR2

<400> SEQUENCE: 22

Arg Ile Asp Pro Asp Ser Thr Gly Ser Lys Tyr Asn Glu Lys Phe Lys
1               5                   10                  15
Thr

<210> SEQ ID NO 23
<211> LENGTH: 10
<212> TYPE: PRT
<213> ORGANISM: Artificial sequence
<220> FEATURE:
<223> OTHER INFORMATION: 1708 HCDR3

<400> SEQUENCE: 23

Glu Gly Ala Tyr Gly Tyr Tyr Phe Asp Tyr
1               5                   10

<210> SEQ ID NO 24
<211> LENGTH: 11
<212> TYPE: PRT
<213> ORGANISM: Artificial sequence
<220> FEATURE:
<223> OTHER INFORMATION: 1708 LCDR1

<400> SEQUENCE: 24

Arg Ala Ser Glu Asn Ile Tyr Ser Tyr Leu Ala
1               5                   10

<210> SEQ ID NO 25
<211> LENGTH: 7
<212> TYPE: PRT
<213> ORGANISM: Artificial sequence
<220> FEATURE:
<223> OTHER INFORMATION: 1708 LCDR2

<400> SEQUENCE: 25

Asn Ala Arg Thr Leu Ala Glu
1               5

<210> SEQ ID NO 26
<211> LENGTH: 9
<212> TYPE: PRT
<213> ORGANISM: Artificial sequence
<220> FEATURE:
<223> OTHER INFORMATION: 1708 LCDR3

<400> SEQUENCE: 26

Gln Tyr His Ser Gly Ser Pro Leu Pro
1               5

<210> SEQ ID NO 27
<211> LENGTH: 5
<212> TYPE: PRT
```

```
<213> ORGANISM: Artificial sequence
<220> FEATURE:
<223> OTHER INFORMATION: 1709 HCDR1

<400> SEQUENCE: 27

Asp Tyr Tyr Met His
1               5

<210> SEQ ID NO 28
<211> LENGTH: 17
<212> TYPE: PRT
<213> ORGANISM: Artificial sequence
<220> FEATURE:
<223> OTHER INFORMATION: 1709 HCDR2

<400> SEQUENCE: 28

Leu Val Tyr Pro Tyr Asn Asp Asn Thr Gly Tyr Asn Arg Lys Phe Lys
1               5                   10                  15
Gly

<210> SEQ ID NO 29
<211> LENGTH: 11
<212> TYPE: PRT
<213> ORGANISM: Artificial sequence
<220> FEATURE:
<223> OTHER INFORMATION: 1709 HCDR3

<400> SEQUENCE: 29

Gly Gly Pro Ser Asn Trp Asn Tyr Phe Asp Tyr
1               5                   10

<210> SEQ ID NO 30
<211> LENGTH: 11
<212> TYPE: PRT
<213> ORGANISM: Artificial sequence
<220> FEATURE:
<223> OTHER INFORMATION: 1709 LCDR1

<400> SEQUENCE: 30

Lys Ala Ser Gln Asn Val Val Thr Ala Val Ala
1               5                   10

<210> SEQ ID NO 31
<211> LENGTH: 7
<212> TYPE: PRT
<213> ORGANISM: Artificial sequence
<220> FEATURE:
<223> OTHER INFORMATION: 1709-LCDR2

<400> SEQUENCE: 31

Ser Ala Ser Asn Arg Tyr Thr
1               5

<210> SEQ ID NO 32
<211> LENGTH: 9
<212> TYPE: PRT
<213> ORGANISM: Artificial sequence
<220> FEATURE:
<223> OTHER INFORMATION: 1709-LCDR3

<400> SEQUENCE: 32

Gln Gln Tyr Thr Leu Tyr Pro Leu Thr
1               5

<210> SEQ ID NO 33
<211> LENGTH: 5
```

```
<212> TYPE: PRT
<213> ORGANISM: Artificial sequence
<220> FEATURE:
<223> OTHER INFORMATION: 1710-HCDR1

<400> SEQUENCE: 33

Asn Tyr Tyr Met His
1               5

<210> SEQ ID NO 34
<211> LENGTH: 17
<212> TYPE: PRT
<213> ORGANISM: Artificial sequence
<220> FEATURE:
<223> OTHER INFORMATION: 1710-HCDR2

<400> SEQUENCE: 34

Arg Ile Asp Pro Thr Ser Gly Ala Thr Lys Tyr Asn Asp Asn Phe Lys
1               5                   10                  15
Gly

<210> SEQ ID NO 35
<211> LENGTH: 10
<212> TYPE: PRT
<213> ORGANISM: Artificial sequence
<220> FEATURE:
<223> OTHER INFORMATION: 1710-HCDR3

<400> SEQUENCE: 35

Glu Gly Gly Phe Gly Tyr Tyr Phe Asp Tyr
1               5                   10

<210> SEQ ID NO 36
<211> LENGTH: 11
<212> TYPE: PRT
<213> ORGANISM: Artificial sequence
<220> FEATURE:
<223> OTHER INFORMATION: 1710-LCDR1

<400> SEQUENCE: 36

Arg Thr Ser Glu Asn Ile Phe Thr Tyr Leu Ala
1               5                   10

<210> SEQ ID NO 37
<211> LENGTH: 7
<212> TYPE: PRT
<213> ORGANISM: Artificial sequence
<220> FEATURE:
<223> OTHER INFORMATION: 1710-LCDR2

<400> SEQUENCE: 37

Asn Ala Lys Thr Phe Ala Glu
1               5

<210> SEQ ID NO 38
<211> LENGTH: 9
<212> TYPE: PRT
<213> ORGANISM: Artificial sequence
<220> FEATURE:
<223> OTHER INFORMATION: 1710-LCDR3

<400> SEQUENCE: 38

Gln His His Tyr Gly Ile Pro Leu Pro
1               5

<210> SEQ ID NO 39
```

```
<211> LENGTH: 5
<212> TYPE: PRT
<213> ORGANISM: Artificial sequence
<220> FEATURE:
<223> OTHER INFORMATION: 1711-HCDR1

<400> SEQUENCE: 39

Asn Tyr Trp Ile Gly
1               5

<210> SEQ ID NO 40
<211> LENGTH: 17
<212> TYPE: PRT
<213> ORGANISM: Artificial sequence
<220> FEATURE:
<223> OTHER INFORMATION: 1711-HCDR2

<400> SEQUENCE: 40

Asp Ile Tyr Pro Gly Gly Ala Tyr Thr Asn Tyr Asn Glu Lys Phe Lys
1               5                   10                  15

Asp

<210> SEQ ID NO 41
<211> LENGTH: 13
<212> TYPE: PRT
<213> ORGANISM: Artificial sequence
<220> FEATURE:
<223> OTHER INFORMATION: 1711-HCDR3

<400> SEQUENCE: 41

Gly Asp Tyr Tyr Asp Ser Ser Gly Arg Ala Met Asp Tyr
1               5                   10

<210> SEQ ID NO 42
<211> LENGTH: 17
<212> TYPE: PRT
<213> ORGANISM: Artificial sequence
<220> FEATURE:
<223> OTHER INFORMATION: 1711-LCDR1

<400> SEQUENCE: 42

Lys Ser Ser Gln Ser Leu Leu Tyr Ser Arg Asn Gln Met Asn Tyr Leu
1               5                   10                  15

Ala

<210> SEQ ID NO 43
<211> LENGTH: 7
<212> TYPE: PRT
<213> ORGANISM: Artificial sequence
<220> FEATURE:
<223> OTHER INFORMATION: 1711-LCDR2

<400> SEQUENCE: 43

Trp Thr Ser Thr Arg Glu Ser
1               5

<210> SEQ ID NO 44
<211> LENGTH: 9
<212> TYPE: PRT
<213> ORGANISM: Artificial sequence
<220> FEATURE:
<223> OTHER INFORMATION: 1711-LCDR3

<400> SEQUENCE: 44

Gln Gln Tyr Tyr Ser Tyr Pro Tyr Thr
1               5
```

<210> SEQ ID NO 45
<211> LENGTH: 119
<212> TYPE: PRT
<213> ORGANISM: Artificial sequence
<220> FEATURE:
<223> OTHER INFORMATION: h1707 VH-CDR graft, h1707-H1

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

His Met Tyr Trp Val Arg Gln Ala Pro Gly Lys Gly Leu Glu Trp Val
        35                  40                  45

Ala Tyr Ile Ser Lys Gly Gly Ile Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Ser Ser Tyr Asp Phe Ala Met Asp Tyr Trp Gly Arg Gly
            100                 105                 110

Thr Leu Val Thr Val Ser Ser
        115

<210> SEQ ID NO 46
<211> LENGTH: 107
<212> TYPE: PRT
<213> ORGANISM: Artificial sequence
<220> FEATURE:
<223> OTHER INFORMATION: h1707 VL-CDR graft, h1707-L1

<400> SEQUENCE: 46

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Ala Ser Ala Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Leu Glu Ile Lys
            100                 105

<210> SEQ ID NO 47
<211> LENGTH: 107
<212> TYPE: PRT
<213> ORGANISM: Artificial sequence
<220> FEATURE:
<223> OTHER INFORMATION: h1707-L2

<400> SEQUENCE: 47

Asp Ile Gln Met Thr Gln Ser Pro Ser Phe Leu Ser Ala Ser Val Gly
1               5                   10                  15

```
Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Ala Ser Ala Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Ser Ser Tyr Pro Leu
                85                  90                  95

Thr Phe Gly Gln Gly Thr Lys Leu Glu Ile Lys
            100                 105
```

<210> SEQ ID NO 48
<211> LENGTH: 107
<212> TYPE: PRT
<213> ORGANISM: Artificial sequence
<220> FEATURE:
<223> OTHER INFORMATION: h1707-L3

<400> SEQUENCE: 48

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ser Pro Lys Leu Leu Ile
        35                  40                  45

Tyr Trp Ala Ser Ala Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Ser Ser Tyr Pro Leu
                85                  90                  95

Thr Phe Gly Gln Gly Thr Lys Leu Glu Ile Lys
            100                 105
```

<210> SEQ ID NO 49
<211> LENGTH: 107
<212> TYPE: PRT
<213> ORGANISM: Artificial sequence
<220> FEATURE:
<223> OTHER INFORMATION: h1707-L4

<400> SEQUENCE: 49

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ser Pro Lys Leu Leu Ile
        35                  40                  45

Tyr Trp Ala Ser Ala Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Ser Ser Tyr Pro Leu
                85                  90                  95

Thr Phe Gly Gln Gly Thr Lys Leu Glu Ile Lys
            100                 105
```

<210> SEQ ID NO 50
<211> LENGTH: 119
<212> TYPE: PRT
<213> ORGANISM: Artificial sequence
<220> FEATURE:
<223> OTHER INFORMATION: h1707-H2

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

His Met Tyr Trp Val Arg Gln Ala Pro Gly Lys Gly Leu Glu Trp Val
        35                  40                  45

Ala Tyr Ile Ser Lys Gly Gly Ile Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Ser Arg Leu Arg Ala Glu Asp Thr Ala Val Tyr Tyr Cys
                85                  90                  95

Ala Arg Gln Ser Ser Tyr Asp Phe Ala Met Asp Tyr Trp Gly Arg Gly
            100                 105                 110

Thr Leu Val Thr Val Ser Ser
        115

<210> SEQ ID NO 51
<211> LENGTH: 119
<212> TYPE: PRT
<213> ORGANISM: Artificial sequence
<220> FEATURE:
<223> OTHER INFORMATION: h1708 VH-CDR graft, h1708-H1

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Arg Ile Asp Pro Asp Ser Thr Gly Ser Lys Tyr Asn Glu Lys Phe
    50                  55                  60

Lys Thr Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Tyr Gly Tyr Tyr Phe Asp Tyr Trp Gly Gln Gly
            100                 105                 110

Thr Leu Val Thr Val Ser Ser
        115

<210> SEQ ID NO 52
<211> LENGTH: 107
<212> TYPE: PRT
<213> ORGANISM: Artificial sequence
<220> FEATURE:
<223> OTHER INFORMATION: h1708 VL-CDR graft, h1708-L1

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
            35                  40                  45

Tyr Asn Ala Arg Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
65              70                  75                      80

Glu Asp Phe Ala Thr Tyr Tyr Cys Gln Tyr His Ser Gly Ser Pro Leu
                85                  90                  95

Pro Phe Gly Gly Gly Thr Lys Val Glu Ile Lys
            100                 105
```

<210> SEQ ID NO 53
<211> LENGTH: 107
<212> TYPE: PRT
<213> ORGANISM: Artificial sequence
<220> FEATURE:
<223> OTHER INFORMATION: h1708-L2

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Lys Leu Leu Ile
            35                  40                  45

Tyr Asn Ala Arg Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
65              70                  75                      80

Glu Asp Phe Ala Thr Tyr Tyr Cys Gln Tyr His Ser Gly Ser Pro Leu
                85                  90                  95

Pro Phe Gly Gly Gly Thr Lys Val Glu Ile Lys
            100                 105
```

<210> SEQ ID NO 54
<211> LENGTH: 119
<212> TYPE: PRT
<213> ORGANISM: Artificial sequence
<220> FEATURE:
<223> OTHER INFORMATION: h1708-H2

<400> SEQUENCE: 54

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
            35                  40                  45

Gly Arg Ile Asp Pro Asp Ser Thr Gly Ser Lys Tyr Asn Glu Lys Phe
        50                  55                  60

Lys Thr Arg Val Thr Met Thr Val Asp Thr Ser Thr Ser Thr Val Tyr
65              70                  75                      80

Met Glu Leu Ser Ser Leu Arg Ser Glu Asp Thr Ala Val Tyr Tyr Cys
                85                  90                  95
```

```
Ala Arg Glu Gly Ala Tyr Gly Tyr Tyr Phe Asp Tyr Trp Gly Gln Gly
            100                 105                 110

Thr Leu Val Thr Val Ser Ser
        115
```

<210> SEQ ID NO 55
<211> LENGTH: 119
<212> TYPE: PRT
<213> ORGANISM: Artificial sequence
<220> FEATURE:
<223> OTHER INFORMATION: h1708-H3

<400> SEQUENCE: 55

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Arg Ile Asp Pro Asp Ser Thr Gly Ser Lys Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Tyr Gly Tyr Tyr Phe Asp Tyr Trp Gly Gln Gly
            100                 105                 110

Thr Leu Val Thr Val Ser Ser
        115
```

<210> SEQ ID NO 56
<211> LENGTH: 120
<212> TYPE: PRT
<213> ORGANISM: Artificial sequence
<220> FEATURE:
<223> OTHER INFORMATION: h1709 VH-CDR graft, h1709-H1

<400> SEQUENCE: 56

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Leu Val Tyr Pro Tyr Asn Asp Asn Thr Gly Tyr Asn Arg Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Ser Asn Trp Asn Tyr Phe Asp Tyr Trp Gly Gln
            100                 105                 110

Gly Thr Leu Val Thr Val Ser Ser
        115                 120
```

<210> SEQ ID NO 57
<211> LENGTH: 107
<212> TYPE: PRT

<213> ORGANISM: Artificial sequence
<220> FEATURE:
<223> OTHER INFORMATION: h1709 VL-CDR graft, h1709-L1

<400> SEQUENCE: 57

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Val Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Thr Leu Tyr Pro Leu
                85                  90                  95

Thr Phe Gly Gly Gly Thr Lys Val Glu Ile Lys
            100                 105
```

<210> SEQ ID NO 58
<211> LENGTH: 107
<212> TYPE: PRT
<213> ORGANISM: Artificial sequence
<220> FEATURE:
<223> OTHER INFORMATION: h1709-L2

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Val Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Asp Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Thr Leu Tyr Pro Leu
                85                  90                  95

Thr Phe Gly Gly Gly Thr Lys Val Glu Ile Lys
            100                 105
```

<210> SEQ ID NO 59
<211> LENGTH: 107
<212> TYPE: PRT
<213> ORGANISM: Artificial sequence
<220> FEATURE:
<223> OTHER INFORMATION: h1709-L3

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Val Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Asp Arg Phe Ser Gly
50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Thr Leu Tyr Pro Leu
                 85                  90                  95

Thr Phe Gly Gly Gly Thr Lys Val Glu Ile Lys
                100                 105

<210> SEQ ID NO 60
<211> LENGTH: 107
<212> TYPE: PRT
<213> ORGANISM: Artificial sequence
<220> FEATURE:
<223> OTHER INFORMATION: h1709-L4

<400> SEQUENCE: 60

Asp Ile Val Met Thr Gln Ser Pro Ser Ser Leu Ser Ala Ser Val Gly
  1               5                  10                  15

Asp Arg Val Thr Ile Thr Cys Lys Ala Ser Gln Asn Val Val Thr Ala
                 20                  25                  30

Val Ala Trp Tyr Gln Gln Lys Pro Gly Lys Ser Pro Lys Leu Leu Ile
             35                  40                  45

Tyr Ser Ala Ser Asn Arg Tyr Thr Gly Val Pro Asp Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Thr Leu Tyr Pro Leu
                 85                  90                  95

Thr Phe Gly Gly Gly Thr Lys Val Glu Ile Lys
                100                 105

<210> SEQ ID NO 61
<211> LENGTH: 120
<212> TYPE: PRT
<213> ORGANISM: Artificial sequence
<220> FEATURE:
<223> OTHER INFORMATION: h1709-H2

<400> SEQUENCE: 61

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                 20                  25                  30

Tyr Met His Trp Val Arg Gln Ala Pro Gly Gln Gly Leu Glu Trp Met
             35                  40                  45

Gly Leu Val Tyr Pro Tyr Asn Asp Asn Thr Gly Tyr Asn Arg Lys Phe
 50                  55                  60

Lys Gly Arg Val Thr Met Thr Val Asp Thr Ser Thr Ser Thr Val Tyr
 65                  70                  75                  80

Met Glu Leu Asn Ser Leu Arg Ser Glu Asp Thr Ala Val Tyr Tyr Cys
                 85                  90                  95

Ala Arg Gly Gly Pro Ser Asn Trp Asn Tyr Phe Asp Tyr Trp Gly Gln
                100                 105                 110

Gly Thr Leu Val Thr Val Ser Ser
            115                 120

<210> SEQ ID NO 62
<211> LENGTH: 120
<212> TYPE: PRT
```

<213> ORGANISM: Artificial sequence
<220> FEATURE:
<223> OTHER INFORMATION: h1709-H3

<400> SEQUENCE: 62

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Leu Val Tyr Pro Tyr Asn Asp Asn Thr Gly Tyr Asn Arg Lys Phe
    50                  55                  60

Lys Gly Arg Val Thr Met Thr Val Asp Thr Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Arg Gly Gly Pro Ser Asn Trp Asn Tyr Phe Asp Tyr Trp Gly Gln
            100                 105                 110

Gly Thr Leu Val Thr Val Ser Ser
        115                 120

<210> SEQ ID NO 63
<211> LENGTH: 120
<212> TYPE: PRT
<213> ORGANISM: Artificial sequence
<220> FEATURE:
<223> OTHER INFORMATION: h1709-H4

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Tyr Met His Trp Val Arg Gln Ala Pro Gly Gln Gly Leu Glu Trp Ile
        35                  40                  45

Gly Leu Val Tyr Pro Tyr Asn Asp Asn Thr Gly Tyr Asn Arg Lys Phe
    50                  55                  60

Lys Gly Arg Val Thr Met Thr Val Asp Thr Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Arg Gly Gly Pro Ser Asn Trp Asn Tyr Phe Asp Tyr Trp Gly Gln
            100                 105                 110

Gly Thr Leu Val Thr Val Ser Ser
        115                 120

<210> SEQ ID NO 64
<211> LENGTH: 119
<212> TYPE: PRT
<213> ORGANISM: Artificial sequence
<220> FEATURE:
<223> OTHER INFORMATION: h1710 VH-CDR graft, h1710-H1

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
            35                  40                  45

Gly Arg Ile Asp Pro Thr Ser Gly Ala Thr Lys Tyr Asn Asp Asn Phe
        50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Glu Gly Gly Phe Gly Tyr Tyr Phe Asp Tyr Trp Gly Gln Gly
            100                 105                 110

Thr Thr Val Thr Val Ser Ser
            115

<210> SEQ ID NO 65
<211> LENGTH: 107
<212> TYPE: PRT
<213> ORGANISM: Artificial sequence
<220> FEATURE:
<223> OTHER INFORMATION: h1710 VL-CDR graft, h1710-L1

<400> SEQUENCE: 65

Asp Ile Gln Met Thr Gln Ser Pro Ser Ser Leu Ser Ala Ser Val Gly
 1               5                  10                  15

Asp Arg Val Thr Ile Thr Cys Arg Thr Ser Glu Asn Ile Phe Thr Tyr
            20                  25                  30

Leu Ala Trp Tyr Gln Gln Lys Pro Gly Lys Ala Pro Lys Leu Leu Ile
            35                  40                  45

Tyr Asn Ala Lys Thr Phe Ala Glu Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Gly Ile Pro Leu
                85                  90                  95

Pro Phe Gly Gln Gly Thr Lys Leu Glu Ile Lys
            100                 105

<210> SEQ ID NO 66
<211> LENGTH: 107
<212> TYPE: PRT
<213> ORGANISM: Artificial sequence
<220> FEATURE:
<223> OTHER INFORMATION: h1710-L2

<400> SEQUENCE: 66

Asp Ile Gln Met Thr Gln Ser Pro Ser Ser Leu Ser Ala Ser Val Gly
 1               5                  10                  15

Asp Arg Val Thr Ile Thr Cys Arg Thr Ser Glu Asn Ile Phe Thr Tyr
            20                  25                  30

Leu Ala Trp Tyr Gln Gln Lys Pro Gly Lys Ser Pro Lys Leu Leu Val
            35                  40                  45

Tyr Asn Ala Lys Thr Phe Ala Glu Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Gly Ile Pro Leu
                85                  90                  95

Pro Phe Gly Gln Gly Thr Lys Leu Glu Ile Lys

<210> SEQ ID NO 67
<211> LENGTH: 119
<212> TYPE: PRT
<213> ORGANISM: Artificial sequence
<220> FEATURE:
<223> OTHER INFORMATION: h1710-H2

<400> SEQUENCE: 67

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Arg Ile Asp Pro Thr Ser Gly Ala Thr Lys Tyr Asn Asp Asn Phe
    50                  55                  60

Lys Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Phe Gly Tyr Tyr Phe Asp Tyr Trp Gly Gln Gly
            100                 105                 110

Thr Thr Val Thr Val Ser Ser
        115

<210> SEQ ID NO 68
<211> LENGTH: 119
<212> TYPE: PRT
<213> ORGANISM: Artificial sequence
<220> FEATURE:
<223> OTHER INFORMATION: h1710-H3

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Arg Ile Asp Pro Thr Ser Gly Ala Thr Lys Tyr Asn Asp Asn Phe
    50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Phe Gly Tyr Tyr Phe Asp Tyr Trp Gly Gln Gly
            100                 105                 110

Thr Thr Val Thr Val Ser Ser
        115

<210> SEQ ID NO 69
<211> LENGTH: 119
<212> TYPE: PRT
<213> ORGANISM: Artificial sequence
<220> FEATURE:
<223> OTHER INFORMATION: h1710-H4

<400> SEQUENCE: 69

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Ile
        35                  40                  45

Gly Arg Ile Asp Pro Thr Ser Gly Ala Thr Lys Tyr Asn Asp Asn Phe
        50                  55                  60

Lys Gly Arg Ala Thr Leu Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Phe Gly Tyr Tyr Phe Asp Tyr Trp Gly Gln Gly
            100                 105                 110

Thr Thr Val Thr Val Ser Ser
            115

<210> SEQ ID NO 70
<211> LENGTH: 119
<212> TYPE: PRT
<213> ORGANISM: Artificial sequence
<220> FEATURE:
<223> OTHER INFORMATION: h1710-H5

<400> SEQUENCE: 70

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Lys Gln Ala Pro Gly Gln Gly Leu Glu Trp Ile
        35                  40                  45

Gly Arg Ile Asp Pro Thr Ser Gly Ala Thr Lys Tyr Asn Asp Asn Phe
        50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Phe Gly Tyr Tyr Phe Asp Tyr Trp Gly Gln Gly
            100                 105                 110

Thr Thr Val Thr Val Ser Ser
            115

<210> SEQ ID NO 71
<211> LENGTH: 120
<212> TYPE: PRT
<213> ORGANISM: Artificial sequence
<220> FEATURE:
<223> OTHER INFORMATION: h1711 VH-CDR graft, h1711-H1

<400> SEQUENCE: 71

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Ile Gly Trp Val Arg Gln Ala Pro Gly Gln Gly Leu Glu Trp Met
        35                  40                  45

Gly Asp Ile Tyr Pro Gly Gly Ala Tyr Thr Asn Tyr Asn Glu Lys Phe

```
            50                  55                  60
Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Tyr Tyr Asp Ser Ser Gly Arg Ala Met Asp Tyr Trp
                100                 105                 110

Gly Gln Gly Thr Leu Val Thr Val
            115                 120

<210> SEQ ID NO 72
<211> LENGTH: 113
<212> TYPE: PRT
<213> ORGANISM: Artificial sequence
<220> FEATURE:
<223> OTHER INFORMATION: h1711 VL-CDR graft, h1711-L1

<400> SEQUENCE: 72

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Ser
                 20                  25                  30

Arg Asn Gln Met Asn Tyr Leu Ala Trp Tyr Gln Gln Lys Pro Gly Gln
             35                  40                  45

Pro Pro Lys Leu Leu Ile Tyr Trp Thr Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Tyr Pro Tyr Thr Phe Gly Gly Gly Thr Lys Val Glu Ile
                100                 105                 110

Lys

<210> SEQ ID NO 73
<211> LENGTH: 113
<212> TYPE: PRT
<213> ORGANISM: Artificial sequence
<220> FEATURE:
<223> OTHER INFORMATION: h1711-L2

<400> SEQUENCE: 73

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Ser
                 20                  25                  30

Arg Asn Gln Met Asn Tyr Leu Ala Trp Tyr Gln Gln Lys Pro Gly Gln
             35                  40                  45

Ser Pro Lys Leu Leu Ile Tyr Trp Thr Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Tyr Pro Tyr Thr Phe Gly Gly Gly Thr Lys Val Glu Ile
                100                 105                 110

Lys
```

```
<210> SEQ ID NO 74
<211> LENGTH: 113
<212> TYPE: PRT
<213> ORGANISM: Artificial sequence
<220> FEATURE:
<223> OTHER INFORMATION: h1711-L3

<400> SEQUENCE: 74

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Leu Leu Tyr Ser
            20                  25                  30

Arg Asn Gln Met Asn Tyr Leu Ala Trp Tyr Gln Gln Lys Pro Gly Gln
        35                  40                  45

Ser Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gly Gly Thr Lys Val Glu Ile
                100                 105                 110

Lys

<210> SEQ ID NO 75
<211> LENGTH: 122
<212> TYPE: PRT
<213> ORGANISM: Artificial sequence
<220> FEATURE:
<223> OTHER INFORMATION: h1711-H2

<400> SEQUENCE: 75

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Ala Tyr Thr Asn Tyr Asn Glu Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Tyr Asp Ser Ser Gly Arg Ala Met Asp Tyr Trp
                100                 105                 110

Gly Gln Gly Thr Leu Val Thr Val Ser Ser
        115                 120

<210> SEQ ID NO 76
<211> LENGTH: 122
<212> TYPE: PRT
<213> ORGANISM: Artificial sequence
<220> FEATURE:
<223> OTHER INFORMATION: h1711-H3

<400> SEQUENCE: 76

Glu Val Gln Leu Val Gln Ser Gly Ala Glu Val Lys Lys Pro Gly Ser
```

-continued

```
                1               5                  10                  15
            Ser Val Lys Val Ser Cys Lys Ala Ser Gly Tyr Thr Phe Ser Asn Tyr
                            20                  25                  30

Trp Ile Gly Trp Val Arg Gln Ala Pro Gly Gln Gly Leu Glu Trp Ile
                        35                  40                  45

Gly Asp Ile Tyr Pro Gly Gly Ala Tyr Thr Asn Tyr Asn Glu Lys Phe
                    50                  55                  60

Lys Asp Arg Val Thr Ile Thr Ala Asp Lys Ser Thr Ser Thr Ala Tyr
             65                 70                  75                  80

Met Glu Leu Ser Ser Leu Arg Ser Glu Asp Thr Ala Val Tyr Tyr Cys
                            85                  90                  95

Ala Arg Gly Asp Tyr Tyr Asp Ser Ser Gly Arg Ala Met Asp Tyr Trp
                        100                 105                 110

Gly Gln Gly Thr Leu Val Thr Val Ser Ser
                        115                 120

<210> SEQ ID NO 77
<211> LENGTH: 122
<212> TYPE: PRT
<213> ORGANISM: Artificial sequence
<220> FEATURE:
<223> OTHER INFORMATION: h1711-H4

<400> SEQUENCE: 77

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Asn Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Ala Tyr Thr Asn Tyr Asn Glu Lys Phe
    50                  55                  60

Lys Asp Arg Val Thr Ile Thr Ala Asp Lys Ser Thr Ser Thr Ala Tyr
 65                 70                  75                  80

Met Glu Phe Ser Ser Leu Arg Ser Glu Asp Thr Ala Val Tyr Tyr Cys
            85                  90                  95

Thr Arg Gly Asp Tyr Tyr Asp Ser Ser Gly Arg Ala Met Asp Tyr Trp
        100                 105                 110

Gly Gln Gly Thr Leu Val Thr Val Ser Ser
        115                 120

<210> SEQ ID NO 78
<211> LENGTH: 327
<212> TYPE: PRT
<213> ORGANISM: Artificial sequence
<220> FEATURE:
<223> OTHER INFORMATION: human IgG4 heavy chain constant region with
      S228P mutation

<400> SEQUENCE: 78

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 79
<211> LENGTH: 107
<212> TYPE: PRT
<213> ORGANISM: homo sapiens

<400> SEQUENCE: 79

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
```

<210> SEQ ID NO 80
<211> LENGTH: 130
<212> TYPE: PRT
<213> ORGANISM: Artificial sequence
<220> FEATURE:
<223> OTHER INFORMATION: 22G2-H3Q VH

<400> SEQUENCE: 80

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Ser Ser Gly
            20                  25                  30
Ile Tyr Tyr Trp Ser Trp Ile Arg Gln Pro Pro Gly Lys Gly Leu Glu
        35                  40                  45
Trp Ile Gly Tyr Ile Tyr Tyr Ser Gly Ser Thr Asn Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Tyr Tyr Val Ser Gly Asn Tyr Tyr Asn Val Asp Tyr
            100                 105                 110
Tyr Phe Phe Gly Val Asp Val Trp Gly Gln Gly Thr Thr Val Thr Val
        115                 120                 125
Ser Ser
    130

<210> SEQ ID NO 81
<211> LENGTH: 109
<212> TYPE: PRT
<213> ORGANISM: Artificial sequence
<220> FEATURE:
<223> OTHER INFORMATION: 22G2-H3Q VL

<400> SEQUENCE: 81

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Pro
                85                  90                  95
Leu Phe Thr Phe Gly Pro Gly Thr Lys Val Asp Ile Lys
            100                 105

TIGIT ANTIBODY, ANTIGEN-BINDING FRAGMENT THEREOF, AND MEDICAL USE THEREOF

The present application is based on and claims the benefit of priority to CN application No. 201710908565.3, filed on 29 Sep. 2017, the disclosure of which herein incorporated by reference in its entirety.

FIELD OF THE INVENTION

The present disclosure relates to TIGIT antibodies and antigen-binding fragments thereof. Further, the present disclosure also relates to chimeric antibodies and humanized antibodies comprising the CDR regions of the TIGIT antibodies, and relates to pharmaceutical compositions comprising the TIGIT antibodies and antigen-binding fragments thereof, and their use as diagnostic and therapeutic agents for TIGIT-related diseases.

BACKGROUND OF THE INVENTION

In recent years, immune checkpoint therapy against immune cell co-inhibitory receptors has made great progress in tumor immunotherapy, and it becomes a global competitive hotspot to discover and verify new co-inhibitory receptors. T cells are key mediators of immune responses, and T cell activation depends on TCR signaling and costimulatory signals. The costimulatory signals are limiting signals for T cell activation, and the dysfunction thereof is involved in the development of autoimmune diseases (Immunol Rev, 2012, 248: 122-139; Autoimmun Rev, 2013, 12: 1171-1176). TIGIT (T cell immunoglobulin and ITIM domain) is a newly discovered co-inhibitory signal molecule located on the surface of natural killer (NK) cells and T cells, and is closely related to the regulation of T cells, NK cells and dendritic cells (DCs).

TIGIT gene is located on human chromosome 16, encoding type I transmembrane protein consisting of 244 amino acids. The extracellular domain of human TIGIT molecule has 141 amino acids in length, with an immunoglobulin V-like domain; the transmembrane region has 23 amino acids; and the cytoplasmic region is shorter and has 80 amino acids, with a PDZ binding domain and an ITIM motif. The TIGIT molecule is a member of immunoglobulin superfamily (IgSF), its structure is relatively conserved, and its homologous molecules are found in various mammals. The human TIGIT molecule has 88%, 67% and 58% homology to monkey, dog and murine TIGIT molecules, respectively. (Nat Immunol, 2009, 10(1): 48-57).

TIGIT molecules are mainly expressed on the surface of T cells and NK cells (Nat Immunol, 2009, 10: 48-57). TIGIT is low-expressed in both naive T cells and resting memory T cells, and is up-regulated after in vitro activation (J Immunol, 2012, 188: 3869-3875). TIGIT is expressed at a higher level on the surface of NK cells (Proc Natl Acad Sci USA, 2009, 106(42): 17858-17863). TIGIT is a potential new target for immunotherapy. Existing studies have shown that monoclonal antibodies specifically blocking TIGIT show significant anti-tumor effects in animal models (Martinet and Smyth 2015). A TIGIT antibody in combination with a PD-1 antibody is capable of promoting the killing function of CD8 T cells against HIV and melanoma, and such effect is absent by blocking CD226 (Chew, Fujita et al. 2016). Currently, there is no approved monoclonal antibody drug product that blocks TIGIT in domestic and foreign markets. Therefore there is a need to develop TIGIT monoclonal antibodies with high specificity.

TIGIT antibodies and related applications thereof have been reported in patent applications such as WO2009126688, WO2014089113, WO2015009856, WO2015143343, WO2015174439, WO2017053748, WO2017030823, WO2016106302, US20160176963, US20130251720. However, there is no TIGIT antibody applicable for clinical use to date, and there is still a need to develop new TIGIT antibodies that are more suitable for clinical applications.

SUMMARY OF THE INVENTION

The present disclosure provides monoclonal antibodies or antigen-binding fragments (also referred to as TIGIT binding molecules) that specifically bind to the amino acid sequence or three-dimensional structure of the extracellular region of TIGIT.

In one aspect, a monoclonal antibody or antigen-binding fragment thereof is provided, the monoclonal antibody or antigen-binding fragment specifically binds to a human TIGIT and the monoclonal antibody comprising a heavy chain variable region and a light chain variable region, wherein:

(i) the heavy chain variable region comprises HCDR1, HCDR2 and HCDR3 as set forth in amino acid sequences of SEQ ID NOs: 15, 16 and 17, or HCDR variants having 3, 2, or 1 amino acid difference(s) from HCDR1, HCDR2 and HCDR3 as set forth in SEQ ID NOs: 15, 16 and 17, respectively; and the light chain variable region comprises LCDR1, LCDR2 and LCDR3 as set forth in amino acid sequences of SEQ ID NOs: 18, 19 and 20, or LCDR variants having 3, 2, or 1 amino acid difference(s) from LCDR1, LCDR2 and LCDR3 as set forth in SEQ ID NOs: 18, 19 and 20, respectively; or (ii) the heavy chain variable region comprises HCDR1, HCDR2 and HCDR3 as set forth in amino acid sequences of SEQ ID NOs: 21-23, or HCDR variants having 3, 2, or 1 amino acid difference(s) from HCDR1, HCDR2 and HCDR3 as set forth in SEQ ID NOs: 21-23, respectively; and the light chain variable region comprises LCDR1, LCDR2 and LCDR3 as set forth in amino acid sequences of SEQ ID NOs: 24-26, or LCDR variants having 3, 2, or 1 amino acid difference(s) from LCDR1, LCDR2 and LCDR3 as set forth in SEQ ID NOs: 24-26, respectively; or (iii) the heavy chain variable region comprises HCDR1, HCDR2 and HCDR3 as set forth in amino acid sequences of SEQ ID NOs: 27-29, or HCDR variants having 3, 2, or 1 amino acid difference(s) from HCDR1, HCDR2 and HCDR3 as set forth in SEQ ID NOs: 27-29, respectively; and the light chain variable region comprises LCDR1, LCDR2 and LCDR3 as set forth in amino acid sequences of SEQ ID NOs: 30-32, or LCDR variants having 3, 2, or 1 amino acid difference(s) from LCDR1, LCDR2 and LCDR3 as set forth in SEQ ID NOs: 30-32, respectively; or (iv) the heavy chain variable region comprises HCDR1, HCDR2 and HCDR3 as set forth in amino acid sequences of SEQ ID NOs: 33-35, or HCDR variants having 3, 2, or 1 amino acid difference(s) from HCDR1, HCDR2 and HCDR3 as set forth in SEQ ID NOs: 33-35, respectively; and the light chain variable region comprises LCDR1, LCDR2 and LCDR3 as set forth in amino acid sequences of SEQ ID NOs: 36-38, or LCDR variants having 3, 2, or 1 amino acid difference(s) from LCDR1, LCDR2 and LCDR3 as set forth in SEQ ID NOs: 36-38, respectively; or (v) the heavy chain variable region comprises HCDR1, HCDR2 and HCDR3 as set forth in amino acid sequences of SEQ ID NOs: 39-41, or HCDR variants having 3, 2, or 1 amino acid difference(s) from HCDR1, HCDR2 and HCDR3 as set forth in SEQ ID NOs: 39-41, respectively; and the light chain variable region comprises LCDR1, LCDR2 and LCDR3 as set forth in amino acid sequences of SEQ ID NOs: 42-44, or LCDR variants having 3, 2, or 1 amino acid difference(s) from LCDR1, LCDR2 and LCDR3 as set forth in SEQ ID NOs: 42-44, respectively.

In some embodiments, the variants of the monoclonal antibody or antigen-binding fragment CDRs (including 3 heavy chain CDRs and 3 light chain CDRs) having 3, 2 or 1 amino acid difference(s) are obtained by affinity maturation methods.

In some embodiments, the monoclonal antibodies or antigen-binding fragments bind to TIGIT with an affinity (KD) of less than $10^{-8}$ M, less than $10^{-9}$ M, less than $10^{-10}$ M, or less than $10^{-11}$ M.

In some embodiments, the monoclonal antibody or antigen-binding fragment specifically binds to human TIGIT, the monoclonal antibody comprises a heavy chain variable region and a light chain variable region, wherein:

(vi) the heavy chain variable region comprises HCDR1, HCDR2 and HCDR3 region as set forth in SEQ ID NOs: 15-17, and the light chain variable region comprises LCDR1, LCDR2 and LCDR3 region as set forth in SEQ ID NOs: 18-20; or (vii) the heavy chain variable region comprises HCDR1, HCDR2 and HCDR3 region as set forth in SEQ ID NOs: 21-23, and the light chain variable region comprises LCDR1, LCDR2 and LCDR3 region as set forth in SEQ ID NOs: 24-26; or (viii) the heavy chain variable region comprises HCDR1, HCDR2 and HCDR3 region as set forth in SEQ ID NOs: 27-29, and the light chain variable region comprises LCDR1, LCDR2 and LCDR3 region as set forth in SEQ ID NOs: 30-32; or (ix) the heavy chain variable region comprises HCDR1, HCDR2 and HCDR3 region as set forth in SEQ ID NOs: 33-35, and the light chain variable region comprises LCDR1, LCDR2 and LCDR3 region as set forth in SEQ ID NOs: 36-38; or (x) the heavy chain variable region comprises HCDR1, HCDR2 and HCDR3 region as set forth in SEQ ID NOs: 39-41, and the light chain variable region comprises LCDR1, LCDR2 and LCDR3 region as set forth in SEQ ID NOs: 42-44.

In some embodiments, the monoclonal antibodies are recombinant antibodies, preferably recombinant antibodies selected from the group consisting of murine antibodies, chimeric antibodies, and humanized antibodies.

In some embodiments, the light and heavy chain FR region sequences on the humanized antibody light and heavy chain variable region are derived from human germline light and heavy chain or mutated sequences thereof, respectively.

In some embodiments, the humanized antibody comprises a heavy chain variable region as set forth in SEQ ID NOs: 45, 51, 56, 64 or 71, or a variant thereof; the variant has 1-10 amino acid mutations on the heavy chain variable region as set forth in SEQ ID NOs: 45, 51, 56, 64 or 71.

In some embodiments, the variant has 1-10 amino acid back mutation(s) on the FR region of the heavy chain variable region as set forth in SEQ ID NOs: 45, 51, 56, 64 or 71; preferably, the back mutation is selected from the group consisting of:

N84S, S85R and any combination thereof on the heavy chain variable region as set forth in SEQ ID NO: 45; or M48I, R72V, V79A and any combination thereof on the heavy chain variable region as set forth in SEQ ID NO: 51; or Y27F, M48I, R72V, V79A, S84N and any combination thereof on the heavy chain variable region as set forth in SEQ ID NO: 56; or R38K, R67K, R72V, T74K, M48I, V68A, M70L, V79A and any combination thereof on the heavy chain variable region of SEQ ID NO: 64; or G27Y, M48I, L83F, A97T and any combination thereof on the heavy chain variable region as set forth in SEQ ID NO: 71.

In some embodiments, the humanized antibody comprises a heavy chain variable region selected from the group consisting of:

(vi) a heavy chain variable region of SEQ ID NO: 45 or 50;

(vii) a heavy chain variable region as set forth in any one of SEQ ID NOs: 51 and 54 to 55;

viii) a heavy chain variable region as set forth in any one of SEQ ID NOs: 56, 61, 62 and 63;

ix) a heavy chain variable region as set forth in any one of SEQ ID NOs: 64, 67, 68, 69 and 70; and x) a heavy chain variable region as set forth in any one of SEQ ID NOs: 71, 75, 76 and 77.

In some embodiments, the humanized antibody comprises a light chain variable region as set forth in SEQ ID NOs: 46, 52, 57, 65 or 72, or a variant thereof; said back mutation involves 1-10 amino acid changes on the light chain variable region as set forth in SEQ ID NOs: 46, 52, 57, 65 or 72.

In some embodiments, the variant has 1-10 amino acid back mutation(s) on the FR region of the light chain variable region as set forth in SEQ ID NOs: 46, 52, 57, 65 or 72; Preferably, the back mutation is selected from the group consisting of:

amino acid back mutation(s) of S60D, T85D, A43S, S63T and any combination thereof on the light chain variable region of SEQ ID NO:46; or amino acid back mutation of A43S on the light chain variable region of SEQ ID NO: 52; or amino acid back mutation(s) of Q3V, A43S, S60D, Y87F and any combination thereof on the light chain variable region of SEQ ID NO: 57; or amino acid back mutation(s) of A43S, I48V and any combination thereof on the light chain variable region of SEQ ID NO: 65; or amino acid back mutation(s) of N22S, P49S and any combination thereof on the light chain variable region of SEQ ID NO:72.

In some embodiments, the humanized antibody comprises a light chain variable region selected from the group consisting of:

xi) a light chain variable region as set forth in any one of SEQ ID NOs: 46, 47, 48 and 49;

xii) a light chain variable region as set forth in SEQ ID NO: 52 or 53;

xiii) a light chain variable region as set forth in any one of SEQ ID NOs: 57, 58, 59, and 60;

xiv) a light chain variable region as set forth in SEQ ID NO: 65 or 66; and xv) a light chain variable region as set forth in any one of SEQ ID NOs: 72, 73 and 74.

In some embodiments, the humanized antibody comprises any one selected from the group consisting of:

xvi) a heavy chain variable region of SEQ ID NOs: 45 or 50 and a light chain variable region of any one of SEQ ID NOs: 46, 47, 48 and 49;

xvii) a heavy chain variable region of any one of SEQ ID NOs: 51, 54 and 55 and a light chain variable region of SEQ ID NOs: 52 or 53;

xviii) a heavy chain variable region of any one of SEQ ID NOs: 56, 61, 62 and 63 and a light chain variable region of any one of SEQ ID NOs: 57, 58, 59 and 60;

xix) a heavy chain variable region of any one of SEQ ID NOs: 64, 67, 68, 69 and 70 and a light chain variable region of SEQ ID NOs: 65 or 66; or xx) a heavy chain variable region of any one of SEQ ID NOs: 71, 75, 76 and 77 and a light chain variable region of any one of SEQ ID NOs: 72, 73 and 74.

In some embodiments of the monoclonal antibody or antigen-binding fragment thereof, the antibody is a full-length antibody, further comprising a human antibody constant region, wherein the heavy chain constant region is preferably human IgG1, IgG2, IgG3, and IgG4 antibody heavy constant region. More preferably, the full-length antibody comprises a human antibody heavy chain constant region as set forth in SEQ ID NO: 78 and a human light chain constant region as set forth in SEQ ID NO: 79.

In some embodiments of the monoclonal antibody or antigen-binding fragment thereof, the antigen-binding fragment is selected from the group consisting of Fab, Fab', F(ab') 2, single-chain antibody (scFv), dimerized V region (diabody), disulfide-stabilized V region (dsFv) and a peptide comprising CDRs.

In some embodiments, the monoclonal antibody or antigen-binding fragment thereof competes for binding to human TIGIT with the monoclonal antibodies or antigen-binding fragments thereof described above.

In another aspect, the present disclosure provides a pharmaceutical composition comprising a therapeutically effective amount of the monoclonal antibody or antigen-binding fragment thereof described above, and one or more pharmaceutically acceptable carriers, diluents, buffers or excipients. The amount of the monoclonal antibody or antigen-binding fragment thereof contained in the unit dose of the pharmaceutical composition is preferably from 0.1 to 2000 mg, more preferably from 0.1 to 1000 mg.

In another aspect, the present disclosure provides an isolated nucleic acid molecule encoding the above monoclonal antibody or antigen-binding fragment thereof.

In another aspect, the present disclosure provides a recombinant vector comprising the above nucleic acid molecule.

In another aspect, the present disclosure provides a host cell transformed with the above recombinant vector. The host cell is selected from the group consisting of a prokaryotic cell and a eukaryotic cell, preferably the host cell is a eukaryotic cell, more preferably a mammalian cell.

In another aspect, the present disclosure provides a method for producing the above monoclonal antibody or antigen-binding fragment thereof. The method comprises cultivating the above host cell in culture to form and accumulate the above monoclonal antibody or antigen-binding fragment thereof, and recovering the monoclonal antibody or antigen-binding fragment thereof from the culture.

In another aspect, the present disclosure provides a method for detecting or measuring human TIGIT, the method comprises the step of using the above monoclonal antibody or antigen-binding fragment thereof.

In another aspect, the present disclosure provides an agent for detecting or measuring human TIGIT, the reagent comprises the above monoclonal antibody or antigen-binding fragment thereof.

In another aspect, the present disclosure provides an agent for treating a disease associated with human TIGIT, the agent comprising the above monoclonal antibody or antigen-binding fragment thereof, or comprising the above pharmaceutical composition, or comprising the above nucleic acid molecule. The disease is preferably a T cell dysfunction disorder. T cell dysfunction is characterized by T cell depletion and such disorder is treated or delayed or alleviated by enhancing NK cells and activating T cells, thereby enhancing the immune activity of the organisms. More preferably, the disease is a tumor, cancer, immune disease or infectious disease. Among them, cancer is preferably selected from the group consisting of non-small cell lung cancer, small cell lung cancer, renal cell carcinoma, colorectal cancer, ovarian cancer, breast cancer, pancreatic cancer, gastric cancer, bladder cancer, esophagus cancer, mesothelioma, melanoma, head and neck cancer, thyroid cancer, sarcoma, prostate cancer, glioblastoma, cervical cancer, thymic carcinoma, leukemia, lymphoma, myeloma, mycosis fungoides, Merkel cell carcinoma, adrenocortical carcinoma, liver hepatocellular carcinoma, pancreatic duct adenocarcinoma, pheochromocytoma and ganglioneuroma, endometrial cancer and ovarian serous cystadenocarcinoma. Among them, myeloma is preferably multiple myeloma (MM). The immune disease is preferably selected from the group consisting of arthritis, inflammatory bowel disease, and psoriasis. Infectious disease is preferably chronic viral infections. In another aspect, the present disclosure provides a method of treating a disease associated with human TIGIT, the method comprising administering to a subject a pharmaceutically effective amount of the above monoclonal antibody or antigen-binding fragment thereof, or a pharmaceutical composition comprising the same, or the above nucleic acid molecule for treating the disease associated with human TIGIT, preferably the disease is a T cell dysfunction disease, more preferably tumor, cancer or infectious condition, and most preferably a CD155 positive or PVR positive tumor, cancer, or immunity disease or infectious condition.

In another aspect, the present disclosure provides use of the above monoclonal antibody or antigen-binding fragment thereof, or a pharmaceutical composition comprising the same, or the above nucleic acid molecule for the preparation of an agent for treating a disease associated with human TIGIT, preferably the disease is T cell dysfunction disease, more preferably a tumor, cancer or infectious disease, and most preferably a CD155 positive or PVR positive tumor, cancer, immune disease or infectious condition.

In another aspect, the present disclosure provides a method of treating a disease, the method comprising administering to a subject a pharmaceutically effective amount of the above monoclonal antibody or antigen-binding fragment thereof, or a pharmaceutical composition comprising the same, or the above isolated nucleic acid molecule, the disease is preferably T cell dysfunction disease, more preferably a tumor, cancer or infectious disease, most preferably a CD155 positive or PVR positive tumor, cancer or infectious disease.

DETAILED DESCRIPTION OF THE INVENTION

1. Terminology

Figure 1:
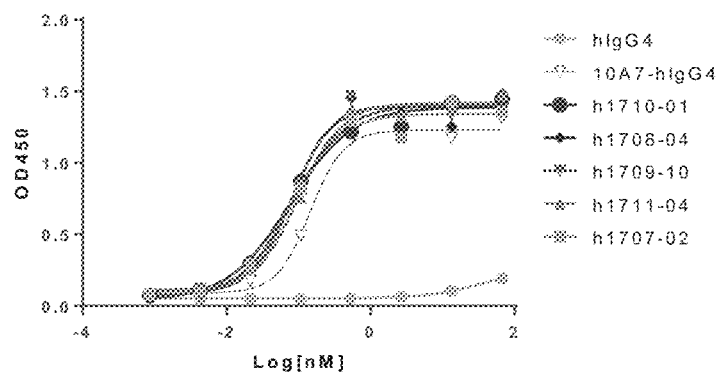
FIG. 1: Detection of the binding of TIGIT antibodies to human TIGIT protein by ELISA assay.

In order to more easily understand the present disclosure, certain technical and scientific terms are specifically defined below. Unless otherwise defined explicitly herein, all other technical and scientific terms used herein have the meaning commonly understood by one of ordinary skill in the art to which this disclosure belongs.

Three-letter codes and one-letter codes for amino acids used in the present disclosure are as described in J. biol. chem, 243, p 3558 (1968).

As used herein, "antibody" refers to immunoglobulin, a four-peptide chain structure connected together by disulfide bond between two identical heavy chains and two identical light chains. Different immunoglobulin heavy chain constant regions exhibit different amino acid compositions and rank orders, hence present different antigenicity. Accordingly, immunoglobulins can be divided into five types, or called immunoglobulin isotypes, namely IgM, IgD, IgG, IgA and IgE, with heavy chain μ, δ, γ, α and ε, respectively. According to its amino acid composition of hinge region and the number and location of heavy chain disulfide bonds, the same type of Ig can further be divided into different subtypes, for example, IgG can be divided into IgG1, IgG2, IgG3 and IgG4. Light chain can be divided into a κ or λ chain based on different constant region. Each five types of Ig can have a κ or λ chain.

In the present disclosure, the antibody light chain mentioned herein further comprises a light chain constant region, which comprises human or murine κ, λ chain or a variant thereof.

In the present disclosure, the antibody heavy chain mentioned herein further comprises a heavy chain constant region, which comprises human or murine IgG1, IgG 2, IgG 3, IgG 4 or a variant thereof.

About 110 amino acid sequences adjacent to the N-terminus of the antibody heavy and light chains are highly variable, known as variable region (Fv region); the rest of amino acid sequences close to the C-terminus are relatively stable, known as constant region. The variable region includes three hypervariable regions (HVRs) and four relatively conservative framework regions (FRs). The three hypervariable regions which determine the specificity of the antibody are also known as the complementarity determining regions (CDRs). Each light chain variable region (LCVR) and each heavy chain variable region (HCVR) consists of three CDR regions and four FR regions, with sequential order from the amino terminus to carboxyl terminus in the following order: FR1, CDR1, FR2, CDR2, FR3, CDR3, and FR4. The three CDR regions of the light chain refer to LCDR1, LCDR2, and LCDR3, and the three CDR regions of the heavy chain refer to HCDR1, HCDR2, and HCDR3. The number and position of CDR amino acid residues in the LCVR and HCVR regions of the antibody or antigen binding fragments herein comply with known Kabat numbering criteria (LCDR1-3, HCDR1-3).

Antibodies of the present disclosure include murine antibodies, chimeric antibodies, humanized antibodies, preferably humanized antibodies.

The term "murine antibody" in the present disclosure refers to anti-human TIGIT monoclonal antibody prepared according to the knowledge and skills of the field. During the preparation, test subject can be injected with TIGIT antigen, and then a hybridoma expressing the antibody which possesses the desired sequence or functional characteristics is isolated. In a preferred embodiment of the present disclosure, the murine TIGIT antibody or antigen binding fragment thereof further comprises light chain constant region of murine κ, λ chain or a variant thereof, or further comprises heavy chain constant region of murine IgG1, IgG2, IgG3, IgG4, or a variant thereof.

The term "chimeric antibody", is an antibody obtained by fusing a variable region of a murine antibody with a constant region of a human antibody, and the chimeric antibody can alleviate the murine antibody-induced immune response. To establish a chimeric antibody, a hybridoma secreting specific murine monoclonal antibody can be established and a variable region gene is cloned from the murine hybridoma. Then a desired constant region gene of human antibody can be cloned, and connected with a variable region gene of murine to form a chimeric gene which can be subsequently inserted into an expression vector. Finally, the chimeric antibody molecule will be expressed in the eukaryotic or prokaryotic system. In a preferred embodiment of the present disclosure, the light chain of the TIGIT chimeric antibody further comprises a light chain constant region derived from human κ, λ chain or a variant thereof. The heavy chain of TIGIT chimeric antibody further comprises a heavy chain constant region derived from human IgG1, IgG2, IgG3, IgG4 or a variant thereof, preferably comprises a heavy chain constant region derived from human IgG1, IgG2 or IgG4, or comprises a variant of IgG1, IgG2, IgG4 with amino acid mutation(s) (such as YTE mutation(s) or back-mutation(s), S228P).

The term "humanized antibody", including CDR-grafted antibody, refers to an antibody generated by grafting murine CDR sequences into human antibody variable region framework, i.e., an antibody produced in different types of human germline antibody framework sequences. Humanized antibody can overcome heterologous responses induced by large number of murine protein components carried by chimeric antibody. Such framework sequences can be obtained from public DNA database covering germline antibody gene sequences or published references. For example, germline DNA sequences of human heavy and light chain variable region genes can be found in "VBase" human germline sequence database (available on the world wide web (www) at: mrccpe.com.ac.uk/vbase), as well as in Kabat, E A, et al. 1991 Sequences of Proteins of Immunological Interest, 5th Ed. To avoid a decrease in activity caused by the decreased immunogenicity, the framework sequences in the variable region of human antibody can be subjected to minimal reverse mutations or back mutations to maintain the activity. The humanized antibody of the present disclosure also comprises humanized antibody on which CDR affinity maturation is performed by phage display. In a preferred embodiment of the present disclosure, the murine CDR sequence of the humanized TIGIT antibody is selected from the group consisting of SEQ ID NOs: 15-44. The human antibody variable region framework is designed and selected, wherein the FR region sequence on the heavy chain variable region, human germline heavy chain sequence is selected from the group consisting of the following combination: (IGHV3-7*01 and hjh2), (IGHV1-46*01 and hjh4.1) and (IGHV1-69*02 and hjh4.1), and the human germline light chain sequence is selected from the group consisting of the following combination: (IGKV1-39*02 and hjk2.1), (IGKV1-39*01 and hjk4.1) and (IGKV4-1*01 and hjk4.1). To avoid a decrease in activity caused by the decreased immunogenicity, the human antibody variable region can be subjected to minimal reverse mutations (back mutations, that is, the FR region amino acid residues derived from human antibody are replaced with amino acid residues corresponding to the original antibody) to maintain the activity.

The graft of CDR can result in the decrease of the affinity of the resulting TIGIT antibody or antigen binding fragment thereof to the antigen due to the framework residues contacting the antigen. Such interactions can be the result of highly somatic mutations. Therefore, it can still be necessary to transfer the donor framework amino acids to the humanized antibody framework. The amino acid residues derived from non-human TIGIT antibody or antigen binding fragment thereof, that are involved in antigen binding, can be identified by checking the sequence and structure of murine monoclonal antibody variable region. The amino acid residues in donor CDR framework that are different from those in the germ lines can be considered to be related. If it is not possible to determine the most closely related germ line, the sequence can be compared with the common sequence shared among the subtypes or with the common sequence of murine sequences having high similarity percentage. Rare framework residues are thought to be the result of a high mutation in somatic cells, which play an important role in binding.

In the expression such as "variant having 3, 2, or 1 amino acid difference(s)", the "amino acid difference" refers to the presence of amino acid change(s) or mutation(s) in the variant protein or polypeptide when compared to the original protein or polypeptide, including one or more amino acid insertion(s), deletion(s), or substitution(s) occurred on the original protein or polypeptide.

As used herein, "antigen-binding fragment" or "functional fragment" refers to one or more fragments of antibody retaining the binding ability to the antigen (e.g. TIGIT). It has been shown that fragments of full-length antibody can be used to achieve function of binding with an antigen. The examples of binding fragments in the term "antigen binding fragment" include (i) Fab fragment, a monovalent fragment composed of VL, VH, CL and CH1 domain; (ii) F(ab')2 fragment, a bivalent fragment comprising two Fab fragments linked by a disulphide bond in the hinge region; (iii) Fd fragment, consisting of VH and CH1 domains; (iv) Fv fragment, consisting of VH and VL domains of one-arm antibody; (v) single domain or dAb fragment (Ward et al. (1989) Nature341:544-546) composed of VH domain; and (vi) a separate complementary determining region (CDR) or (vii) a combination of two or more separate CDRs optionally linked by a synthetic linker. In addition, although the VL domain and VH domain of the Fv fragment are encoded by two separate genes, they can be linked by a synthetic linker by using recombinant methods, thereby generating a single protein chain of a monovalent molecular formed by pairing the VL and VH domain (referred to as single chain Fv (scFv); see, e.g., Bird et al. (1988) Science: 242 423-426; and Huston et al (1988) Proc. Natl. Acad. Sci USA85:5879-5883). This single chain antibody is also intended to be included in the term "antigen binding fragment" of the antibody. Such antibody fragments are obtained using conventional techniques known in the field, and screened for functional fragments by using the same method as that for an intact antibody. Antigen binding portions can be produced by recombinant DNA technology or by enzymatic or chemical disruption of an intact immunoglobulin. Antibodies can be in the form of different isotypes, e.g., IgG (e.g., IgG1, IgG2, IgG3 or IgG4 subtype), IgA1, IgA2, IgD, IgE or IgM antibody.

The antigen-binding fragment in the present disclosure includes Fab, F(ab')2, Fab', single-chain antibody (scFv), dimerized V region (diabody), disulfide stabilized V region (dsFv) and CDR-containing peptide.

Fab is an antibody fragment obtained by treating an IgG antibody molecule with a papain (which cleaves the amino acid residue at position 224 of the H chain). The Fab fragment has a molecular weight of about 50,000 and has antigen binding activity, in which about a half of the N-terminal side of H chain and the entire L chain are bound together through a disulfide bond.

The Fab of the present disclosure can be produced by treating the monoclonal antibody of the present invention which specifically recognizes human TIGIT and binds to the amino acid sequence of extracellular region or three-dimensional structure thereof with papain. Also, the Fab can be produced by inserting DNA encoding Fab of the antibody into a prokaryotic expression vector or eukaryotic expression vector and introducing the vector into a prokaryote or eukaryote to express the Fab.

F(ab')2 is an antibody fragment having a molecular weight of about 100,000 and having antigen binding activity and comprising two Fab regions which are bound at the hinge position, F(ab')2 is obtained by digesting the downstream part of the two disulfide bonds in the hinge region of IgG with pepsin.

The F(ab')2 of the present disclosure can be produced by treating the monoclonal antibody of the present disclosure which specifically recognizes human TIGIT and binds to the amino acid sequence of extracellular region or three-dimensional structure thereof with pepsin. Also, the F(ab')2 can be produced by binding the Fab' described below via a thioether bond or a disulfide bond.

Fab' is an antibody fragment having a molecular weight of about 50,000 and having antigen binding activity. Fab' is obtained by cleaving a disulfide bond at the hinge region of the above F(ab')2. The Fab' of the present disclosure can be produced by treating the F(ab')2 of the present invention which specifically recognizes TIGIT and binds to the amino acid sequence of extracellular region or three-dimensional structure thereof with a reducing agent, such as dithiothreitol.

Also, the Fab' can be produced by inserting DNA encoding Fab' fragment of the antibody into a prokaryotic expression vector or eukaryotic expression vector and introducing the vector into a prokaryote or eukaryote to express the Fab'.

The term "single chain antibody", "single chain Fv" or "scFv" refers to a molecule comprising an antibody heavy chain variable domain (or region; VH) and an antibody light chain variable domain (or region; VL) connected by a linker. Such scFv molecules have the general structure of NH$_2$-VL-linker-VH—COOH or NH$_2$-VH-linker-VL-COOH. A suitable linker in the prior art consists of repeated GGGGS amino acid sequence or variant thereof, for example, using a variant with 1-4 repeats (Holliger et al. (1993), Proc. Natl. Acad. Sci. USA 90:6444-6448). Other linkers that can be used for the present disclosure are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

The scFv of the present disclosure can be produced by the following steps: obtaining cDNAs encoding VH and VL of the monoclonal antibody of the present disclosure which specifically recognizes human TIGIT and binds to the amino acid sequence of extracellular region or three-dimensional structure thereof, constructing DNA encoding scFv, inserting the DNA into a prokaryotic expression vector or eukaryotic expression vector, and then introducing the expression vector into a prokaryote or eukaryote to express the scFv.

A diabody is an antibody fragment wherein the scFv is dimerized, and is an antibody fragment having divalent antigen binding activity. In the divalent antigen binding activity, two antigens can be the same or different.

The diabody of the present disclosure can be produced by the following steps, obtaining cDNAs encoding VH and VL of the monoclonal antibody of the present disclosure which specifically recognizes human TIGIT and binds to the amino acid sequence of extracellular region or three-dimensional structure thereof, constructing DNA encoding scFv so that the length of the linker peptide is 8 or less amino acid residues, inserting the DNA into a prokaryotic expression vector or eukaryotic expression vector, and then introducing the expression vector into a prokaryote or eukaryote to express the diabody.

A dsFv is obtained by substituting one amino acid residue in each of VH and VL with a cysteine residue, and then connecting the substituted polypeptides via a disulfide bond between the two cysteine residues. The amino acid residue to be substituted with a cysteine residue can be selected based on three-dimensional structure prediction of the antibody in accordance with known methods (Protein Engineering, 7, 697 (1994)).

The dsFv of the present disclosure can be produced by the following steps: obtaining cDNAs encoding VH and VL of the monoclonal antibody of the present disclosure which specifically recognizes human TIGIT and binds to the amino acid sequence of extracellular region or three-dimensional structure thereof, constructing DNA encoding dsFv, inserting the DNA into a prokaryotic expression vector or eukaryotic expression vector, and then introducing the expression vector into a prokaryote or eukaryote to express the dsFv.

A CDR-containing peptide is constructed by one or more region(s) of CDRs of VH and VL. Peptides comprising several CDRs can be joined directly or via a suitable peptide linker.

The CDR-containing peptide of the present disclosure can be produced by the steps of: constructing a DNA encoding the CDRs of VH and VL of the monoclonal antibody of the present disclosure which specifically recognizes human TIGIT and binds to the extracellular region amino acid sequence or three-dimensional structure thereof, inserting the DNA into a prokaryotic expression vector or eukaryotic expression vector, and then introducing the expression vector into a prokaryote or eukaryote to express the peptide. The CDR-containing peptide can also be produced by a chemical synthesis method such as Fmoc method or tBoc method.

The term "antibody framework" as used herein refers to part of the variable domain, either VL or VH, which serves as a scaffold for the antigen binding loops (CDRs) of this variable domain. In essence it is the variable domain without the CDRs.

The term "epitope" or "antigenic determinant" refers to a site on an antigen to which an immunoglobulin or antibody specifically binds (e.g., a specific site on the TIGIT molecule). Epitopes typically include at least 3, 4, 5, 6, 7, 8, 9, 10, 11, 12, 13, 14 or 15 consecutive or non-consecutive amino acids in a unique tertiary conformation. See, for example, Epitope Mapping Protocols in Methods in Molecular Biology, Vol. 66, ed. G. E. Morris (1996).

The term "specifically bind to", "selectively bind to", "selectively binds to" or "specifically binds to" refers to the binding of an antibody to a predetermined epitope on an antigen. Typically, the antibody binds with an affinity (KD) of less than about $10^{-7}$M, for example, less than about $10^{-9}$ M, $10^{-10}$ M or $10^{-11}$ M or even less.

The term "KD" or "Kd" refers to the dissociation equilibrium constant for particular antibody-antigen interaction. Typically, the antibody of the present disclosure binds to TIGIT with a dissociation equilibrium constant (KD) of less than about $10^{-7}$ M, such as less than about $10^{-8}$ M, $10^{-9}$ M or $10^{-10}$ M or even less, for example, as determined using surface plasmon resonance (SPR) techniques in a Biacore™ instrument.

When the term "competition" is used in the context of antigen binding proteins (e.g., neutralizing antigen binding proteins or neutralizing antibodies) that compete for the same epitope, it means that competition occurs among the antigen binding proteins, which is determined by the following assays: in the assay, an antigen binding protein to be tested (e.g., an antibody or immunologically functional fragment thereof) prevents or inhibits (e.g., reduces) the specific binding between a reference antigen binding protein (e.g., a ligand or reference antibody) and a common antigen (e.g., a TIGIT antigen or fragment thereof). Numerous types of competitive binding assays are available to determine whether an antigen binding protein competes with another. These assays are, for example, solid phase direct or indirect radioimmunoassay (RIA), solid phase direct or indirect enzyme immunoassay (EIA), Sandwich competition assay (see, e.g., Stahli et al, 1983, Methods in Enzymology 9: 242-253); solid phase direct biotin-avidin EIA (see, e.g., Kirkland et al, 1986, J. Immunol. 137: 3614-3619), solid phase direct labeling assay, solid phase direct labeling sandwich assay (see, e.g., Harlow and Lane, 1988, Antibodies, A Laboratory Manual, Cold Spring Harbor Press); solid phase direct labeling RIA with 1-125 label (see, e.g., Morel et al, 1988, Molec. Immunol. 25: 7-15); solid phase direct biotin-avidin EIA (see, e.g., Cheung, et al, 1990, Virology 176: 546-552); and direct labeling RIA (Moldenhauer et al, 1990, Scand. J. Immunol. 32: 77-82). Typically, the assay involves the use of a purified antigen (either on a solid surface or on a cell surface) capable of binding to both an unlabeled antigen binding protein to be tested and a labeled reference antigen binding protein. Competitive inhibition is determined by measuring the amount of label bound to the solid surface or to the cell in the presence of the antigen binding protein to be tested. Usually, the antigen binding protein to be tested is present in excess. Antigen binding proteins identified by competitive assay (competing with the antigen binding protein) includes: antigen binding proteins that bind to the same epitope as the reference antigen binding protein; and antigen binding proteins that bind to an epitope that is sufficiently close to the epitope to which the reference antigen binding protein binds, where the two epitopes spatially interfere with each other to hinder the binding. Additional details regarding methods for determining competitive binding are provided in the Examples herein. Typically, when a competing antigen binding protein is present in excess, it will inhibit (e.g., reduce) at least 40-45%, 45-50%, 50-55%, 55-60%, 60-65%, 65-70%, 70-75% or 75% or even more of the specific binding between the reference antigen binding protein and the common antigen. In some cases, the binding is inhibited by at least 80-85%, 85-90%, 90-95%, 95-97%, or 97% or even more.

The term "nucleic acid molecule," as used herein refers to DNA molecules and RNA molecules. A nucleic acid molecule can be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector" refers to a nucleic acid molecule capable of transporting another nucleic acid to which it has been linked. In one embodiment, the vector is a "plasmid," which refers to a circular double stranded DNA loop into which additional DNA segments can be ligated. In another embodiment, the vector is a viral vector, wherein additional DNA segments can be ligated into the viral genome. The vectors disclosed herein are capable of self-replicating in the host cell into which they are introduced (e.g., bacterial vectors having a bacterial replication origin and episomal mammalian vectors), or can be integrated into the genome of a host cell upon introduction into the host cell, and thereby are replicated along with the host genome (e.g., non-episomal mammalian vectors).

Methods for producing and purifying antibodies and antigen-binding fragments are well known in the art and can be found, for example, in Antibodies, A Laboratory Manual, Cold Spring Harbor Laboratory Press, chapters 5-8 and 15. For example, mice can be immunized with human TIGIT or fragments thereof, and the resulting antibodies can then be renatured, purified, and sequenced for amino acid sequences by using conventional methods well known in the art. Antigen-binding fragments can also be prepared by conventional methods. The antibodies or antigen binding fragments of the present disclosure are engineered to contain one or more human framework region(s) on CDRs derived from a non-human antibody. Human framework germline sequences can be obtained by aligning human antibody variable germline gene database and MOE software from ImMunoGeneTics (IMGT) via their website imgt.cines.fr, or from The Immunoglobulin Facts Book, 2001, ISBN 012441351.

The term "host cell" refers to a cell into which the expression vector has been introduced. Host cells can include bacterial, microbial, plant or animal cells. Bacteria that are susceptible to be transformed include members of enterobacteriaceae, such as *Escherichia coli* or *Salmonella* strains; Bacillaceae such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include, but are not limited to CHO (Chinese hamster ovary cell line), HEK cells (as non-limiting examples, HEK293E cells) and NSO cells.

The engineered antibodies or antigen binding fragments of the present disclosure can be prepared and purified using known methods. For example, cDNA sequence encoding a heavy chain and a light chain can be cloned and engineered into a GS expression vector. The recombinant immunoglobulin expression vector can then be stably transfected into CHO cells. As a more recommended method well known in the art, mammalian expression systems will result in glycosylation of the antibody, typically at highly conserved N-terminal sites in the Fc region. Stable clones can be verified for expression of an antibody specifically binding to human TIGIT. Positive clones can be expanded in serum-free culture medium in bioreactors for antibody production. Culture medium, into which an antibody has been secreted, can be purified by conventional techniques. For example, purification can be performed on Protein A or G Sepharose Sepharose® FF column that has been equilibrated with an adjusted buffer. The column is washed to remove nonspecific binding components, and then the bound antibody is eluted by pH gradient and antibody fractions are detected by SDS-PAGE, and then collected. The antibodies can be filtered and concentrated using common techniques. Soluble mixtures and polymers can be removed by common techniques, such as size exclusion or ion exchange. The resulting product is then immediately frozen, for example at −70° C., or can be lyophilized.

"Administering" or "treatment," as it applies to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administering" or "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administering" or "treatment" also means in vitro and ex vivo treatments, e.g., of a cell, with a reagent, diagnostic, binding composition, or with another cell. "Treatment," as it applies to a human, veterinary, or research subject, refers to therapeutic treatment, prophylactic or preventative measures, to research and diagnostic applications.

"Treat" means the administration of a therapeutic agent, such as a composition containing any of the binding compounds of the present disclosure, internally or externally to a patient having one or more disease symptom(s) for which the agent has known therapeutic activity. Typically, the agent is administered in an amount effective to alleviate one or more disease symptom(s) in the patient or population to be treated, by inducing the regression of or inhibiting the progression of such symptom(s) by any clinically measurable degree. The amount of a therapeutic agent that is effective to alleviate any particular disease symptom (also referred to as the "therapeutically effective amount") can vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present disclosure (e.g., a treatment method or article of manufacture) can not be effective in alleviating the target disease symptom(s) in every patient, it should alleviate the target disease symptom(s) in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modification" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitution in non-essential regions of a polypeptide does not substantially alter biological activity (see, e.g., Watson et al. (1987) Molecular Biology of the Gene, The Benjamin/Cummings Pub. Co., p. 224 (4th Ed.)). In addition, substitutions with structurally or functionally similar amino acids are less likely to disrupt biological activity.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject can vary depending on factors such as the condition being treated, the overall health condition of the patient, the route and dose of administration and the severity of side effects. An effective amount can be the maximal dose or dosing protocol that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptide sequences. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions to be compared and then multiplied by 100. For example, if 6 out of 10 positions in two sequences are matched or homologous when the sequences are optimally aligned, then the two sequences have 60% homology; if 95 out of 100 positions in two sequences are matched or homologous, then the two sequences have 95% homology. Generally, the comparison is performed when two sequences are aligned to give maximum percent homology.

As used herein, the expressions "cell," "cell line," and "cell culture" are used interchangeably and all such designations include progeny. Thus, the words "transformants" and "transformed cells" include the primary subject cells and cultures derived therefrom regardless of the number of passages. It should be also understood that all progeny can not be precisely identical in DNA content, due to deliberate or inadvertent mutations. Mutant progeny that have the same function or biological activity as screened in the originally transformed cells are included. Where distinct designations are intended, it will be clearly understood from the context.

As used herein, "polymerase chain reaction" or "PCR" refers to a procedure or technique in which minute amounts of a specific portion of nucleic acid, RNA and/or DNA, are amplified as described in, e.g., U.S. Pat. No. 4,683,195. Generally, sequence information about the ends of the region of interest or beyond the region of interest needs to be available, such that oligonucleotide primers can be designed; these primers will be identical or similar in sequence to opposite strands of the template to be amplified. The 5' terminal nucleotides of the two primers are consistent with the ends of the material to be amplified. PCR can be used to amplify specific RNA sequences, specific DNA sequences from total genomic DNA, and cDNA transcribed from total cellular RNA, bacteriophage or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). The PCR test used in the present disclosure is considered to be one, but not the only, example of polymerase reaction method for amplifying a nucleic acid test sample. The method comprises the use of known nucleic acid sequences as primers and nucleic acid polymerase to amplify or generate a specific portion of nucleic acid.

"Optional" or "optionally" means that the event or situation that follows can but does not necessarily occur, and the description includes the instances in which the event or circumstance does or does not occur. For example, "optionally contains 1-3 antibody heavy chain variable regions" means the antibody heavy chain variable region with specific sequence can be, but need not be present.

"Pharmaceutical composition" refers to a mixture containing one or more compound(s) according to the present disclosure or a physiologically/pharmaceutically acceptable salt or pro-drug thereof and other chemical components, such as physiologically/pharmaceutically acceptable carriers and excipients. The pharmaceutical composition aims at promoting the administration to an organism, facilitating the absorption of the active ingredient and thereby exerting a biological effect.

Furthermore, the present disclosure includes an agent for treating diseases associated with TIGIT, and the agent comprises the monoclonal antibody of the present disclosure or antibody fragment thereof as an active ingredient.

There is no limitation on the diseases associated with TIGIT, as long as they are associated with TIGIT. For example, the therapeutic responses induced by the molecules of the present disclosure can be generated by binding to human TIGIT and consequently repressing or inhibiting T cell dysfunction disease, preferably malignant tumor, cancer or infectious disease, preferably tumor or cancer in which clinical response was observed in a clinical trial by using immunotherapy drugs targeting to immunotherapy checkpoint, most preferably CD155 positive tumor, cancer, or infectious disorder.

Furthermore, the present disclosure relates to an immunodetection or immunoassay method of TIGIT, reagents for immunodetection or immunoassay of TIGIT, an immunodetection or immunoassay of cells expressing TIGIT, and a diagnostic agent for diagnosing a disease associated with TIGIT, which comprises the monoclonal antibody or antibody fragment of the present disclosure specifically recognizing human TIGIT and binding to the amino acid sequence of the extracellular region or the three-dimensional structure thereof as an active ingredient.

In the present disclosure, the method for detecting or measuring the amount of TIGIT can be any method known in the art. For example, it includes immunodetection or immunoassay.

The immunodetection or immunoassay is a method for detecting or measuring the amount of an antibody or of an antigen by using a labeled antigen or antibody. Examples of immunodetection or immunoassay include radioactive substance labeling immunological antibody method (RIA), enzyme immunoassay (EIA or ELISA), fluorescent immunoassay (FIA), luminescent immunoassay, Western Blotting, physicochemical assays, and the like.

The above diseases associated with TIGIT can be diagnosed by detecting or measuring the cells expressing TIGIT with the monoclonal antibody or antibody fragment of the present disclosure.

In order to detect cells expressing the polypeptide, a known immunoassay can be used, preferably, immunoprecipitation, fluorescent cell staining, immunohistochemical staining, and the like is used. Further, a fluorescent antibody staining method with FMAT™ 8100 HTS System (Applied Biosystem), and the like can be used.

In the present disclosure, there is not particular limitation on the living sample used for detecting or measuring TIGIT, as long as it is likely to contain cells expressing TIGIT, for example, tissue cells, blood, plasma, serum, pancreatic fluid, urine, feces, tissue fluid or culture medium can be used.

The diagnostic agent comprising the monoclonal antibody or antibody fragment thereof of the present disclosure can further comprise an agent for performing antigen-antibody reaction or an agent for detecting the reaction, depending on a desired diagnostic method. The agent for performing antigen-antibody reaction includes such as buffer and salts. The agent for detecting the reaction includes reagents commonly used in immunodetection or immunoassay method, for example, such as a labeled secondary antibody recognizing the monoclonal antibody, antibody fragment thereof or conjugate comprising the same, and a substrate corresponding to the labels.

The TIGIT monoclonal antibodies or antigen-binding fragments provided in the embodiments of the present disclosure have high specificity for TIGIT and high affinity to TIGIT. The humanized antibodies have greatly reduced immunogenicity, while the specificity of the murine antibody, high affinity and excellent in vitro and in vivo activities are completely retained.

The TIGIT monoclonal antibodies or antigen-binding fragments provided in the embodiments of the present disclosure have good metabolic kinetic characteristics in rats, exhibit long half-life, and have high bioavailability.

The TIGIT humanized antibody molecules provided in the embodiments of the present disclosure have good long-term stability, no obvious abnormal chemical modification, no obvious aggregation at high concentration, and high purity and thermal stability.

The TIGIT monoclonal antibodies or antigen-binding fragments provided in the embodiments of the present disclosure have good effect on enhancing the activity of NK cells and T cells.

EXAMPLES AND TEST EXAMPLES

The following examples are provided to further describe the present disclosure, but are not intended to limit the scope of the disclosure. Experimental methods for which the specific conditions are not specifically indicated are generally carried out according to conventional conditions, see Molecular Cloning, Laboratory Manual of antibody technology, Cold Spring Harbor Laboratory; or according to the conditions recommended by the manufacturer of materials or products. Reagents for which the sources are not specifically indicated are commercially available reagents.

Example 1. Preparation of TIGIT Antigens and Antibodies 1.1 Design and Expression of Proteins The human TIGIT protein (Uniprot No.: Q495A1) was used as a template for TIGIT of the present disclosure, and the amino acid sequences of the antigens and the proteins used for detection in the present disclosure were designed. Alternatively, different tags were fused onto the TIGIT protein, and cloned into pHr vector (produced in-house) or pXC-17.4 vector (LONZA) respectively, transiently expressed in 293 cells or stably expressed in CHO cells for purification, and the antigens and proteins used for detection in the present disclosure were obtained. TIGIT antigens hereafter all refer to human TIGIT, unless otherwise specified.

Fusion protein consisting of TIGIT extracellular domain and mouse IgG2aFc fragment: TIGIT-mFc for immunization and detection

```
                                              SEQ ID NO: 1
MEFGLSWLFLVAILKGVQCMMTGTIETTGNISAEKGGSIILQCHLSST
TAQVTQVNWEQQDQLLAICNADLGWHISPSFKDRVAPGPGLGLTLQSL
TVNDTGEYFCIYHTYPDGTYTGRIFLEVLESSVAEHGARFQIPEPRGP
TIKPCPPCKCPAPNLLGGPSVFIFPPKIKDVLMISLSPIVTCVVVDVS
EDDPDVQISWFVNNVEVHTAQTQTHREDYNSTLRVVSALPIQHQDWMS
GKEFKCKVNNKDLPAPIERTISKPKGSVRAPQVYVLPPPEEEMTKKQV
TLTCMVTDFMPEDIYVEWTNNGKTELNYKNTEPVLDSDGSYRMYSKLR
VEKKNWVERNSYSCSVVHEGLHEGLHNHHTTKSFSRTPGK*
```

Note:
The underlined text shows signal peptide and the italic text shows mFc.

Fusion protein consisting of TIGIT extracellular domain and human IgG1 Fc fragment: TIGIT-Fc for detection

```
                                              SEQ ID NO: 2
MEFGLSWLFLVAILKGVQCMMTGTIETTGNISAEKGGSIILQCHLSST
TAQVTQVNWEQQDQLLAICNADLGWHISPSFKDRVAPGPGLGLTLQS
LTVNDTGEYFCIYHTYPDGTYTGRIFLEVLESSVAEHGARFQIPEPKS
SDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQV
SLTCLVKGFFYPSDIAVEWESNGQPENNYKTTPPVLDSGSFFLYSKL
TVDKSRWQQGNVFSCSVMHEALHNHYTQKSLSLSPGK*
```

Note:
The underlined text shows signal peptide and the italic text shows Fc.

Full-length TIGIT: for construction of cell lines overexpressing TIGIT, for detection

```
                                              SEQ ID NO: 3
MRWCLLLIWAQGLRQAPLASGMMTGTIETTGNISAEKGGSIILQCHLS
STTAQVTQVNWEQQDQLLAICNADLGWHISPSFKDRVAPGPGLGLTLQ
SLTVNDTGEYFCIYHTYPDGTYTGRIFLEVLESSVAEHGARFQIPLLG
AMAATLVVICTAVIVVVALTRKKKALRIHSVEGDLRRKSAGQEEWSPS
APSPPGSCVQAEAAPAGLCGEQRGEDCAELHDYFNVLSYRSLGNCSFF
TETG
```

Signal peptide (single underlined text) + extracellular domain + transmembrane domain (doubly underlined text) + intracellular domain (italic text)

Fusion protein consisting of cynoTIGIT extracellular domain and mouse IgG2aFc fragment: cynoTIGIT-mFc, for detection

SEQ ID NO: 4

<u>MEFGLSWLFLVAILKGVQCMMTGTI</u>ETTGNISAKKGGSVILQCHLSST
MAQVTQVNWEQHDHSLLAIRNAELGWHIYPAFKDRVAPGPGLGLTLQS
LTMNDTGEYFCTYHTYPDGTYRGRIFLEVLESSVAEHSARFQI*PEPRG
PTIKPCPPCKCPAPNLLGGPSVFIFPPKIKDVLMISLSPIVTCVVVDV
SEDDPDVQISWFVNNVEVHTAQTQTHREDYNSTLRVVSALPIQHQDWM
SGKEFKCKVNNKDLPAPIERTISKPKGSVRAPQVYVLPPPEEEMTKKQ
VTLTCMVTDFMPEDIYVEWTNNGKTELNYKNTEPVLDSDGSYFMYSKL
RVEKKNWVERNSYSCSVVHEGLHNHHTTKSFSRTPGK**

Note:
The underlined text shows signal peptide and the italic text shows mFc.

1.2 Purification of TIGIT-Related Recombinant Proteins, and Purification of Hybridoma Antibodies and Recombinant Antibodies (1) Isolation, Purification/ProteinG Affinity Chromatography of Hybridoma Supernatant:

Protein G affinity chromatography was selected for purification of mouse hybridoma supernatant. The cultivated hybridoma was centrifuged to obtain a supernatant, and 10-15% (by volume of the supernatant) of 1M Tris-HCl (pH 8.0-8.5) was added to adjust pH. The Protein G column was washed with 3-5 column volumes of 6M guanidine hydrochloride, and then washed with 3-5 column volumes of pure water. The column was equilibrated with 3-5 column volumes of equilibration buffer, for example, 1×PBS (pH 7.4) buffer system. Cell supernatant was loaded and bound at low flow rate, with about 1 min or longer retention time by controlling the flow rate. The column was washed with 3-5 column volumes of 1×PBS (pH 7.4) until UV absorption dropped back to the baseline. Samples were eluted with 0.1 M acetic acid/sodium acetate (pH 3.0) buffer, and elution peaks were collected according to UV detection. The pH of the elution products was quickly adjusted to pH 5-6 with 1 M Tris-HCl (pH 8.0) for temporary storage. For elution products, solution replacement can be carried out by methods well known to those skilled in the art, for example, ultrafiltration filtration was performed with ultrafiltration tubes and the solution was replaced with a desired buffer system, or the solution was replaced with a desired buffer system by molecular exclusion such as G-25 desalination column, or the purity of the samples was improved by removing the aggregates from the elution products with high-resolution molecular exclusion columns such as Superdex 200.

(2) Extraction of Fc-Tagged Fusion Proteins or Antibodies with Protein a Affinity Chromatography:

The cell culture supernatant expressing the Fc fusion protein or antibody was first centrifuged at high speed to collect the supernatant. The Protein A column was washed with 3-5 column volumes of 6M guanidine hydrochloride, and then washed with 3-5 column volumes of pure water. The column was equilibrated with 3-5 column volumes of equilibration buffer, for example, 1×PBS (pH 7.4) buffer system. Cell supernatant was loaded and bound at low flow rate, with about 1 min or longer retention time by controlling the flow rate. The column was washed with 3-5 column volumes of 1×PBS (pH 7.4) until UV absorption dropped back to the baseline. Samples were eluted with 0.1 M acetic acid/sodium acetate (pH 3.0-3.5) buffer, and elution peaks were collected according to UV detection. The pH of the elution products was quickly adjusted to pH 5-6 with 1 M Tris-HCl (pH 8.0) for temporary storage. For elution products, solution replacement can be carried out by methods well known to those skilled in the art, for example, ultrafiltration filtration was performed with ultrafiltration tubes and the solution was replaced with a desired buffer system, or the solution was replaced with a desired buffer system by molecular exclusion such as G-25 desalination column, or the purity of the samples was improved by removing the aggregates from the elution products with high-resolution molecular exclusion columns such as Superdex 200.

Example 2 Preparation of Anti-Human TIGIT Hybridoma Monoclonal Antibodies

2.1 Immunization

Anti-human TIGIT monoclonal antibodies were produced by immunizing mice. Experimental SJL white mice, female, 6-8 weeks old (Beijing Weitong Lihua Experimental Animal Technology Co., Ltd., animal production license number: SCXK (Beijing) 2012-0001). Feeding environment was at the specific pathogen free (SPF) level. The mice were kept in the laboratory environment for 1 week after purchase, with 12/12-hour-light/dark cycle, temperature of 20-25° C. and humidity of 40-60%. Mice which have been adapted to the environment were immunized according to the following protocol. The antigen for immunization was human TIGIT extracellular domain with mFc (SEQ ID NO: 1).

Immunization protocol: Immunization was performed with TiterMax® Gold Adjuvant (Sigma Cat No. T2684) or Thermo Imject® Alum (Thermo Cat No. 77161) adjuvant alternately. The ratio of the antigen to adjuvant (TiterMax® Gold Adjuvant) was 1:1, and the ratio of the antigen to adjuvant (Thermo Imject® Alum) was 3:1, 50 μg/mice/time (first immunization), 25 μg/mice/time (booster immunization). The antigen was emulsified and inoculated at day 0, 14, 28, 42 and 56. On day 0, 50 μg/mice of emulsified antigen was injected intraperitoneally (IP). On day 14, 25 μg/mice was injected subcutaneously (s.c.) at several sites (generally 6-8 sites on the back). On day 28 and 42, the antigen was injected onto the back or intraperitoneally injected, according to the swelling condition on the back and in the abdomen. Blood was taken on day 21, 35, 49 and 63, and serum antibody titers in the mice were determined by ELISA. After the 4$^{th}$ or 5$^{th}$ immunization, mice with high serum antibody titers which tend to reach a plateau were selected for splenocyte fusion. Booster immunization was performed 3 days before the splenocyte fusion, and 50 μg/mice of antigen prepared in saline solution was intraperitoneally injected (IP).

2.2 Splenocyte Fusion

Hybridoma cells were obtained by fusing spleen lymphocytes with myeloma Sp2/0 cells (ATCC® CRL-8287™) with optimized PEG-mediated fusion procedure. The fused hybridoma cells were resuspended in complete medium (DMEM medium containing 20% FBS, 1×HAT, 1×OPI) at a density of 0.5-1×10^6/ml, and were seeded in 96-well plate with 100 μl/well. After incubation at 37° C., 5% CO$_2$ for 3-4 days, HAT complete medium was supplemented with 100 μl/well, and cultivated for another 3-4 days until needle-like clones were formed. The supernatant was removed, and 200 μl/well of HT complete medium (RPMI-1640 medium containing 20% FBS, 1×HT and 1×OPI) was added, and cultivated at 37° C., 5% CO$_2$ for 3 days, and the detection was then performed via ELISA.

2.3 Screening of Hybridoma Cells

Hybridoma culture supernatants were detected with binding ELISA according to the growth density of hybridoma cells. The supernatants for which cells were detected being positive by binding ELISA were subjected to cell binding assay and cell blocking assay. The wells in which cells were detected being positive both for the binding assay and blocking assay were expanded timely, cryopreserved and were subjected to subclones two to three time until a single cell clone was obtained.

Each subcloned cell was also subjected to TIGIT binding ELISA, HTRF blocking assay, cell binding assay and cell blocking assay. The hybridoma clones were obtained by the above experiments, the antibodies were further prepared by serum-free cell culture and purified according to the purification example, for use in the test examples.

2.4 Sequencing the Positive Hybridoma Clones

The positive hybridoma clones were sequenced as follows. The hybridoma cells at logarithmic growth phase were collected, RNAs were extracted with TRIzol™ (Invitrogen, Cat No. 15596-018) according to the manufacturer's instructions, and reverse transcription was performed with PrimeScript™ Reverse Transcriptase kit (Takara, Cat No. 2680A). The cDNAs obtained by reverse transcription were amplified via PCR with mouse Ig-Primer Set (Novagen, TB326 Rev. B 0503) and were sequenced. From the obtained DNA sequences, the amino acid sequences of the variable regions of the antibody corresponding to positive clone m17 were as follows:

m1707-HCVR
SEQ ID NO: 5
EVKLVESGGGLVQPGGSLKLSCAASGFIFSDYHMYWVRQTPEKRLEWVAY
ISKGGISTYYPDTVKGRFTISRDNAKHTLYLQMSRLKSEDTAMYYCARQS
SYDFAMDYWGRGTSVTVSS m1707-LCVR
SEQ ID NO: 6
DIVMTQSHKFMSTSVGVRVSITCKASQDVGTSVAWYQQKPGQSPKLLIYW
ASARHTGVPDRFTGSGSGTDFTLTITNVQSEDLADYFCQQYSSYPLTFGA
GTKLELK m1708-HCVR
SEQ ID NO: 7
QVQLQQPGAELVKPGSSVKLSCKASGYTFTNYWMHWVKQGPGRGLEWIGR
IDPDSTGSKYNEKFKTKASLTVDTVSGTAYMQLSSLTSEDSAVYFCAREG
AYGY m1708-LCVR
SEQ ID NO: 8
DIQMTQSPASLSASVGETVTITCRASENIYSYLAWYQQKQGKSPQLLVYN
ARTLAESVPSRFSGSGSGTQFSLKINSLQPEDFGSYYCQYHSGSPLPFGA
GTKLALK m1709-HCVR
SEQ ID NO: 9
EVQLQQSGPVLVKPGPSVKISCKASGFTFTDYYMHWVKQSLGKSLEWIGL
VYPYNDNTGYNRKFKGKATLTVDTSSSTAYIELNSLTSEDSAVYYCARGG
PSNWNYFDYWGQGTTLTVSS m1709-LCVR
SEQ ID NO: 10
DIVMTQSQKFMSTTVGDRVSITCKASQNVVTAVAWYQQKPGQSPKLLIYS
ASNRYTGVPDRFTGSGSGTDFTLTINNVQSEDLADYFCQQYTLYPLTFGA
GTKLELK m1710-HCVR
SEQ ID NO: 11
QVQLQQPGAELVKFGASVKLSCKASGYTFTNYYMHWVKQRPGRGLEWIGR
IDPTSGATKYNDNFKGKATLTVDKPSTTAYMQLSSLTSEDSAVYYCAREG
GFGYYFDYWGQGTTLTVSS m1710-LCVR
SEQ ID NO: 12
DIQMTQSPASLSASVGETVTITCRTSENIFTYLAWYQQKQGKSPQLLVYN
AKTFAEGVPSRFSGSGSGTQFSLKISSLQPEDFGIYYCQHHYGIPLPFGA
GTKLELK m1711-HCVR
SEQ ID NO: 13
QVQLQQSGTELVRPGTSVKMSCKASGYTFTNYWIGWAKQRPGHGLEWIGD
IYPGGAYTNYNEKFKDKATLTADKSSSTAYMQFSSLTSEDSAIYYCTRGD
YYDSSGRAMDYWGQGTSVTVSS m1711-LCVR
SEQ ID NO: 14
DIVMSQSPSSLAVSVGEKVSMSCKSSQSLLYSRNQMNYLAWYQQKPGQSP
KLLIYWTSTRESGVPDRFTGSGSGTDFTLTISSVKAEDLAVYYCQQYYSY
PYTFGGGTKLEIK

The CDR sequences in the light and heavy chains of each antibody are shown in Table 1.

TABLE 1

CDR sequences of each heavy chain and light chain

| Antibody | | Heavy chain | | Light chain | |
|---|---|---|---|---|---|
| m1707 | HCDR1 | DYHMY SEQ ID NO: 15 | LCDR1 | KASQDVGTSVA SEQ ID NO: 18 |
| | HCDR2 | YISKGGISTYYPDTVKG SEQ ID NO: 16 | LCDR2 | WASARHT SEQ ID NO: 19 |
| | HCDR3 | QSSYDFAMDY SEQ ID NO: 17 | LCDR3 | QQYSSYPLT SEQ ID NO: 20 |
| m1708 | HCDR1 | NYWMH SEQ ID NO: 21 | LCDR1 | RASENIYSYLA SEQ ID NO: 24 |
| | HCDR2 | RIDPDSTGSKYNEKFKT SEQ ID NO: 22 | LCDR2 | NARTLAE SEQ ID NO: 25 |
| | HCDR3 | EGAYGYYFDY SEQ ID NO: 23 | LCDR3 | QYHSGSPLP SEQ ID NO: 26 |
| m1709 | HCDR1 | DYYMH SEQ ID NO: 27 | LCDR1 | KASQNVVTAVA SEQ ID NO: 30 |
| | HCDR2 | LVYPYNDNTGYNRKFKG SEQ ID NO: 28 | LCDR2 | SASNRYT SEQ ID NO: 31 |
| | HCDR3 | GGPSNWNYFDY SEQ ID NO: 29 | LCDR3 | QQYTLYPLT SEQ ID NO: 32 |

TABLE 1-continued

CDR sequences of each heavy chain and light chain

| Antibody | Heavy chain | | Light chain | |
|---|---|---|---|---|
| m1710 | HCDR1 | NYYMH<br>SEQ ID NO: 33 | LCDR1 | RTSENIFTYLA<br>SEQ ID NO: 36 |
| | HCDR2 | RIDPTSGATKYNDNFKG<br>SEQ ID NO: 34 | LCDR2 | NAKTFAE<br>SEQ ID NO: 37 |
| | HCDR3 | EGGFGYYFDY<br>SEQ ID NO: 35 | LCDR3 | QHHYGIPLP<br>SEQ ID NO: 38 |
| m1711 | HCDR1 | NYWIG<br>SEQ ID NO: 39 | LCDR1 | KSSQSLLYSRNQMNYLA<br>SEQ ID NO: 42 |
| | HCDR2 | DIYPGGAYTNYNEKFKD<br>SEQ ID NO: 40 | LCDR2 | WTSTRES<br>SEQ ID NO: 43 |
| | HCDR3 | GDYYDSSGRAMDY<br>SEQ ID NO: 41 | LCDR3 | QQYYSYPYT<br>SEQ ID NO: 44 |

Example 3: Humanization of Murine Anti-Human TIGIT Antibodies

By aligning to IMGT human antibody heavy and light chain variable region germline gene database using MOE software, heavy and light chain variable region germline genes, which have high identity to those of murine antibody, were selected as templates. The CDRs of the murine antibody were separately grafted onto the corresponding human derived template to form a variable region sequence in the order of FR1-CDR1-FR2-CDR2-FR3-CDR3-FR4. If necessary, the key amino acids in the backbone sequence were back-mutated to the amino acids corresponding to the murine antibody to ensure the original affinity, and the humanized anti-TIGIT monoclonal antibodies were obtained. The amino acid residues in the CDR regions were determined and annotated by the Kabat numbering system.

The light and heavy chain variable regions of the murine antibody were linked to the light and heavy chain constant regions of human antibody to form a chimeric antibody, and the chimeric antibody corresponding to m1707 antibody was referred to as ch1707. As for the other antibodies, they were named in similar way.

3.1 Humanization of Hybridoma Clone m1707

(1) Selection of Frame for Humanization of m1707

For murine antibody m1707, the humanized light chain templates were IGKV1-39*02 and hjk2.1, and the humanized heavy chain templates were IGHV3-7*01 and hjh2. After humanization, the humanized antibody h1707 was obtained. The sequences of the humanized variable regions were as follows:

h1707 VH-CDR graft

SEQ ID NO: 45
*EVQLVESGGGLVQPGGSLRLSCAASGFTFS*DYHMY*WVRQAPGKGLEWVA*Y
ISKGGI*STYYPDTVKGRFTISRDNAKNSLYLQMNSLRAEDTAVYYCAR*QS
SYDFAMDY*WGRGTLVTVSS* h1707VL-CDR graft

SEQ ID NO: 46
*DIQMTQSPSFLSASVGDRVTITC*KASQDVGTSVA*WYQQKPGKAPKLLIY*W
ASARHT*GVPSRFSGSGSGTDFTLTISSLQPEDFATYYC*QQYSSYPLT*FGQ
GTKLEIK*

Note:
In the order of FR1-CDR1-FR2-CDR2-FR3-CDR3-FR4, the italic text shows the FR sequence, and the underlined text shows the CDR sequence.

(2) The Back Mutations for h1707 were Designed as Follows:

| h1707-VL | | h1707-VH | |
|---|---|---|---|
| h1707-L1 | Grafted | h1707-H1 | Grafted |
| h1707-L2 | S60D, T85D | h1707-H2 | N84S, S85R |
| h1707-L3 | S60D, T85D, A43S | | |
| h1707-L4 | S60D, T85D, A43S, S63T | | |

Note:
For example, S60D indicates that S on position 60 was back-mutated to D, according to the natural sequence numbering of the amino acid sequence. "Grafted" means that the murine antibody CDRs were grafted onto the human germline FR region sequence.

(3) Combinations of Humanized h1707 Sequences were as Follows:

| | h1707-H1 | h1707-H2 |
|---|---|---|
| h1707-L1 | h1707-01 | h1707-02 |
| h1707-L2 | h1707-03 | h1707-04 |
| h1707-L3 | h1707-05 | h1707-06 |
| h1707-L4 | h1707-07 | h1707-08 |

Note:
This table shows sequences obtained by combining various variants. For example, h1707-04 indicates that the humanized antibody h1707-04 comprises four back-mutations, i.e., light chain L2 and heavy chain H2. The others follow the same rule.

(4) The Specific Sequences of Humanized h1707 were as Follows:

>h1707-L1 (same as h1707 VL-CDR graft)

SEQ ID NO: 46
*DIQMTQSPSFLSASVGDRVTITC*KASQDVGTSVA*WYQQKPGKAPKLLIY*W
ASARHT*GVPSRFSGSGSGTDFTLTISSLQPEDFATYYC*QQYSSYPLT*FGQ
GTKLEIK*

>h1707-L2

SEQ ID NO: 47
*DIQMTQSPSFLSASVGDRVTITC*KASQDVGTSVA*WYQQKPGKAPKLLIY*W
ASARHT*GVPDRFSGSGSGTDFTLTISSLQPEDFADYYC*QQYSSYPLT*FGQ
GTKLEIK*

>h1707-L3

SEQ ID NO: 48
*DIQMTQSPSFLSASVGDRVTITC*KASQDVGTSVA*WYQQKPGKSPKLLIY*W
ASARHT*GVPDRFSGSGSGTDFTLTISSLQPEDFADYYC*QQYSSYPLT*FGQ
GTKLEIK*

>h1707-L4

SEQ ID NO: 49
*DIQMTQSPSFLSASVGDRVTITC*KASQDVGTSVA*WYQQKPGKSPKLLIY*W
ASARHT*GVPDRFTGSGSGTDFTLTISSLQPEDFADYYC*QQYSSYPLT*FGQ
GTKLEIK*

\>h1707-H1 (same as h1707 VH-CDR graft)

SEQ ID NO: 45

*EVQLVESGGGLVQPGGSLRLSCAASGFTFS*DYHMY*WVRQAPGKGLEWVAY*
ISKGGISTYYPDTVKG*RFTISRDNAKNSLYLQMNSLRAEDTAVYYCAR*QS
SYDFAMDY*WGRGTLVTVSS*

\>h1707-H2

SEQ ID NO: 50

*EVQLVESGGGLVQPGGSLRLSCAASGFTFS*DYHMY*WVRQAPGKGLEWVAY*
ISKGGISTYYPDTVKG*RFTISRDNAKNSLYLQMSRLAEDTAVYYCAR*QS
SYDFAMDY*WGRGTLVTVSS*

3.2 Humanization of Hybridoma Clone m1708

(1) Selection of Frame for Humanization of m1708

For murine antibody m1708, the humanized light chain templates were IGKV1-39*01 and hjk4.1, and the humanized heavy chain templates were IGHV1-46*01 and hjh4.1. After humanization, the humanized antibody h1708 was obtained. The sequences of the humanized variable regions were as follows:

h1708VH-CDR graft

SEQ ID NO: 51

*EVQLVQSGAEVKKPGASVKVSCKASGYTFT*NYWMH*WVRQAPGQGLEWMGR*
IDPDSTGSYNEKFKT*RVTMTRDTSTSTVYMELSSLRSEDTAVYYCAR*EG
AYGYYFDY*WGQGTLVTVSS* h1708VL-CDR graft

SEQ ID NO: 52

*DIQMTQSPSSLSASVGDRVTITC*RASENIYSYLA*WYQQKPGKAPKLLIY*N
ARTLAE*GVPSRFSGSGSGTDFTLTISSLQPEDFATYYC*QYHSGSPLP*FGG
GTKVEIK*

Note: In the order of FR1-CDR1-FR2-CDR2-FR3-CDR3-FR4, the italic text shows the FR sequence, and the underlined text shows the CDR sequence.

(2) The Back Mutations for h1708 were Designed as Follows:

| h1708-VL | | h1708-VH | |
|---|---|---|---|
| h1708-L1 | Grafted | h1708-H1 | Grafted |
| h1708-L2 | A43S | h1708-H2 | R72V |
| | | h1708-H3 | M48I, R72V, V79A |

Note:
For example, A43S indicates that A on position 43 was back-mutated to S, according to the natural sequence numbering of the amino acid sequence. "Grafted" means the murine antibody CDRs were grafted onto the human germline FR region sequence.

(3) Combinations of Humanized h1708 Sequences were as Follows:

| | h1708-H1 | h1708-H2 | h1708-H3 |
|---|---|---|---|
| h1708-L1 | h1708-01 | h1708-02 | h1708-03 |
| h1708-L2 | h1708-04 | h1708-05 | h1708-06 |

Note:
This table shows sequences obtained by combining various variants. For example, h1708-05 indicates that the humanized antibody h1708-05 comprises two back-mutations, i.e., light chain L2 and heavy chain H2. The others follow the same rule.

(4) The Specific Sequences of Humanized h1708 were as Follows:

\>h1708-L1 (same as h1708 VL-CDR graft)

SEQ ID NO: 52

*DIQMTQSPSSLSASVGDRVTITC*RASENIYSYLA*WYQQKPGKAPKLLIY*N
ARTLAE*GVPSRFSGSGSGTDFTLTISSLQPEDFATYYC*QYHSGSPLP*FGG
GTKVEIK*

\>h1708-L2

SEQ ID NO: 53

*DIQMTQSPSSLSASVGDRVTITC*RASENIYSYLA*WYQQKPGKSPKLLIY*N
ARTLAE*GVPSRFSGSGSGTDFTLTISSLQPEDFATYYC*QYHSGSPLP*FGG
GTKVEIK*

\>h1708-H1 (same as h1708 VH-CDR graft)

SEQ ID NO: 51

*EVQLVQSGAEVKKPGASVKVSCKASGYTFT*NYWMH*WVRQAPGQGLEWMGR*
IDPDSTGSYNEKFKT*RVTMTRDTSTSTVYMELSSLRSEDTAVYYCAR*EG
AYGYYFDY*WGQGTLVTVSS*

\>h1708-H2

SEQ ID NO: 54

*EVQLVQSGAEVKKPGASVKVSCKASGYTFT*NYWMH*WVRQAPGQGLEWMGR*
IDPDSTGSYNEKFKT*RVTMTVDTSTSTVYMELSSLRSEDTAVYYCAR*EG
AYGYYFDY*WGQGTLVTVSS*

\>h1708-H3

SEQ ID NO: 55

*EVQLVQSGAEVKKPGASVKVSCKASGYTFT*NYWMH*WVRQAPGQGLEWIGR*
IDPDSTGSYNEKFKT*RVTMTVDTSTSTAYMELSSLRSEDTAVYYCAR*EG
AYGYYFDY*WGQGTLVTVSS*

3.3 Humanization of Hybridoma Clone m1709

(1) Selection of Frame for Humanization of m1709

For murine antibody m1709, the humanized light chain templates were IGKV1-39*01 and hjk4.1, and the humanized heavy chain templates were IGHV1-46*01 and hjh4.1. After humanization, the humanized antibody h1709 was obtained. The sequences of the humanized variable regions were as follows:

h1709VH-CDR graft

SEQ ID NO: 56

*EVQLVQSGAEVKKPGASVKVSCKASGYTFT*DYYMH*WVRQAPGQGLEWMGL*
VYPYNDNTGYNRKFKG*RVTMTRDTSTSTVYMELSSLRSEDTAVYYCAR*GG
PSNWNYFDY*WGQGTLVTVSS* h1709VL-CDR graft

SEQ ID NO: 57

*DIQMTQSPSSLSASVGDRVTITC*KASQNVVTAVA*WYQQKPGKAPKLLIY*S
ASNRYTG*VPSRFSGSGSGTDFTLTISSLQPEDFATYYC*QQYTLYPLT*FGG
GTKVEIK*

Note:
In the order of FR1-CDR1-FR2-CDR2-FR3-CDR3-FR4, the italic text shows the FR sequence, and the underlined text shows the CDR sequence.

(2) The Back Mutations for h1709 were Designed as Follows:

| h1709-VL | | h1709-VH | |
|---|---|---|---|
| h1709-L1 | Grafted | h1709-H1 | Grafted |
| h1709-L2 | S60D | h1709-H2 | R72V, S84N |
| h1709-L3 | A43S, S60D, Y87F | h1709-H3 | R72V, V79A, S84N |
| h1709-L4 | Q3V, A43S, S60D, Y87F | h1709-H4 | Y27F, M48I, R72V, V79A, S84N |

Note:
For example, S60D indicates that S on position 60 was back-mutated to D, according to the natural sequence numbering of the amino acid sequence. "Grafted" means the murine antibody CDRs were grafted onto the human germline FR region sequence.

(3) Combinations of Humanized h1709 Sequences were as Follows:

|  | h1709-H1 | h1709-H2 | h1709-H3 | h1709-H4 |
|---|---|---|---|---|
| h1709-L1 | h1709-01 | h1709-02 | h1709-03 | h1709-04 |
| h1709-L2 | h1709-05 | h1709-06 | h1709-07 | h1709-08 |
| h1709-L3 | h1709-09 | h1709-10 | h1709-11 | h1709-12 |
| h1709-L4 | h1709-13 | h1709-14 | h1709-15 | h1709-16 |

Note:
This table shows sequences obtained by combining various variants. For example, h1709-06 indicates that the humanized antibody h1709-06 comprises three back-mutations, i.e., light chain L2 and heavy chain H2. The others follow the same rule.

(4) The Specific Sequences of Humanized h1709 were as Follows:

\>h1709-L1 (same as h1709 VL-CDR graft)
SEQ ID NO: 57
*DIQMTQSPSSLSASVGDRVTITC*KASQNVVTAVA*WYQQKPGKAPKLLIY*S
ASNRYT*GVPSRFSGSGSGTDFTLTISSLQPEDFATYYC*QQYTLYPLT*FGG
GTKVEIK*

\>h1709-L2
SEQ ID NO: 58
*DIQMTQSPSSLSASVGDRVTITC*KASQNVVTAVA*WYQQKPGKAPKLLIY*S
ASNRYT*GVPDRFSGSGSGTDFTLTISSLQPEDFATYYC*QQYTLYPLT*FGG
GTKVEIK*

\>h1709L3
SEQ ID NO: 59
*DIQMTQSPSSLSASVGDRVTITC*KASQNVVTAVA*WYQQKPGKSPKLLIY*S
ASNRYT*GVPDRFSGSGSGTDFTLTISSLQPEDFATYF*C*QQYTLYPLT*FGG
GTKVEIK*

\>h1709-L4
SEQ ID NO: 60
*DIVMTQSPSSLSASVGDRVTITC*KASQNVVTAVA*WYQQKPGKSPKLLIY*S
ASNRYT*GVPDRFSGSGSGTDFTLTISSLQPEDFATYFC*QQYTLYPLT*FGG
GTKVEIK*

\>h1709.H1 (same as h1709 VH-CDR graft)
SEQ ID NO: 56
*EVQLVQSGAEVKKPGASVKVSCKASGYTFT*DYYMH*WVRAPGQGLEWMGL*V
YPYNDNTGYNRKFKG*RVTMTRDTSTSTVYMELSSLRSEDTAVYYCAR*GGP
SNWNYFDY*WGQGTLVTVSS*

\>h1709-H2
SEQ ID NO: 61
*EVQLVQSGAEVKKPGASVKVSCKASGYTFT*DYYMH*WVRQAPGQGLEWMGL*
VYPYNDNTGYNRKFKG*RVTMTVDTSTSTVYMELNSLRSEDTAVYYCAR*GG
PSNWNYFDY*WGQGTLVTVSS*

\>h1709-H3
SEQ ID NO: 62
*EVQLVQSGAEVKKPGASVKVSCKASGYTFT*DYYMH*WVRQAPGQGLEWMGL*
VYPYNDNTGYNRKFKG*RVTMTVDTSTSTAYMELNSLRSEDTAVYYCAR*GG
PSNWNYFDY*WGQGTLVTVSS*

\>h1709-H4
SEQ ID NO: 63
*EVQLVQSGAEVKKPGASVKVSCKASGFTFT*DYYMH*WVRQAPGQGLEWIGL*
VYPYNDNTGYNRKFKG*RVTMTVDTSTSTAYMELNSLRSEDTAVYYCAR*GG
PSNWNYFDY*GQGTLVTVSS*

3.4 Humanization of Hybridoma Clone m1710

(1) Selection of Frame for Humanization of m1710

For murine antibody m1710, the humanized light chain templates were IGKV1-39*01 and hjk4.1, and the humanized heavy chain templates were IGHV1-46*01 and hjh4.1. After humanization, the humanized antibody h1710 was obtained. The sequences of the humanized variable regions were as follows:

h1710VH-CDR graft
SEQ ID NO: 64
*EVQLVQSGAEVKKPGASVKVSCKASGYTFT*NYYMH*WVRQAPGQGLEWMGR*
IDPTSGATKYNDNFKG*RVTMTRDTSTSTVYMELSSLRSEDTAVYYCAR*EG
GFGYYFDY*WGQGTTVTVSS* h1710VL-CDR graft
SEQ ID NO: 65
*DIQMTQSPSSLSASVGDRVTITC*RTSENIFTYLA*WYQQKPGKAPKLLIY*N
AKTFAE*GVPSRFSGSGSGTDFTLTISSLQPEDFATYYC*QHHYGIPLPF*GQ
GTKLEIK*

Note:
In the order of FR1-CDR1-FR2-CDR2-FR3-CDR3-FR4, the italic text shows the FR sequence, and the underlined text shows the CDR sequence.

(2) The Back Mutations for h1710 were Designed as Follows:

| h1710-VL | | h1710-VH | |
|---|---|---|---|
| h1710-L1 | Grafted | h1710-H1 | Grafted |
| h1710-L2 | A43S, I48V | h1710-H2 | R72V, T74K |
|  |  | h1710-H3 | R72V, T74K, M70L, V79A |
|  |  | h1710-H4 | R72V, T74K, M48I, V68A, M70L, V79A |
|  |  | h1710-H5 | R38K, R67K, R72V, T74K, M48I, V68A, M70L, V79A |

Note:
For example, A43S indicates that A on position 43 was back-mutated to S, according to the natural sequence numbering of the amino acid sequence. "Grafted" means the murine antibody CDRs were grafted onto the human germline FR region sequence.

(3) Combinations of Humanized h1710 Sequences were as Follows:

|  | h1710-H1 | h1710-H2 | h1710-H3 | h1710-H4 | h1710-H5 |
|---|---|---|---|---|---|
| h1710-L1 | h1710-01 | h1710-02 | h1710-03 | h1710-04 | h1710-05 |
| h1710-L2 | h1710-06 | h1710-07 | h1710-08 | h1710-09 | h1710-10 |

Note:
This table shows sequences obtained by combining various variants. For example, h1710-07 indicates that the humanized antibody h1710-07 comprises four back-mutations, i.e., light chain L2 and heavy chain H2. The others follow the same rule.

(4) The Specific Sequences of Humanized h1710 were as Follows:

\>h1710-L1 (same as h1710 VL-CDR graft)
SEQ 1D NO: 65
*DIQMTQSPSSLSASVGDRVTITC*RTSENIFTYLA*WYQQKPGKLLI*YNAKT
FAE*GVPSRFSGSGSGTDFTLTISSLQPEDFATYYC*QHHYGIPLPF*GQGTK
LEIK*

\>h1710-L2
SEQ ID NO: 66
*DIQMTQSPSSLSASVGDRVTITC*RTSENIFTYLA*WYQQKPGKSPKLLVY*N
AKTFAE*GVPSRFSGSGSGTDFTLTISSLQPEDFATYYC*QHHYGIPLPF*GQ
GTKLEIK*

\>h1710-H1 (same as h1710 VH-CDR graft)
SEQ ID NO: 64
*EVQLVQSGAEVKKPGASVKVSCKASGYTFT*NYYMH*WVRQAPGQGLEWMGR*
IDPTSGATKYNDNFKG*RVTMTRDTSTSTVYMELSSLRSEDTAVYYCAR*EG
GFGYYFDY*WGQGTTVTVSS*

\>h1710-H2
SEQ ID NO: 67
*EVQLVQSGAEVKKPGASVKVSCKASGYTFT*NYYMH*WVRQAPGQGLEWMGR*
IDPTSGATKYNDNFKG*RVTMTVDKSTSTVYMELSSLRSEDTAVYYCAR*EG
GFGYYFDY*WGQGTTVTVSS*

>h1710-H3
SEQ ID NO: 68
EVQLVQSGAEVKKPGASVKVSCKASGYTF<u>TNYYMH</u>WVRQAPGQGLEWMG<u>R</u>
<u>IDPTSGATKYNDNFKG</u>RVTLTVDKSTSTAYMELSSLRSEDTAVYYCAR<u>EG</u>
<u>GFGYYFDY</u>WGQGTTVTVSS

>h1710-H4
SEQ ID NO: 69
EVQLVQSGAEVKKPGASVKVSCKASGYTF<u>TNYYMH</u>WVRQAPGQGLEWIG<u>R</u>
<u>IDPTSGATKYNDNFKG</u>RATLTVDKSTSTAYMELSSLRSEDTAVYYCAR<u>EG</u>
<u>GFGYYFDY</u>WGQGTTVTVSS

>h1710-H5
SEQ ID NO: 70
EVQLVQSGAEVKKPGASVKVSCKASGYTF<u>TNYYMH</u>WVKQAPGQGLEWIG<u>R</u>
<u>IDPTSGATKYNDNFKG</u>KATLTVDKSTSTAYMELSSLRSEDTAVYYCAR<u>EG</u>
<u>GFGYYFDY</u>WGQGTTVTVSS

3.5 Humanization of Hybridoma Clone m1711

(1) Selection of Frame for Humanization of m1711

For murine antibody m1711, the humanized light chain templates were IGKV4-1*01 and hjk4.1, and the humanized heavy chain templates were IGHV1-69*02 and hjh4.1. After humanization, the humanized antibody h1711 was obtained. The sequences of the humanized variable regions were as follows:

h1711VH-CDR graft
SEQ ID NO: 71
EVQLVQSGAEVKKPGSSVKVSCKASGGTFS<u>NYWIG</u>WVRQAPGQGLEWMG<u>D</u>
<u>IYPGGAYTNYNEKFKD</u>RVTITADKSTSTAYMELSSLRSEDTAVYYCAR<u>GD</u>
<u>YYDSSGRAMDY</u>WGQGTLVTV h1711VL-CDR graft
SEQ ID NO: 72
DIVMTQSPDSLAVSLGERATINC<u>KSSQSLLYSRNQMNYLA</u>WYQQKPGQPP
KLLIY<u>WTSTRES</u>GVPDRFSGSGSGTDFTLTISSLQAEDVAVYYC<u>QQYYSY</u>
<u>PYT</u>FGGGTKVEIK
Note:
In the order of FR1-CDR1-FR2-CDR2-FR3-CDR3-FR4, the italic text shows FR sequence, and the underlined text shows CDR sequence.

(2) The Back Mutations for h1711 were Designed as Follows:

| | h1711-VL | | h1711-VH |
|---|---|---|---|
| h1711-L1 | Grafted | h1711-H1 | Grafted |
| h1711-L2 | P49S | h1711-H2 | M48I, |
| h1711-L3 | N22S, P49S | h1711-H3 | G27Y, M48I, |
| | | h1711-H4 | G27Y, M48I, L83F, A97T |

Note:
For example, P49S indicates that P on position 49 was back-mutated to S, according to the natural sequence numbering of the amino acid sequence. "Grafted" means the murine antibody CDRs were grafted onto the human germline FR region sequence.

(3) Combinations of Humanized h1711 Sequences were as Follows:

| | h1711-H1 | h1711-H2 | h1711-H3 | h1711-H4 |
|---|---|---|---|---|
| h1711-L1 | h1711-01 | h1711-02 | h1711-03 | h1711-04 |
| h1711-L2 | h1711-05 | h1711-06 | h1711-07 | h1711-08 |
| h1711-L3 | h1711-09 | h1711-10 | h1711-11 | h1711-12 |

Note:
This table shows sequences obtained by combining various variants. For example, h1711-06 indicates that the humanized antibody h1711-06 comprises back-mutations consisting of light chain L2 and heavy chain H2. The others follow the same rule.

(4) The Specific Sequences of Humanized h1711 were as Follows:

>h1711-L1 (same as h1711 VL-CDR graft)
SEQ ID NO: 72
DIVMTQSPDSLAVSLGERATINC<u>KSSQSLLYSRNQMNYLA</u>WYQQKPGQPP
KLLIY<u>WTSTRES</u>GVPDRFSGSGSGTDFTLTISSLQAEDVAVYYC<u>QQYYSY</u>
<u>PYT</u>FGGGTKVEIK >h1711-L2
SEQ ID NO: 73
DIVMTQSPDSLAVSLGERATINC<u>KSSQSLLYSRNQMNYLA</u>WYQQKPGQSP
KLLIY<u>WTSTRES</u>GVPDRFSGSGSGTDFTLTISSLQAEDVAVYYC<u>QQYYSY</u>
<u>PYT</u>FGGGTKVEIK >h1711-L3
SEQ ID NO: 74
DIVMTQSPDSLAVSLGERATISC<u>KSSQSLLYSRNQMNYLA</u>WYQQKPGQSP
KLLIY<u>WTSTRES</u>GVPDRFSGSGTDFTLTISSLQAEDVAVYYC<u>QQYYSYPY</u>
<u>T</u>FGGGTKVEIK >h1711-H1 (same as h1711 VH-CDR graft)
SEQ ID NO: 71
EVQLVQSGAEVKKPGSSVKVSCKASGGTFS<u>NYWIG</u>WVRQAPGQGLEWMG<u>D</u>
<u>IYPGGAYTNYNEKFKD</u>RVTITADKSTSTAYMELSSLRSEDTAVYYCAR<u>GD</u>
<u>YYDSSGRAMDY</u>WGQGTLVTVSS >h1711-H2
SEQ ID NO: 75
EVQLVQSGAEVKKPGSSVKVSCKASGGTFS<u>NYWIG</u>WVRQAPGQGLEWIG<u>D</u>
<u>IYPGGAYTNYNEKFKD</u>RVTITADKSTSTAYMELSSLRSEDTAVYYCAR<u>GD</u>
<u>YYDSSGRAMDY</u>WGQGTLVTVSS >h1711-H3
SEQ ID NO: 76
EVQLVQSGAEVKKPGSSVKVSCKASGYTFS<u>NYWIG</u>WVRQAPGQGLEWIG<u>D</u>
<u>IYPGGAYTNYENKFKD</u>RVTITADKSTSTAYMELSSLRSEDTAVYYCAR<u>GD</u>
<u>YYDSSGRAMDY</u>WGQGTLVTVSS >h1711-H4
SEQ ID NO: 77
EVQLVQSGAEVKKPGSSVKVSCKASGYTS<u>NYWIG</u>WVRQAPGQGLEWIG<u>DI</u>
<u>YPGGAYTNYNEKFKD</u>RVTITADKSTSTAYMEFSSLRSEDTAVYYCTR<u>GDY</u>
<u>YDSSGRAMDY</u>WGQGTLVTVSS A full-length heavy chain sequence was obtained by recombinantly expressing each of the above heavy chain variable regions with the heavy chain constant region sequence (IgG4, with S228P mutation) as set forth in SEQ ID NO: 78. Each of the above light chain variable regions is recombinantly expressed with the light chain constant region sequence (kappa chain) as set forth in SEQ ID NO: 79 to form the final full-length light chain sequence. The heavy and light chain variable regions described above can also be recombined with other IgG family heavy and light chain constant regions or mutated IgG family constant regions well known in the art to form intact antibody heavy and light chain sequences. Exemplary constant region sequences are shown as follows:

IgG4 heavy chain constant region with S228P mutation:
SEQ ID NO: 78
ASTKGPSVFPLAPCSRSTSESTALLGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK

```
-continued
CKVSNKGLPSSIEKTISKAKGQPREPQVYTLPSQEEMTKNQVSLTCLVKG

FYPSDIAVEWESNGQPENNYKTTPPVLDSDGSFFLYSRLTVDKSRWQEGN

VFSCSVMHEALHYHYTQKSLSLSLGK

Light chain constant region:
                                          SEQ ID NO: 79
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

The above light and heavy chains were recombinantly expressed with the alternative humanized constant region of the present disclosure or with the functionally-modified humanized constant region, by conventional techniques in the art.

22G2-H3Q was used as positive control antibody, its VH and VL sequences were derived from US20160176963A1 (SEQ ID NOs: 8 and 9 of US20160176963A1, respectively), and were linked to the heavy and light chain constant region of SEQ ID NO: 78 and SEQ ID NO: 79, respectively to form an intact full-length antibody. The specific sequences of VH and VL of 22G2-H3Q are shown as follows:

```
22G2-H3Q VH
                                          SEQ ID NO: 80
QVQLQESGPGLVKPSETLSLTCTVSGGSVSSGIYYWSWIRQPPGKGLEWI
GYIYYSGNTNYNPSLKSRVTISVDTSKNQFSLKLSSVTAADTAVYYCARD
YYVSGNYYNVDYYFFGVDVWGQGTTVTVSS

22G2-H3Q VL
                                          SEQ ID NO: 81
EIVLTQSPATLSLSPGERATLSCRASQSVSSYLAWYQQKPGQAPRLLIYD
ASNRATGIPARFSGSGSGTDFTLTISSLEPEDFAVYYCQQRSNWPPLFTF
GPGTKVDIK
```

The binding activities of the present disclosure were demonstrated with the following biochemical tests.

Test Example 1: The Binding of TIGIT Antibodies to Human TIGIT Protein by ELISA Assay The binding capacity of anti-TIGIT antibodies was detected using the antibodies and the human TIGIT protein by ELISA assay. The TIGIT fusion protein with Fc or mFc tag was immobilized onto a 96-well microtiter plate by binding to anti-Fc or mFc antibody coated on the ELISA plate. The signal intensity after addition of the antibody was used to determine the binding activity of the antibody to TIGIT. 10A7 hIgG4 (the light and heavy chain variable region sequence of which were derived from SEQ ID NOs: 21 and 22 disclosed in US20130251720A1, and the above light and heavy chain variable regions were linked to the light and heavy chain constant region of SEQ ID NOs: 79 and 78 of the present disclosure respectively, to form a full-length antibody) was used as positive control molecule, human IgG4 antibody (hIgG4) was used as negative control, which was incapable of binding to TIGIT. Particularly, the experimental procedure was described as follows:

Goat anti-human Fc antibody (Jackson Immuno Research, Cat No. 109-005-008) or goat anti-mouse Fc antibody (Sigma, Cat No. M3534-1ML) was diluted with PBS, pH 7.4 (Shanghai BasalMedia, Cat No. B320) to a concentration of 2 μg/ml, added into 96-well microtiter plate (Corning, Cat No. CLS3590-100EA) at a volume of 50 μl/well, and placed in an incubator at 37° C. for 2 hours. After discarding the liquid, 5% skim milk (BD skim milk, Cat No. 232100) blocking solution diluted with PBS was added at 200 μl/well, incubated at 37° C. for 3 hours or at 4° C. overnight (16-18 hours) for blocking. After blocking was finished, the blocking solution was discarded, the plate was washed 5 times with PBST buffer (PBS containing 0.05% Tween 20™, pH 7.4), TIGIT-Fc fusion protein (produced in-house) or TIGIT-mFc fusion protein (produced in-house) diluted with sample dilution solution (PBS containing 1% BSA, pH 7.4) to a concentration of 0.5 μg/ml was added at 50 μl/well, and placed in the incubator at 37° C. for 1 hour or at 4° C. overnight. After the incubation, the reaction solution was removed from the plate, the plate was washed with PBST for 5 times, the antibodies to be tested (hybridoma purified antibody or humanized antibody) diluted with sample dilution solution to various concentrations were added at 50 μl/well, and placed in the incubator at 37° C. for 1 hour. After the incubation, the plate was washed 5 times with PBST, HRP-labeled goat anti-mouse secondary antibody (Jackson Immuno Research, Cat No. 115-035-003) or goat anti-human secondary antibody (Jackson Immuno Research, Cat No. 109-035-003) diluted with sample dilution solution was added at 50 μl/well, and incubated at 37° C. for 1 hour. The plate was washed with PBST for 5 times, TMB chromogenic substrate (KPL, Cat No. 52-00-03) was added at 50 μl/well, incubated at room temperature for 5-10 min, and 50 μl/well of 1M H2SO4 was added to terminate the reaction. The absorbance at a wavelength of 450 nm was read with microplate reader (Thermo scientific Multiskan, MK3). Data were analyzed with GraphPad Prism 5, EC50 value was calculated as the binding of the TIGIT antibody to human TIGIT protein. The results are shown in FIG. 1.

Figure 2:
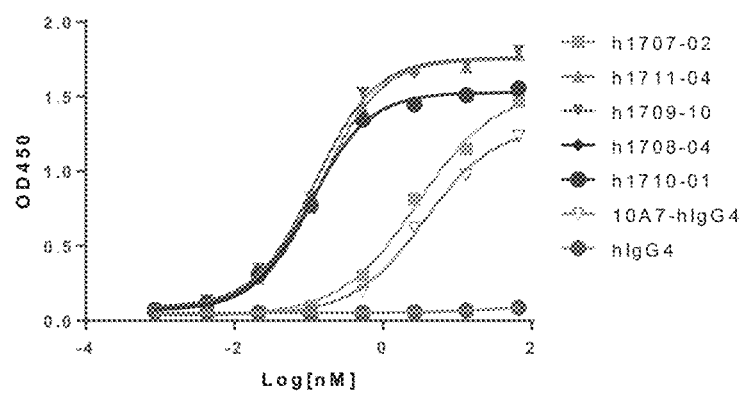
FIG. 2: Detection of the binding of TIGIT antibodies to monkey TIGIT protein by ELISA assay.

Test Example 2: The Binding of TIGIT Antibodies to Cynomolgus TIGIT Protein by ELISA Assay The cross-binding capacity of anti-TIGIT antibodies to monkey protein was detected using the antibodies and the cynomolgus TIGIT protein by ELISA assay. The cynomolgus TIGIT fusion protein with Fc or mFc tag was immobilized onto a 96-well microtiter plate by binding to anti-Fc or mFc antibody coated on the ELISA plate. The signal intensity after addition of the antibody was used to determine the binding activity of the antibody to cynomolgus TIGIT. Particularly, the experimental procedure was described as follows:

Goat anti-human Fc antibody (Jackson Immuno Research, Cat No. 109-005-008) or goat anti-mouse Fc antibody (Sigma, Cat No. M3534-1ML) was diluted with PBS, pH 7.4 (Shanghai BasalMedia, Cat No. B320) to a concentration of 2 μg/ml, added into 96-well microtiter plate (Corning, Cat No. CLS3590-100EA) at a volume of 50 μl/well, and the plate was placed in an incubator at 37° C. for 2 hours. After discarding the liquid, 5% skim milk (BD skim milk, Cat No. 232100) blocking solution diluted with PBS was added at 200 μl/well, incubated at 37° C. for 3 hours or at 4° C. overnight (16-18 hours) for blocking. After blocking was finished, the blocking solution was discarded, the plate was washed 5 times with PBST buffer (PBS containing 0.05% Tween 20™, pH 7.4), cynomolgus TIGIT-Fc fusion protein (produced in-house) or cynomolgus TIGIT-mFc fusion protein (produced in-house) diluted with sample dilution solution (PBS containing 1% BSA, pH 7.4) to a concentration of 0.5 μg/ml was added at 50 μl/well, and the plate was placed in the incubator at 37° C. for 1 hour or at 4° C. overnight. After the incubation, the reaction solution was removed from the plate, the plate was washed with PBST for 5 times, the antibodies to be tested (hybridoma purified antibody or humanized antibody) diluted with sample dilution solution to various concentrations were added at 50 μl/well, and the plate was placed in the incubator at 37° C. for 1 hour. After the incubation, the plate was washed 5 times with PBST, HRP-labeled goat anti-mouse secondary antibody (Jackson Immuno Research, Cat No. 115-035-003) or goat anti-human secondary antibody (Jackson Immuno Research, Cat No. 109-035-003) diluted with sample dilution solution was added at 50 μl/well, and incubated at 37° C. for 1 hour. The plate was washed with PBST for 5 times, 50 μl/well of TMB chromogenic substrate (KPL, Cat No. 52-00-03) was added, incubated at room temperature for 5-10 min, and 50 μl/well of 1M H2SO4 was added to terminate the reaction. The absorbance at a wavelength of 450 nm was read with microplate reader (Thermo scientific Multiskan, MK3). Data were analyzed with GraphPad Prism 5, EC50 value was calculated as the binding of the TIGIT antibody to cynomolgus TIGIT protein. The results are shown in FIG. 2.

Figure 3:
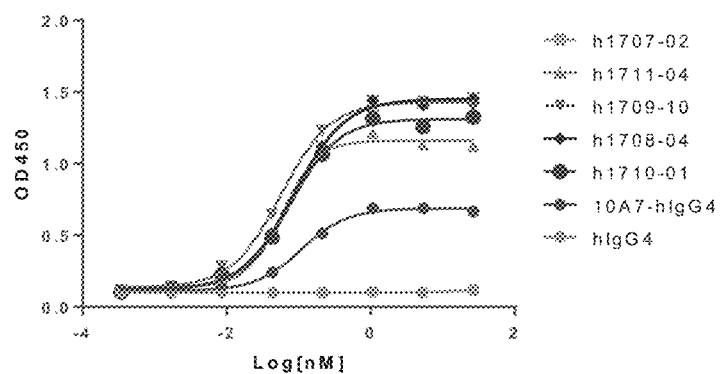
FIG. 3: Detection of the binding of TIGIT antibodies to CHO cells overexpressing human TIGIT.

Test Example 3: Binding of TIGIT Antibodies to CHO Cells Overexpressing Human TIGIT by Binding Assay The binding capacity of the anti-TIGIT antibodies was detected using the antibodies and the CHO cells overexpressing TIGIT protein by binding assay. The TIGIT full-length plasmid was transformed into CHO cells by electroporation, screened with pressure for two weeks, and the expression level of TIGIT was examined. The cells overexpressing TIGIT were fixed onto the bottom of a 96-well plate. The signal intensity after addition of the antibody was used to determine the binding activity of the antibody to the CHO cells overexpressing TIGIT. Particularly, the experimental procedure was described as follows:

The cells were seeded at a density of 5×10^5/ml, 100 μl/well was cultivated in 96-well plate overnight. The supernatant was discarded, the plate was washed three times with PBS, and then 100 μl/well of cell immunofixation solution (Beyotime, Cat No. P0098) was added for fixing the cells at room temperature for half an hour. The plate was washed with PBS four times. After discarding the liquid, 5% skim milk (BD skim milk, Cat No. 232100) blocking solution diluted with PBS was added at 200 μl/well, incubated at 37° C. for 3 hours for blocking. After blocking was finished, the blocking solution was discarded, the plate was washed 5 times with PBST buffer (PBS containing 0.05% Tween 20™, pH 7.4), the antibodies to be tested (hybridoma purified antibody or humanized antibody) diluted with sample dilution solution to various concentrations were added at 50 μl/well, and placed in the incubator at 37° C. for 1 hour. After the incubation, the plate was washed 5 times with PBST, HRP-labeled goat anti-mouse secondary antibody (Jackson Immuno Research, Cat No. 115-035-003) or goat anti-human secondary antibody (Jackson Immuno Research, Cat No. 109-035-003) diluted with sample dilution solution was added at 50 μl/well, and incubated at 37° C. for 1 hour. The plate was washed with PBST for 5 times, 50 μl/well of TMB chromogenic substrate (KPL, Cat No. 52-00-03) was added, incubated at room temperature for 5-15 min, and 50 μl/well of 1M H2SO4 was added to terminate the reaction. The absorbance at a wavelength of 450 nm was read with microplate reader (Thermo scientific Multiskan, MK3). Data were analyzed with GraphPad Prism 5, EC50 value was calculated as the binding of the TIGIT antibody to CHO cells overexpressing TIGIT protein. The results are shown in FIG. 3 and the following table.

| | antibody | | | | | | |
|---|---|---|---|---|---|---|---|
| | h1707-02 | h1711-04 | h1709-10 | h1708-04 | h1710-01 | 10A7-IgG4 | hIgG4 |
| EC50 (nM) | 0.08717 | 0.05868 | 0.05684 | 0.08480 | 0.07686 | 0.1090 | >10000 |

Test Example 4: Binding of TIGIT Antibodies to Human PBMC by Binding Assay

The binding activity of anti-TIGIT antibodies was detected using the antibodies and human PBMCs activated in vitro by binding assay. Human PBMCs were activated by the stimulation of superantigen S. aureus enterotoxin B (SEB). The fluorescent signal intensity after addition of the antibody was used to determine the binding activity of the antibody to the activated human PBMCs. Particularly, the experimental procedure was described as follows:

PBMCs were obtained from fresh blood by Ficoll®-Hypaque density gradient centrifugation (Stem Cell Technologies), and were cultivated in RPMI 1640 culture medium supplemented with 10% (v/v) FBS and 500 ng/ml superantigen S. aureus enterotoxin B. (SEB), at 37° C., 5% $CO_2$ for 4 days.

Figure 4:
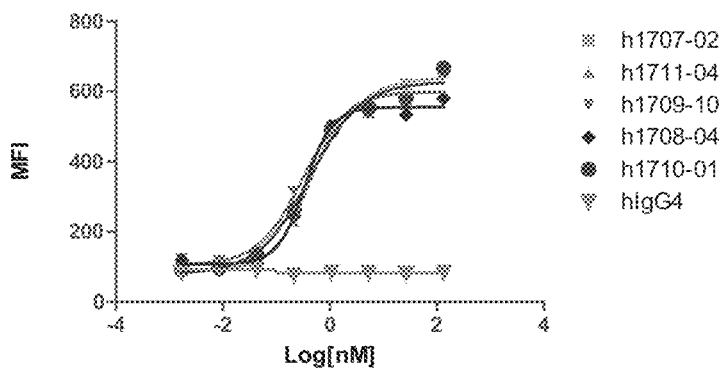
FIG. 4: Detection of binding affinity of TIGIT antibodies to human PBMC.

The activated PBMC cells were seeded at a density of 5×10^6/ml, 100 μl/well in a 96-well round bottom plate (Corning, Cat No. 32915001), and centrifuged at 1500 rpm for 5 minutes in a centrifuge (Beckman Coulter, Allegra® X-15R Centrifuge). The supernatant was discarded. The cells were resuspended with 200 μl PBS, and then centrifuged and the supernatant was discarded again. The cells were resuspended by adding 100 μl/well of the antibody to be tested which was diluted with gradient sample dilution solution (PBS containing 1% BSA, pH 7.4), and incubated at 4° C. for 1 hour. After the incubation, the sample was centrifuged at 1500 rpm for 5 minutes, the supernatant was discarded, the cells were washed twice with sample dilution solution and resuspended by adding 100 μl of PE-goat anti-human IgG (Jackson ImmunoResearch, 109-115-098) dilution solution, and incubated at 4° C. for 1 hour. After the incubation, the sample was centrifuged at 1500 rpm for 5 minutes, the supernatant was discarded, the cells were washed twice with sample dilution solution, and finally resuspended with 200 μl/well of sample dilution solution. The intensity of the fluorescence signal was measured on a flow cytometer (BD FACSCanto™ II). Data were analyzed by GraphPad Prism 5. EC50 value was calculated as the binding of the TIGIT antibody to human PBMCs. The results are shown in FIG. 4.

Test Example 5: Biacore™ Assay

The affinity of the humanized anti-TIGIT antibodies to be tested to human and monkey TIGIT was determined by using Biacore™, GE instrument.

Human anti-capture antibody was covalently coupled onto biosensor chip (Cat. #28-9538-28, GE) by affinity capture using Protein A biosensor chip (Cat. #29127556, GE) or according to the instructions provided by Human Anti-Capture Kit (Cat. #28-9538-28, GE), thereby a certain amount of the antibody to be tested was affinity captured. Then a series of concentration gradients of human and monkey TIGIT antigens were flowed through the surface of the chip. The human TIGIT was available from Sinobiological Co., Ltd. (Cat.10917-H08-H, Sino. Biol), and the monkey TIGIT was obtained from the expression and purification described in Example 1 and Example 2. The reaction signals were detected in real time by using Biacore™ instrument (Biacore™ T200, GE) to obtain binding and dissociation curves. After the dissociation of each cycle was completed, the biosensor chip was washed and regenerated with regeneration solution provided in the Human anti-Capture Kit or glycine-hydrochloric acid regeneration solution, pH 1.5 (Cat. #BR-1003-54, GE). The Amino Coupling Kit used in the experiment was purchased from GE (Cat. #BR-1000-50, GE) and the buffer was HBS-EP+10×buffer solution (Cat. #BR-1006-69, GE) and was diluted to 1×(pH 7.4) with D.I. Water.

The data was fitted to (1:1) Langmuir model by using BIAevaluation version 4.1, GE software, and the affinity values were obtained as shown in Tables 2-4.

TABLE 2

Reaction affinity of the molecule to be tested to huTIGIT protein

| Stationary Phase | Means for Immobilization | Mobile phase | Binding constant (1/Ms) | Dissociation constant (1/s) | Affinity (M) |
|---|---|---|---|---|---|
| 22G2-H3Q | Protein A capture | huTIGIT | 5.35E5 | 3.79E−4 | 7.09E−10 |
| h1707-02 | | | 1.74E6 | 1.88E−4 | 1.08E−10 |
| h1711-04 | | | 1.83E6 | 4.36E−4 | 2.38E−10 |
| h1709-10 | | | 2.49E6 | 2.59E−4 | 1.04E−10 |
| h1708-04 | | | 1.75E6 | 1.83E−4 | 1.04E−10 |
| h1710-01 | | | 1.63E6 | 2.40E−4 | 1.47E−10 |

TABLE 3

Reaction affinity of the molecule to be tested to cynoTIGIT protein

| Stationary Phase | Means for Immobilization | Mobile phase | Binding constant (1/Ms) | Dissociation constant (1/s) | Affinity (M) |
|---|---|---|---|---|---|
| 22G2-H3Q | Fc affinity capture | cynoTIGIT-mFc | 2.44E6 | 4.04E−4 | 1.66E−10 |
| h1711-04 | | | 2.46E6 | 3.17E−4 | 1.29E−10 |
| h1709-10 | | | 1.39E6 | 4.15E−4 | 3.00E−10 |
| h1708-04 | | | 1.24E6 | 3.52E−4 | 2.85E−10 |
| h1710-01 | | | 1.15E6 | 3.71E−4 | 3.22E−10 |

TABLE 4

Reaction affinity of ch1711 and its humanized antibodies to TIGIT protein

| | Biacore ™ (TIGIT-His) | | |
|---|---|---|---|
| Antibody | ka (1/Ms) | kd (1/s) | KD (M) |
| ch1711 | 1.83E6 | 4.55E−4 | 2.49E−10 |
| h1711-01 | 1.40E6 | 2.09E−3 | 1.49E−9 |
| h1711-02 | 1.38E6 | 1.71E−3 | 1.24E−9 |
| h1711-03 | 1.30E6 | 7.23E−4 | 5.56E−10 |
| h1711-04 | 2.10E6 | 4.42E−4 | 2.10E−10 |
| h1711-05 | 1.52E6 | 1.86E−3 | 1.22E−9 |
| h1711-06 | 1.46E6 | 1.52E−3 | 1.05E−9 |
| h1711-07 | 1.51E6 | 7.32E−4 | 4.85E−10 |
| h1711-08 | 2.13E6 | 4.41E−4 | 2.07E−10 |
| h1711-09 | 1.55E6 | 1.85E−3 | 1.19E−9 |
| h1711-10 | 1.47E6 | 1.52E−3 | 1.03E−9 |
| h1711-11 | 1.72E6 | 8.52E−4 | 4.94E−10 |
| h1711-12 | 2.10E6 | 4.31E−4 | 2.05E−10 |

Figure 5A:
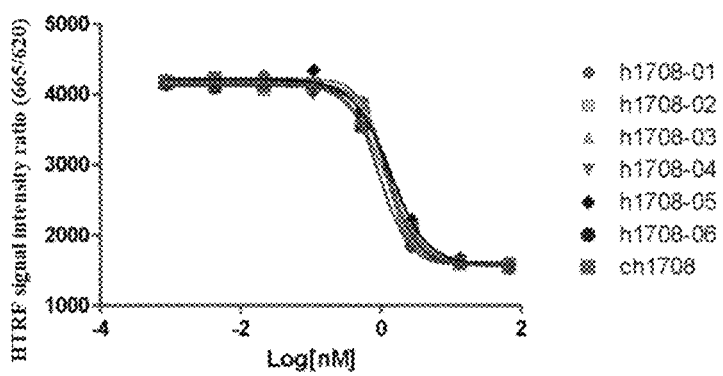
FIG. 5A: Detection of the effects of ch1708 and its humanized antibodies on blocking the binding of human TIGIT to CD155.
Figure 5B:
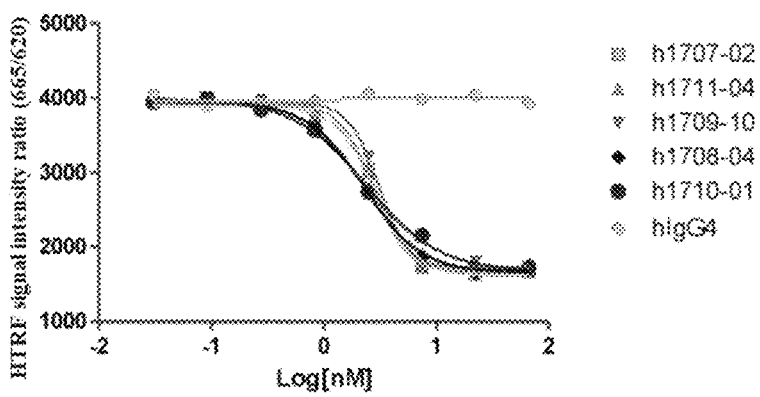
FIG. 5B: Detection of the effects of humanized TIGIT antibodies on blocking the binding of human TIGIT to CD155.

Test Example 6: TIGIT Antibodies Block the Binding of TIGIT Antigen to CD155 Protein by Blocking Assay The blocking ability of the anti-TIGIT antibodies was determined by HTRF assay in which the antibodies block the binding of TIGIT to CD155 protein. The pair of donor and receptor, Pab Anti-Human IgG-Tb (Cisbio, Cat No. 61HFCTAA) and Streptavidin-XL665 (Cisbio, Cat No. 610SAXLA), binds to TIGIT-Fc and biotinylated CD155 (R&D, Cat No. 2530-CD-050/CF). Alternatively, Pab Anti-mouse-IgG-XL665 (Cisbio, Cat No. 61PAMXLA) and Streptavidin-Tb (Cisbio, Cat No. 610SATLA) binds to TIGIT-mFc and biotinylated CD155 (R&D, Cat No. 2530-CD-050/CF). The intensity of the signal after addition of hybridoma purified antibody or humanized antibody was used to determine the activity of the antibody to block the binding of TIGIT to CD155. Particularly, the experimental procedures were described as follows:

Various concentrations of the test antibodies (hybridoma purified antibody or humanized antibody) diluted with dilution solution (PBS containing 1% BSA, pH 7.4) were added at 10 µl/well into a 384-well experimental plate (Corning, Cat No. 3706), centrifuged at 1000 rpm for 1 min, TIGIT-Fc or TIGIT-mFc diluted with sample dilution solution to a concentration of 2 µg/ml was added at 2.5 µl/well, centrifuged at 1000 rpm for 1 min, and then biotin-CD155 diluted to 4 µg/ml was added at 2.5 µl/well. The plate was centrifuged at 1000 rpm for 1 min and then pre-incubated at room temperature for 10 min, and then Pab Anti-Human IgG-Tb (Cisbio, Cat No. 61HFCTAA) diluted with sample dilution solution to 3.2 µg/ml and 0.08 µg/ml Streptavidin-XL665 (Cisbio, Cat No. 610SAXLA) was added at 2.5 µl/well, or Pab Anti-mouse-IgG-XL665 (Cisbio, Cat No. 61 PAMXLA) diluted with sample dilution solution to 3.2 µg/ml and 0.08 µg/ml Streptavidin-Tb (Cisbio, Cat No. 610SATLA) was added at 2.5 µl/well. The plate was placed at room temperature for 1 hour, and the emission values were detected at 665 nm and 620 nm with PHEARstar FS plate reader (BMG LABTECH). Data were analyzed with GraphPad Prism 5. The inhibitory activities of the TIGIT antibodies on the binding of human TIGIT to CD155 protein were calculated. The results are shown in FIGS. 5A and 5B.

Figure 6:
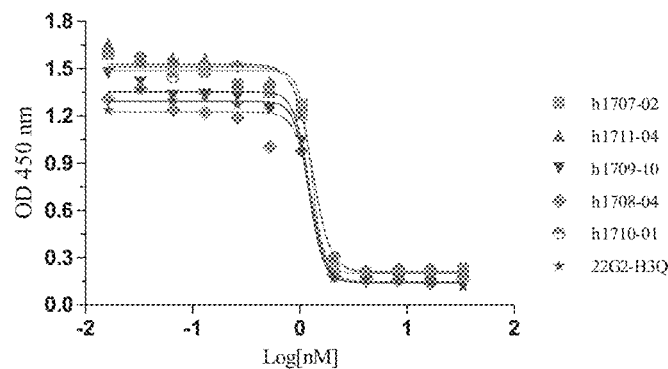
FIG. 6: Detection of effects of TIGIT antibodies on blocking the binding of TIGIT antigen to CHO cells overexpressing CD155.

Test Example 7: TIGIT Antibodies Block the Binding of TIGIT Antigen to CHO Cells Overexpressing CD155 by Blocking Assay The blocking ability of the anti-TIGIT antibodies was detected by an ELISA assay in which the antibodies blocked the binding of TIGIT to CHO cells overexpressing CD155. The full-length CD155 plasmid was transfected into CHO cells by electroporation, screened with pressure for two weeks, and the expression level of CD155 was examined. The cells overexpressing CD155 were fixed onto the bottom of a 96-well plate, TIGIT was pre-incubated with anti-TIGIT antibody diluted to various concentrations, and added into the plate. The signal intensity after addition of the secondary antibody was used to determine the ability of the antibody to block the binding of TIGIT to CHO cells overexpressing CD155. Particularly, the experimental procedures were described as follows:

CD155-CHO cells were seeded at a density of 5×10^5/ml, 100 µl/well was cultivated in 96-well plate overnight. The supernatant was discarded, the plate was washed three times with PBS, and then cell immunofixation solution (Beyotime, Cat No. P0098) was added at 100 µl/well for fixing the cells at room temperature for half an hour. The plate was washed with PBS four times. After discarding the liquid, 5% skim milk (BD skim milk, Cat No. 232100) blocking solution diluted with PBS was added at 200 μl/well, incubated at 37° C. for 3 hours for blocking. After blocking was finished, the blocking solution was discarded, the plate was washed 5 times with PBST buffer (PBS containing 0.05% Tween 20™, pH 7.4), and then pre-mixed solution of antigen-antibody was added at 50 μl/well and incubated in an incubator at 37° C. for 1 hour, wherein human TIGIT-hFc (produced in-house) or human TIGIT-mFc (produced in-house) diluted with sample dilution solution (PBS containing 1% BSA, pH 7.4) to a final concentration of 0.2 μg/ml was mixed with gradient concentrations of the antibodies to be tested and pre-incubated for 1 hour. After the incubation, the reaction solution was removed from the plate, and the plate was washed 5 times with PBST, HRP-labeled goat anti-human secondary antibody (Jackson Immuno Research, Cat No. 109-035-003) or goat anti-murine secondary antibody (Jackson Immuno Research, Cat No. 115-035-003) diluted with sample dilution solution was added at 50 μl/well, and incubated at 37° C. for 1 hour. The plate was washed with PBST for 5 times, TMB chromogenic substrate (KPL, Cat No. 52-00-03) was added at 50 μl/well, incubated at room temperature for 5-15 min, and 1M H2SO4 was added at 50 μl/well to terminate the reaction. The absorbance at a wavelength of 450 nm was read with microplate reader (Thermo scientific Multiskan, MK3). Data were analyzed with GraphPad Prism 5. The effect of the TIGIT antibodies on blocking the binding of the antigen to CHO cells overexpressing CD155 was calculated. The results are shown in FIG. 6.

Test Example 8: TIGIT Antibodies Block the Binding of CD155 Protein to CHO Cells Overexpressing TIGIT by Blocking Assay The blocking ability of the anti-TIGIT antibodies was detected by FACS assay in which the antibodies block the binding of CD155 to CHO cells overexpressing TIGIT. The full-length TIGIT plasmid was transfected into CHO cells by electroporation, screened with pressure for two weeks, and the expression level of TIGIT was examined. The cells overexpressing TIGIT were pre-incubated with various concentrations of the anti-TIGIT antibodies, and then fluorescently labeled CD155-Fc was added for incubation. The signal intensity was used to determine the ability of the antibody to block the binding of CD155 to CHO cells overexpressing TIGIT. Particularly, the experimental procedures were described as follows:

First, CD155-Fc (Sino Biological, Cat No. 10109-H02H) was labeled with CF™633 fluorescent dye (Sigma Aldrich, Cat No. MX633S100). CD155-Fc was dissolved in PBS to a concentration of 0.5-1 mg/ml, 9-fold sample volume of 10×Mix-n-Stain Reaction Buffer was added, and then thoroughly mixed. CF™633 fluorescent dye was added and incubated in dark at room temperature for 30 minutes. The procedure for fluorescence labelling was completed.

Figure 7:
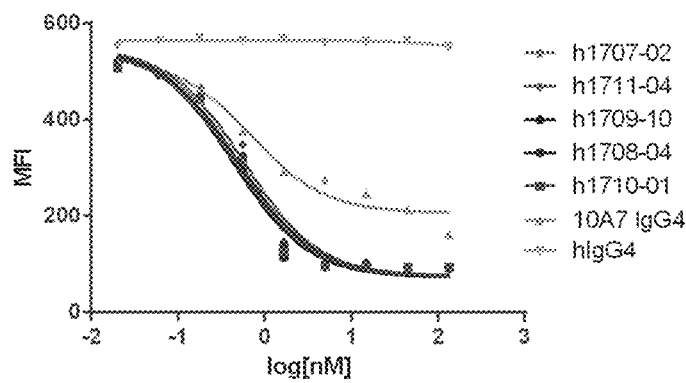
FIG. 7: Detection of effects of TIGIT antibodies on blocking the binding of CD155 to CHO cells overexpressing TIGIT.

TIGIT-CHO cells were seeded at a density of 5×10^6/ml, 100 μl/well in a 96-well round bottom plate (Corning, Cat No. 32915001), centrifuged at 1500 rpm for 5 minutes in a centrifuge (Beckman Coulter, Allegra® X-15R Centrifuge), and the supernatant was discarded. The cells were resuspended in 200 μl PBS, centrifuged again, and the supernatant was discarded. The cells were resuspended by adding 100 μl/well of the antibody solution to be tested which has been serially diluted with sample dilution solution (PBS containing 1% BSA, pH 7.4), and incubated at 4° C. for 1 hour. After the incubation, the cells were centrifuged at 1500 rpm for 5 minutes, the supernatant was discarded, and the cells were washed twice with the sample dilution solution. Then the cells were resuspended by adding 100 μl of 2 μg/ml CF™633 fluorescently labeled CD155-Fc solution, and incubated at 4° C. for 1 hour. After the incubation, the cells were centrifuged at 1500 rpm for 5 minutes, the supernatant was discarded, the cells were washed twice with sample dilution solution, and finally the cells were resuspended with 200 μl/well sample dilution solution. The intensity of fluorescence signal was measured on Flow Cytometer (BD FACSCanto™ II). Data were analyzed with GraphPad Prism 5. The ability of the TIGIT antibodies on blocking the binding of CD155 to TIGIT-CHO cells was calculated. The results are shown in FIG. 7 and the following table.

| | antibody | | | | | | |
|---|---|---|---|---|---|---|---|
| | h1707-02 | h1711-04 | h1709-10 | h1708-04 | h1710-01 | 10A7-IgG4 | hIgG4 |
| IC50 (nM) | 0.4824 | 0.5698 | 0.4269 | 0.4992 | 0.4675 | 0.6783 | >10000 |

In this test example, h1707-02, h1708-04, h1709-10, h1710-01 and h1711-04 antibodies were all capable of blocking the binding of CD155 to CHO cells overexpressing TIGIT.

Figure 8:
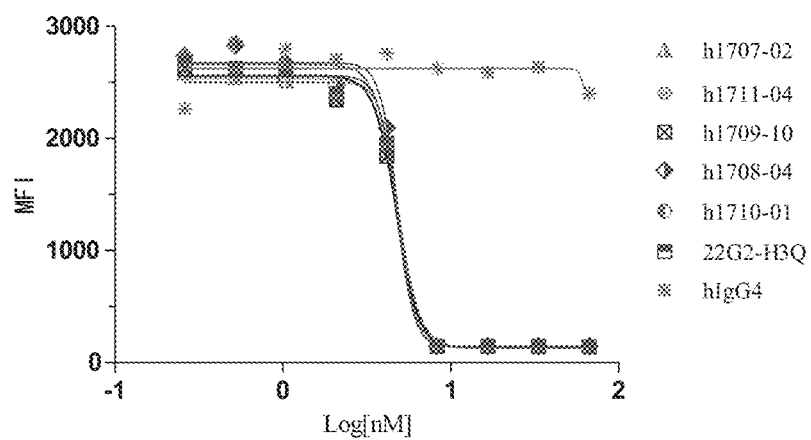
FIG. 8: Detection of effects of TIGIT antibodies on blocking the binding of TIGIT antigen to CHO cells overexpressing CD112.

Test Example 9: TIGIT Antibodies Block the Binding of TIGIT Antigen to CHO Cells Overexpressing CD112 by Blocking Assay The blocking ability of the anti-TIGIT antibodies was detected by FACS assay in which the antibodies block the binding of TIGIT to CHO cells overexpressing CD112. The full-length CD112 plasmid was transfected into CHO cells by electroporation, screened with pressure for two weeks, and the expression level of CD112 was examined. The TIGIT-mFc protein was pre-incubated with various concentrations of diluted anti-TIGIT antibody, and CHO cells overexpressing CD112 were added for incubation. The antibody labeled with PE label was added to detect the intensity of TIGIT signal, which was used to determine the ability of the antibody to block the binding of TIGIT to CHO cells overexpressing CD112. Particularly, the experimental procedures were described as follows:

Humanized antibody samples were diluted with 1% BSA, with nine concentration points starting from the concentration of 20 μg/mL. Meanwhile, TIGIT-mFc was diluted to 2 μg/mL. The antigen was mixed with various concentrations of the antibody at a ratio 1:1 of (by volume), and pre-incubated at 37° C. for 30 minutes. CD112-CHO cells were collected, washed once with PBS, and dispensed at 0.5*10^6/test. Cells were resuspended with 150 μl of antigen-antibody mixture, incubated at 4° C. for 60 minutes, and washed with 1% BSA for three times. The cells were resuspended in 100 μl of PE-goat anti-mouse IgG (Biolegend, 405307) dilution solution, incubated at 4° C. for 40 min, washed three times with 1% BSA, and resuspended with 200 μl of 1% BSA. Mean fluorescence intensity (MFI) of each sample was read on flow cytometry BD FACSCanto™ II. Data were analyzed with GraphPad Prism 5. The effect of the TIGIT antibodies on blocking the binding of the antigen to CD112-CHO cells was calculated. The results are shown in FIG. 8.

Figure 9:
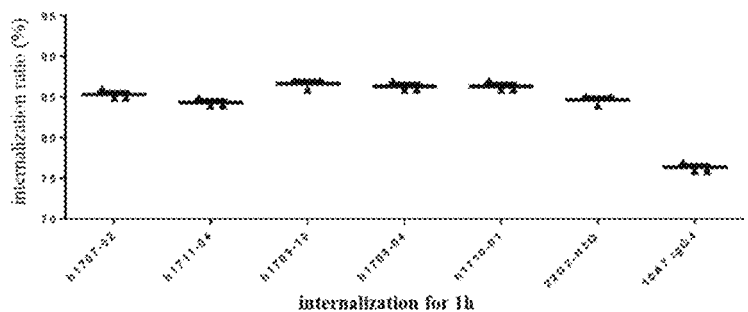
FIG. 9: Internalization of TIGIT antibodies into CHO cells overexpressing TIGIT, wherein internalization was tested for 1 hour.

Test Example 10: Binding Internalization Assay of TIGIT Antibodies on CHO Cells Overexpressing TIGIT To investigate the internalization of TIGIT antibodies upon binding to the antigen on cell surface, FACS assay was performed on CHO cells overexpressing full-length TIGIT to test the internalization of TIGIT antibodies. Particularly, the experimental procedures were described as follows:

TIGIT-CHO cells were seeded at a density of $2 \times 10^6$/ml, 100 μl/well in a 96-well round bottom plate (Corning, Cat No. 32915001), and centrifuged at 1500 rpm for 5 minutes in a centrifuge (Beckman Coulter, Allegra® X-15R Centrifuge). The supernatant was discarded. The cells were resuspended in 200 μl of 1% BSA and centrifuged, and again the supernatant was discarded. The humanized antibody samples were diluted to a concentration of 4 μg/mL with 1% BSA, and added into the cells at 100 μl/well to resuspend the cells. The resuspended cells were incubated on ice for 1 hour. After the incubation, the cells were centrifuged at 1500 rpm for 5 minutes, the supernatant was discarded, the cells were washed three times with 1% BSA, resuspended with 10% FBS-DMEM/F-12 culture medium and aliquoted into two parts: one was incubated in the incubator at 37° C. for 1 hour (Internalization group) and the other was incubated on ice for 1 hour (Binding affinity group). After the incubation, the cells were washed once with 1% BSA and then incubated with PE-anti-Fc antibody (Jackson, 109-115-098) diluted in 1% BSA on ice for 1 hour. The cells were washed with 1% BSA for three times and resuspended in 1% BSA. MFI of each sample was read on flow cytometer BD FACSCanto™ II. The internalization ratio of the antibody was calculated according to the following formula. Note: "Blank" means that MFI was read after incubating merely with PE-anti-Fc antibody diluted with 1% BSA, without anti-TIGIT antibody, on ice for 1 hour, and then washed three times and resuspended. The results are shown in FIG. 9.

Internalization Ratio %=(Binding affinity group–Internalization group)*100/(Binding affinity group–Blank group)

Test Example 11: Cell Killing Assay of Natural Killer Cells (NK)

In order to study the effect of the TIGIT antibodies on NK cell killing function, human peripheral blood mononuclear cells (PBMCs) were collected and purified, natural killer cells (NKs) were extracted, and co-cultivated with human colorectal cancer cell line WiDr for 4 hours to detect the secretion level of lactate dehydrogenase (LDH). Particularly, the experimental procedures were described as follows:

Human colorectal cancer cell line WiDr was cultivated in MEM culture medium supplemented with 10% (v/v) fetal bovine serum (FBS) at 37° C. under 5% $CO_2$. PBMCs were obtained from fresh blood by Ficoll®-Hypaque density gradient centrifugation (Stem Cell Technologies), and human primary NK cells were extracted from freshly isolated PBMC (Miltenyi, CAT #130-092-657) and cultivated at 37° C. under 5% $CO_2$ in RPMI 1640 medium supplemented with 10% (v/v) FBS.

Figure 10A:
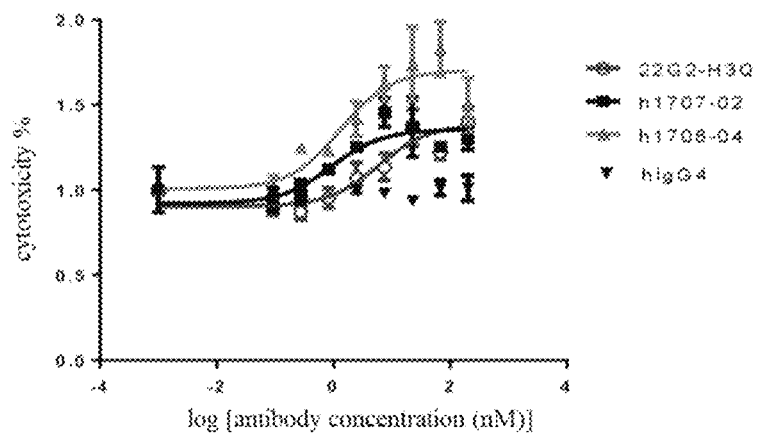
FIG. 10A: Assay showing that TIGIT antibodies promote the killing effects of natural killer cells (NK)
Figure 10B:
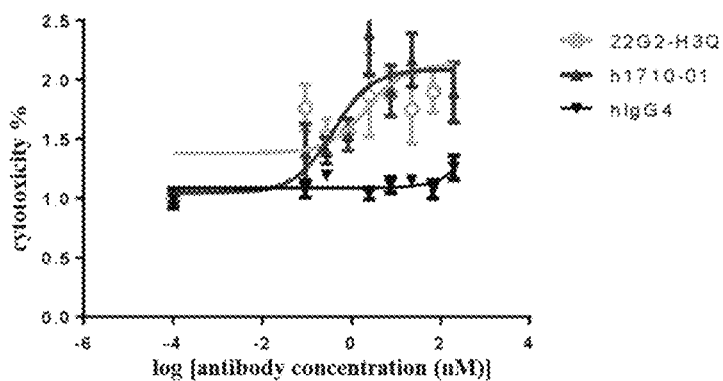
FIG. 10B: Assay showing that TIGIT antibodies promote the killing effects of natural killer cells (NK).

Human primary NK cells were seeded into 6-well cell culture plate at a cell density of approximately $2 \times 10^6$/ml, 100 U/mL of human IL-2 was added and incubated overnight. The cells were washed with phenol red-free RPMI 1640 medium, resuspended, and seeded in a 96-well U-bottom plate at a cell density of approximately $3 \times 10^5$ cells/well. Meanwhile, serially diluted antibody samples (diluted in PBS) or an equivalent amount of homo-IgG (as a blank control) was added. After incubating at 37° C., 5% $CO_2$ for 1 hour, the target cell WiDr was co-cultivated with human primary NK cells at a ratio of 1:1, at 37° C., 5% $CO_2$ for 4 hours. The cell culture supernatant was collected. The level of LDH secreted into the cell culture supernatant was measured using the CytoTox 96® Non-Radioactive Cytotoxicity Assay (Promega, CAT #G1780) according to the manufacturer's instruction. The percentage of specific cytolysis was determined by the following formula: % lysis=100×(ER−SR1−SR2)/(MR−SR1), wherein ER, SR (1 & 2) and MR represent experimental, spontaneous ("1" for the target cell and "2" for human primary NK cells) and maximal LDH release, respectively. Spontaneous release was the release of LDH by the target cells or human primary NK cells cultivated in culture medium alone, and the maximal release was the LDH determined when all target cells were lysed by the lysis buffer. Results are shown in FIG. 10A or FIG. 10B and the following table. Humanized TIGIT candidate antibody h1707-02, h1708-04, h1710-01 and other antibodies can enhance the killing of target cells by human primary NK cells to varying degrees, and showing drug concentration-dependent effect.

| | h1707-02 | h1708-04 | 22G2-H3Q | h1710-01 | 22G2-H3Q |
|---|---|---|---|---|---|
| IC50 (nM) | 0.9 | 1.29 | 5.78 | 0.38 | 2.23 |

Test Example 12: Experiment of PBMC-T Lymphocyte Activation

To investigate the impact of TIGIT antibodies on human primary T lymphocyte function, human peripheral blood mononuclear cells (PBMCs) were collected and purified. The level of secreted cytokine IFNγ was measured after stimulating in vitro with tuberculin (TB) for 5 days. Particularly, the experimental procedure was described as follows:

PBMCs were obtained from fresh blood by Ficoll®-Hypaque density gradient centrifugation (Stem Cell Technologies), and were cultivated in RPMI 1640 culture medium supplemented with 10% (v/v) FBS at 37° C., 5% $CO_2$.

Figure 11:
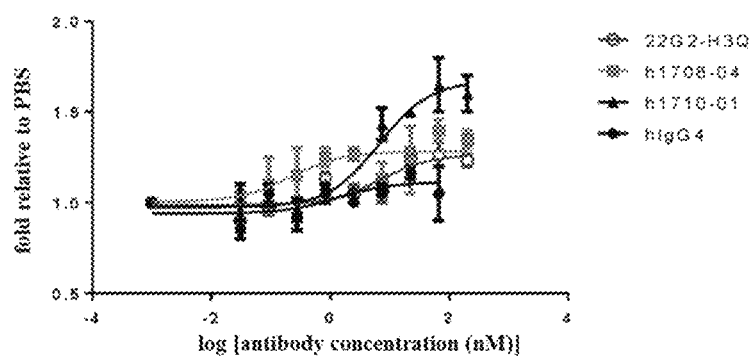
FIG. 11: Assay showing that TIGIT antibodies activate PBMC-T lymphocytes.

The density of the freshly purified PBMCs were adjusted to $2 \times 10^6$/ml in RPMI 1640 medium. 25 μl of tuberculin was added into 20 mL of the cell suspension, and cultivated at 37° C., 5% $CO_2$ for 5 days. On day 5, CD155 (recombinant CD155/PVR Protein, R&D, 2530-CD-050/CF) was added to a 96-well cell culture plate at 0.25 μg per well and coated overnight at 4° C. On day 6, the above cultivated cells were collected and centrifuged, washed once with PBS, and resuspended in fresh RPMI 1640 culture medium to adjust the density to $1 \times 10^6$/ml. The cells were seeded into a CD155-coated 96-well cell culture plate, 90 μl per well. Serially diluted antibody samples (diluted with PBS) or an equivalent amount of isotype IgG (as a blank control) was added, 10 μl per well. The cell culture plate was incubated in the incubator at 37° C., 5% $CO_2$ for 3 days. The cell culture plate was taken out and centrifuged at 4000 rpm for 10 min. The cell culture supernatant was collected and the level of IFN-γ was measured by ELISA method (human IFN-γ detection kit, NEOBioscience, EHC 102 g. 96) according to the manufacturer's instruction. The results are shown in FIG. 11. TIGIT humanized candidate antibody h1708-04, h1710-01 and other antibodies can increase the level of cytokine IFN-γ secreted by activated primary T lymphocytes to varying degrees, showing drug concentration-dependent effect.

Test Example 13: Pharmacokinetic Evaluation of Humanized TIGIT Antibodies in Rats SD male rats, with weight of 180-240 g, were purchased from Sippr-BK Laboratory Animal Co., Ltd. During the feeding period, food and water were taken ad libitum. Adaption for laboratory environment was no less than 3 days, with 12/12 hour light/dark cycle adjustment, temperature of 16-26° C., and relative humidity of 40-70%. One day before the start of the experiment, SD rats were numbered and randomly divided into groups, with 3 rats per group. On the day of the experiment, the five groups were injected intravenously or subcutaneously with the test drug h1707-02, h1708-04, h1710-01, h1711-04 and h1709-10, respectively. 22G2-H3Q was used as a positive control at a dose of 3 mg/kg. For all groups, the injection volume was 5 ml/kg.

For intravenous injection, blood samples were collected at time points, i.e., prior to, 5 min, 8 h, 1 d, 2 d, 4 d, 7 d, 10 d, 14 d, 21 d, and 28 d after the administration. For subcutaneous injection, blood samples were collected at time points, i.e., prior to, 1 h, 4 h, 8 h, 1 d, 2 d, 4 d, 8 d, 11 d, 14 d, 21 d, and 28 d after the administration. For each animal, 0.2 ml of whole blood was taken in absence of anticoagulant. The blood samples were placed at 4° C. for 30 min, centrifuged at 1000 g for 15 min, and the supernatant was removed into an EP tube and stored at −80° C.

Figure 12:
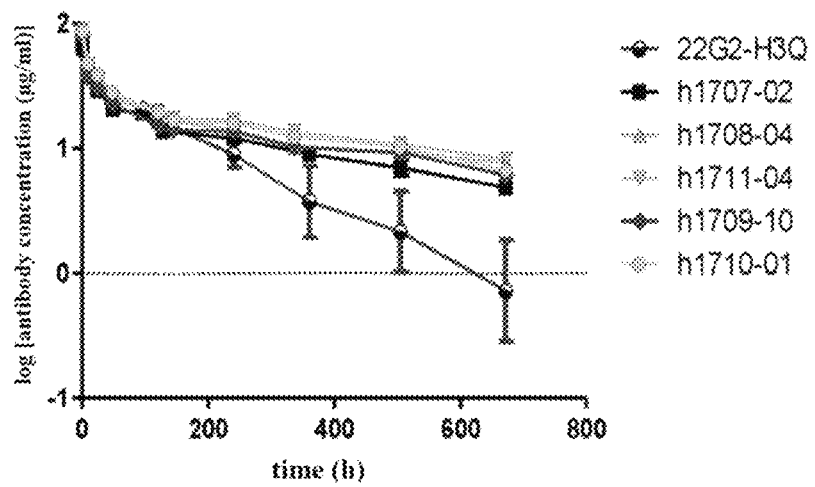
FIG. 12: In vivo pharmacokinetic assay of humanized TIGIT antibodies in rats.

The serum concentration of the antibody was measured by ELISA method (see Example 3 and Test Example 1), and the pharmacokinetic parameters of the test drug were calculated with Winnolin software. The main pharmacokinetic results are shown in FIG. 12.

From the detection, it can be seen that exposed quantities of anti-TIGIT antibody h1707-02, h1708-04, h1710-01, h1709-10 and h1711-04 in rats were similar after the SD rats were administered intravenously 3 mg/kg of the above antibodies. The bioavailability after subcutaneous administration was high and was close to 100%. The elimination half-life of each antibody was longer than that of the 22G2-H3Q antibody.

Test Example 14: Detection of the Thermal Stability of the Humanized TIGIT Antibodies by UNIT Test The thermal stabilities in different buffer systems were compared. Exemplary buffer systems corresponding to different pHs were 10 mM PBS (pH 7.4), 15 mM His (pH 6.0), and 10 mM Acetate acid (pH 5.2). The samples were dissolved in the corresponding buffers respectively, and the concentration was controlled at about 50 mg/ml. The detection was performed by UNIT. For detection, 9 μl of sample was pipetted into the sample slot equipped within the instrument, avoiding air bubbles. The sample slot was clamped tightly and placed into the instrument. The running parameters were set as follows: Start Temp 20° C.; Incubation 0s; Rate 0.3° C./min; Plate Hold 5 s; End Temp 95° C.

h1707-02, h1708-04, h1710-01, h1709-10, h1711-04 and other antibodies showed good thermal stability in several test systems.

TABLE 5

Thermal stability of the antibody

| protein | buffer | Tagg (° C.) | Tonset (° C.) | Tm1 (° C.) | Tm2 (° C.) |
|---------|--------|-------------|---------------|------------|------------|
| h1707-02 | PBS (pH 7.4) | 69.0 | 61.0 | 70.49 | |
| h1711-04 | 10 mM | 74.3 | 54.3 | 69.7 | 80.7 |
| h1709-10 | Acetate | 74.5 | 59.6 | 69.4 | |
| h1708-04 | acid buffer | 71.5 | 60.4 | 69.4 | 78.3 |
| h1710-01 | (pH 5.2) | 76.8 | 57.2 | 67.7 | 77.6 |

Test Example 15. Investigation of the Cycle Stability Under Certain Concentrations by Monitoring the Purity of the Sample by SEC-HPLC After being subjected to 5 freeze-thaw cycles at −80° C., storage at 4° C., and at 40° C. for 28 days, the stability of antibodies was compared under different exemplary conditions, such as at a concentration of about 50 mg/ml, in 10 mM PBS (pH 7.4), 15 mM His (pH 6.0), 10 mM acetate acid (pH 5.2). The purity of the antibodies was detected by Xbridge protein BEH SEC 200A (Waters) HPLC column. h1707-02, h1708-04, h1709-10, h1710-01, h1711-04, etc. all showed good stability, and SEC purity was not significantly changed after being accelerated at 40° C. for one month.

| antibody | buffer | Initial purity | −80° C. frozen and thawed for five times | 4° C. for 28 days | 40° C. for 28 days |
|----------|--------|----------------|-------------------------------------------|---------------------|---------------------|
| h1707-02 | PBS buffer | 98.16% | 98.39% | 97.82% | 94.91% |
| h1711-04 | (pH 7.4) | 98.00% | | | 96.79% |
| h1709-10 | | 97.20% | | | 96.03% |
| h1708-04 | | 98.68% | 98.76% | 98.70% | 97.68% |
| h1710-01 | | 98.73% | | 98.73% | 97.96% |
| h1707-02 | 10 mM acetate | 99.37% | 99.78% | 99.34% | 98.42% |
| h1711-04 | acid buffer | 98.00% | | | 97.58% |
| h1709-10 | (pH 5.2) | 97.29% | | | 96.73% |
| h1708-04 | | 98.61% | 98.40% | 98.71% | 97.80% |
| h1710-01 | | 98.77% | | 98.77% | 98.63% |
| h1707-02 | His buffer | 99.73% | 99.73% | 99.61% | 98.64% |
| h1711-04 | (pH 6.0) | 98.31% | | | 97.64% |
| h1709-10 | | 97.89% | | | 96.68% |
| h1708-04 | | 98.95% | 99.10% | 99.09% | 98.06% |
| h1710-01 | | 98.93% | | 98.93% | 98.79% |

Test Example 16. Chemical Stability of the Antibodies

Chemical stability of antibody molecules such as h1707-02, h1708-04, h1709-10, h1710-01 and h1711-04 was detected. 500 μg of the antibody to be tested was dissolved in 500 μl of PBS pH 7.4, and incubated in a water bath at 40° C. Samples were taken at day 0, 14, and 28, respectively, for enzymatic digestion experiment. 100 μg samples taken at various time points were dissolved in 100 μl of 0.2 M His-HCl, 8 M Gua-HCl, pH 6.0, 3 μl of 0.1 g/mL DTT was added, incubated in a water bath at 50° C. for 1 hour, and then ultrafiltered twice with 0.02 M His-HCl, pH 6.0. Three µl of 0.25 mg/mL trypsin was added and incubated in a water bath at 37° C. overnight for enzymatic digestion. LC-MS analysis was performed with Agilent 6530 Q-TOF. The results showed that after being accelerated at 40° C. for 1 month, h1707-02, h1708-04, h1709-10, h1710-01 and h1711-04 did not show any significant unstable change, such as water loss, oxidation and deamidation, suggesting the molecules have good chemical stability.

The above described invention has been described in detail with the aid of the accompanying drawings and examples. However, the description and examples should not be construed as limiting the scope of the disclosure. The disclosures of all patents and scientific literatures cited herein are expressly incorporated by reference in their entirety.

The invention claimed is:

1. A monoclonal antibody or antigen-binding fragment thereof, specifically binding to human TIGIT, comprising a heavy chain variable region and a light chain variable region, wherein
the heavy chain variable region comprises HCDR1, HCDR2 and HCDR3 as set comprising sequences of SEQ ID NOs: 21, 22 and 23, respectively; and the light chain variable region comprises LCDR1, LCDR2 and LCDR3 comprising sequences of SEQ ID NOs: 24, 25 and 26, respectively.

2. The monoclonal antibody or antigen-binding fragment thereof according to claim 1, wherein the monoclonal antibody is a recombinant antibody.

3. The monoclonal antibody or antigen-binding fragment thereof according to claim 2, wherein the recombinant antibody is a humanized antibody comprising light and heavy chain framework region (FR) sequences derived from human germline light and heavy chain, or mutated sequences thereof, respectively.

4. The monoclonal antibody or antigen-binding fragment thereof according to claim 3, wherein the heavy chain variable region of the humanized antibody comprises a sequence of SEQ ID NO: 51, or a variant thereof having 1-3 back mutations on the FR of the heavy chain variable region of SEQ ID NO: 51, wherein the back mutations are selected from the group consisting of M48I, R72V and V79A.

5. The monoclonal antibody or antigen-binding fragment thereof according to claim 3, wherein the heavy chain variable region sequence of the humanized antibody is selected from the group consisting of: SEQ ID NO: 51, SEQ ID NO: 54 and SEQ ID NO: 55.

6. The monoclonal antibody or antigen-binding fragment thereof according to claim 3, wherein the light chain variable region of the humanized antibody comprises a sequence of SEQ ID NO: 52, or a variant thereof having the back mutation A43S.

7. The monoclonal antibody or antigen-binding fragment thereof according to claim 3, wherein the light chain variable region sequence of the humanized antibody is selected from the group consisting of SEQ ID NO: 52 and SEQ ID NO:53.

8. The monoclonal antibody or antigen-binding fragment thereof according to claim 3, wherein the humanized antibody comprises: a heavy chain variable region of any one of SEQ ID NOs: 51, 54 and 55, and a light chain variable region of SEQ ID NO: 52 or 53.

9. The monoclonal antibody or antigen-binding fragment thereof according to claim 8, wherein the humanized antibody comprises a heavy chain variable region of SEQ ID NO: 51 and a light chain variable region of SEQ ID NO: 53.

10. The monoclonal antibody or antigen-binding fragment thereof according to claim 1, wherein the antibody is a full-length antibody, further comprising a human antibody heavy chain constant region comprising a sequence of SEQ ID NO: 78 and a human light chain constant region comprising a sequence of SEQ ID NO: 79.

11. The monoclonal antibody or antigen-binding fragment thereof according to claim 1, wherein the antigen-binding fragment is selected from the group consisting of Fab, Fab', F(ab') 2, single-chain antibody (scFv), dimerized V region (diabody), disulfide-stabilized V region (dsFv) and a peptide comprising CDRs.

12. A pharmaceutical composition comprising a therapeutically effective amount of the monoclonal antibody or antigen-binding fragment thereof according to claim 1, and one or more pharmaceutically acceptable carriers, diluents, buffers or excipients.

13. An isolated nucleic acid molecule encoding the monoclonal antibody or antigen-binding fragment thereof according to claim 1.

14. A recombinant vector comprising the nucleic acid molecule of claim 13.

15. A host cell transformed with the recombinant vector of claim 14, wherein the host cell is selected from the group consisting of prokaryotic cell and eukaryotic cell.

16. A method comprising cultivating the host cell of claim 15 in culture to form and accumulate the monoclonal antibody or antigen-binding fragment thereof, and recovering the monoclonal antibody or antigen-binding fragment thereof from the culture.

17. A method for detecting or measuring human TIGIT, comprising the step contacting the human TIGIT with the monoclonal antibody or antigen-binding fragment thereof according to claim 1.

18. A method for treating a disease associated with human TIGIT, comprising administering to a subject a pharmaceutically effective amount of the pharmaceutical composition of claim 12, wherein the disease associated with human TIGIT is tumor, cancer, or immune disease.

19. The method of claim 18, wherein the disease associated with human TIGIT is tumor or cancer.

\* \* \* \* \*